United States Patent
McClain et al.

(10) Patent No.: US 10,508,270 B2
(45) Date of Patent: Dec. 17, 2019

(54) COORDINATED COEXPRESSION OF THROMBIN

(71) Applicants: Aronora, Inc., Portland, OR (US); AbSci, LLC, Portland, OR (US)

(72) Inventors: Sean McClain, Portland, OR (US); Mark Valasek, San Diego, CA (US); Andras Gruber, Portland, OR (US)

(73) Assignees: AbSci LLC, Vancouver, WA (US); Aronora Inc., Portland, OR (US)

( * ) Notice: Subject to any disclaimer, the term of this patent is extended or adjusted under 35 U.S.C. 154(b) by 487 days.

(21) Appl. No.: 14/909,707

(22) PCT Filed: Feb. 5, 2014

(86) PCT No.: PCT/US2014/014968
§ 371 (c)(1),
(2) Date: Feb. 2, 2016

(87) PCT Pub. No.: WO2015/020690
PCT Pub. Date: Feb. 12, 2015

(65) Prior Publication Data
US 2016/0160203 A1    Jun. 9, 2016

Related U.S. Application Data

(63) Continuation-in-part of application No. PCT/US2013/053562, filed on Aug. 5, 2013.

(60) Provisional application No. 61/747,246, filed on Dec. 29, 2012, provisional application No. 61/697,751, filed on Aug. 5, 2012.

(51) Int. Cl.
*C12N 15/70* (2006.01)
*C12N 15/67* (2006.01)
*C12N 9/74* (2006.01)
*C12N 15/09* (2006.01)

(52) U.S. Cl.
CPC .... *C12N 9/6429* (2013.01); *C12Y 304/21005* (2013.01)

(58) Field of Classification Search
None
See application file for complete search history.

(56) References Cited

U.S. PATENT DOCUMENTS

| 2004/0120943 | A1* | 6/2004 | Gruber | C12N 9/6429 424/94.64 |
| 2009/0203081 | A1 | 8/2009 | Keasling | |
| 2012/0164129 | A1 | 6/2012 | Di Cera | |

FOREIGN PATENT DOCUMENTS

| EP | 2386641 A1 | 11/2011 |
| WO | 2006133210 A2 | 12/2006 |

OTHER PUBLICATIONS

Cantrell, S.A. 2003 *E. coli* Plasmid Vectors in Methods in Molecular Biology vol. 235: 257-275. (Year: 2003).*
Samuelson, J.C. 2011 Heterologous Gene Expression in *E. coli* in Methods in Molecular Biology vol. 705: 195-209. (Year: 2011).*
Hirel, "Extent of N-terminal methionine excision from *Escherichia coli* proteins is governed by the side-chain length of the penultimate amino acid", Proc Natl Acad Sci U S A Nov. 1989; 86(21): 8247-8251.
Lobstein, "SHuffle, a novel *Escherichia coli* protein expression strain capable of correctly folding disulfide bonded proteins in its cytoplasm", Microb Cell Fact May 8, 2012; 11: 56; doi: 10.1186/1475-2859-11-56.
Makino, "Strain engineering for improved expression of recombinant proteins in bacteria", Microb Cell Fact May 14, 2011; 10: 32; doi: 10.1186/1475-2859-10-32.
Sørensen and Mortensen, "Advanced genetic strategies for recombinant protein expression in *Escherichia coli*", J Biotechnol Jan. 26, 2005; 115(2): 113-128; Review.
Skerra, "Bacterial expression of immunoglobulin fragments", Curr Opin Immunol Apr. 1993; 5(2): 256-262; Review.
Lee and Keasling, "A propionate-inducible expression system for enteric bacteria", Appl Environ Microbiol Nov. 2005; 71(11): 6856-6862.
Khlebnikov, "Homogeneous expression of the P(BAD) promoter in *Escherichia coli* by constitutive expression of the low-affinity high-capacity AraE transporter", Microbiology Dec. 2001; 147(Pt 12): 3241-3247.
Morgan-Kiss, "Long-term and homogeneous regulation of the *Escherichia coli* araBAD promoter by use of a lactose transporter of relaxed specificity", Proc Natl Acad Sci U S A May 28, 2002; 99(11): 7373-7377.
Froese, "Sleeping beauty mutase (sbm) is expressed and interacts with ygfd in *Escherichia coli*", Microbiol Res 2009; 164(1): 1-8; doi: 10.1016/j.micres.2008.08.006; Epub Oct. 23, 2008.
Ollis, "Cytoplasmic membrane proton motive force energizes periplasmic interactions between ExbD and TonB", Mol Microbiol Aug. 2009; 73(3): 466-481; doi: 10.1111/j.1365-2958.2009.06785.x; Epub Jul. 16, 2009.
"Titratable control of pBAD and lac promoters in individual *E. coli* cells", http://openwetware.org/wiki/Titratable_control_of_pBAD_and_lac_promoters_in_individual_E._coli_cells, last updated Jan. 23, 2008, accessed Apr. 19, 2012.
Guzman, et al., "Tight regulation, modulation, and high-level expression by vectors containing the arabinose PBAD promoter", J Bacteriol Jul. 1995; 177(14): 4121-4130.
Park et al., "The mechanism of sugar-mediated catabolite repression of the propionate catabolic genes in *Escherichia coli*", Gene Aug. 1, 2012; 504(1): 116-121, Epub May 3, 2012.
Mayer, "A new set of useful cloning and expression vectors derived from pBlueScript", Gene Sep. 22, 1995; 163(1): 41-46.

(Continued)

*Primary Examiner* — Marsha Tsay
(74) *Attorney, Agent, or Firm* — IP Department, AbSci LLC; Suzanne A. Sprunger

(57) ABSTRACT

The present invention provides methods of producing thrombin using coordinated coexpression systems, and particularly inducible coexpression systems, capable of controlled induction of expression of each gene product required for the production of thrombin, and the thrombin produced by this method.

14 Claims, 5 Drawing Sheets

Specification includes a Sequence Listing.

(56) References Cited

OTHER PUBLICATIONS

ISA/US, International Search Report, PCTUS2014014968, dated Aug. 5, 2014.
ISA/US, Written Opinion, PCTUS2014014968, dated Aug. 5, 2014.
EPO, Extended Search Results, EP14834543, dated Jan. 25, 2017.
USPTO, Non-Final Office Action in U.S. Appl. No. 14/419,653 (issued as U.S. Pat. No. 9,617,335B2); dated Feb. 2, 2016.
USPTO, Final Office Action in U.S. Appl. No. 14/419,653 (issued as U.S. Pat. No. 9,617,335B2); dated Aug. 9, 2016.
AbSci LLC, Applicant Response After Final Office Action in U.S. Appl. No. 14/419,653 (issued as U.S. Pat. No. 9,617,335B2); dated Oct. 15, 2016.
USPTO, Non-Final Office Action in U.S. Appl. No. 14/952,535; dated Jun. 27, 2017.
USPTO, Final Office Action in U.S. Appl. No. 14/952,535; dated May 31, 2018.
AbSci LLC, Applicant Response After Final Office Action in U.S. Appl. No. 14/952,535; dated Nov. 20, 2018.
USPTO, Non-Final Office Action in U.S. Appl. No. 14/952,535; dated Dec. 28, 2018.
AbSci LLC, Applicant Response to Non-Final Office Action in U.S. Appl. No. 14/952,535; dated Feb. 26, 2019.
USPTO, Non-Final Office Action in U.S. Appl. No. 15/261,984; dated Apr. 17, 2018.
AbSci LLC, Applicant Response to Non-Final Office Action in U.S. Appl. No. 15/261,984; dated Aug. 22, 2018.
USPTO, Final Office Action in U.S. Appl. No. 15/261,984; dated Dec. 12, 2018.
USPTO, Non-Final Office Action in U.S. Appl. No. 15/434,869; dated Nov. 2, 2018.
IP Australia, Examination Report in AU2013299910; dated Mar. 28, 2018.
Canadian IP Office, Examination Report in CA2880285; dated Jan. 15, 2019.
People's Republic of China State Intellectual Property Office; First Office Action in CN201380041522.X, dated Jul. 1, 2016.
People's Republic of China State Intellectual Property Office; First Office Action in CN201380041522.X, dated Jul. 1, 2016; Complete English translation and claims.
EPO Examining Division Communication in EP13756743; dated May 17, 2016.
AbSci LLC; Applicant Response in EP13756743; dated Aug. 16, 2016.
EPO Examining Division Communication in EP13756743 (Intention to Grant); dated Sep. 16, 2016.
European Patent Office, Search Opinion in EP16201998; dated May 3, 2017.
Japan Patent Office, First Notification of Reasons for Refusal in JP 2015526598; dated Jun. 22, 2017.
Japan Patent Office, Second Notification of Reasons for Refusal in JP 2015526598; dated Jan. 30, 2018.
Khlebnikov et al., "Regulatable arabinose-inducible gene expression system with consistent control in all cells of a culture", J Bacteriol Dec. 2000; 182(24): 7029-7034.
CIPO, Office Action in CN201380041522X; dated May 10, 2019.
CIPO, Office Action in CN201380041522X, English Translation; dated May 10, 2019.

* cited by examiner

SEQUENCE LISTING

<160> NUMBER OF SEQ ID NOS: 22

<210> SEQ ID NO 1
<211> LENGTH: 622
<212> TYPE: PRT
<213> ORGANISM: Homo sapiens

<400> SEQUENCE: 1

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

```
Asp Ala Glu Ile Gly Met Ser Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620

<210> SEQ ID NO 2
<211> LENGTH: 140
<212> TYPE: DNA
<213> ORGANISM: Artificial Sequence
<220> FEATURE:
<223> OTHER INFORMATION: Optimized coding sequence for human thrombin A
      chain (with methionine residue added to the N-terminal end)

<400> SEQUENCE: 2
gctagcagga ggaattcacc atgactttcg gtagcggcga agcagattgc ggtttgcgtc        60
cattatttga agaaaaagc ctggaagata aaccgagcg cgaactgctg gagtcctaca       120
tcgacggccg ttaagtcgac                                                  140

<210> SEQ ID NO 3
<211> LENGTH: 37
<212> TYPE: PRT
<213> ORGANISM: Artificial Sequence
<220> FEATURE:
<223> OTHER INFORMATION: Human thrombin A chain (with methionine residue
      added to the N-terminal end)

<400> SEQUENCE: 3

Met Thr Phe Gly Ser Gly Glu Ala Asp Cys Gly Leu Arg Pro Leu Phe
1               5                   10                  15
```

```
Glu Lys Lys Ser Leu Glu Asp Lys Thr Glu Arg Glu Leu Leu Glu Ser
             20                  25                  30

Tyr Ile Asp Gly Arg
        35

<210> SEQ ID NO 4
<211> LENGTH: 260
<212> TYPE: PRT
<213> ORGANISM: Artificial Sequence
<220> FEATURE:
<223> OTHER INFORMATION: Human thrombin B chain (with methionine residue
      added to the N-terminal end)

<400> SEQUENCE: 4

Met Ile Val Glu Gly Ser Asp Ala Glu Ile Gly Met Ser Pro Trp Gln
1               5                   10                  15

Val Met Leu Phe Arg Lys Ser Pro Gln Glu Leu Leu Cys Gly Ala Ser
             20                  25                  30

Leu Ile Ser Asp Arg Trp Val Leu Thr Ala Ala His Cys Leu Leu Tyr
         35                  40                  45

Pro Pro Trp Asp Lys Asn Phe Thr Glu Asn Asp Leu Leu Val Arg Ile
    50                  55                  60

Gly Lys His Ser Arg Thr Arg Tyr Glu Arg Asn Ile Glu Lys Ile Ser
65                  70                  75                  80

Met Leu Glu Lys Ile Tyr Ile His Pro Arg Tyr Asn Trp Arg Glu Asn
                85                  90                  95

Leu Asp Arg Asp Ile Ala Leu Met Lys Leu Lys Lys Pro Val Ala Phe
            100                 105                 110

Ser Asp Tyr Ile His Pro Val Cys Leu Pro Asp Arg Glu Thr Ala Ala
        115                 120                 125

Ser Leu Leu Gln Ala Gly Tyr Lys Gly Arg Val Thr Gly Trp Gly Asn
    130                 135                 140

Leu Lys Glu Thr Trp Thr Ala Asn Val Gly Lys Gly Gln Pro Ser Val
145                 150                 155                 160

Leu Gln Val Val Asn Leu Pro Ile Val Glu Arg Pro Val Cys Lys Asp
                165                 170                 175

Ser Thr Arg Ile Arg Ile Thr Asp Asn Met Phe Cys Ala Gly Tyr Lys
            180                 185                 190

Pro Asp Glu Gly Lys Arg Gly Asp Ala Cys Glu Gly Asp Ser Gly Gly
        195                 200                 205

Pro Phe Val Met Lys Ser Pro Phe Asn Asn Arg Trp Tyr Gln Met Gly
    210                 215                 220

Ile Val Ser Trp Gly Glu Gly Cys Asp Arg Asp Gly Lys Tyr Gly Phe
225                 230                 235                 240

Tyr Thr His Val Phe Arg Leu Lys Lys Trp Ile Gln Lys Val Ile Asp
                245                 250                 255

Gln Phe Gly Glu
        260

<210> SEQ ID NO 5
<211> LENGTH: 809
<212> TYPE: DNA
<213> ORGANISM: Artificial Sequence
<220> FEATURE:
<223> OTHER INFORMATION: Optimized coding sequence for human W215A E217A
      thrombin B chain (with methionine residue added to the N-terminal
      end)

<400> SEQUENCE: 5
```

-continued

```
gctagcagga ggaattcacc atgattgttg aaggttcgga cgcagaaatc ggtatgtcac    60
catggcaagt tatgttgttt cgcaaaagcc cgcaagagct gctgtgtggt gcctccctga   120
tttccgaccg ctgggtcctg accgcagcgc actgtctgct gtatccgccg tgggataaga   180
atttcaccga gaatgacctg ttggtgcgca ttggcaaaca cagccgtacg cgctacgaac   240
gtaacatcga aagatcagc atgctggaga aaatctacat tcaccctcgt tataactggc   300
gtgagaactt ggaccgtgac atcgctctga tgaagctgaa gaaaccggtt gcgttcagcg   360
attacattca tccggtttgt ctgccggatc gcgagactgc cgcgagcctg ttacaagccg   420
gctataaggg tcgtgtaacg ggctggggta atctgaagga aacctggacc gcgaatgtcg   480
gtaaaggtca gccgagcgtg ctgcaagtgg ttaatctgcc gattgttgaa cgtccggtct   540
gcaaggatag cacccgcatt cgtatcacgg acaacatgtt ttgcgcaggc tacaagccag   600
atgaaggcaa gcgtggtgat gcttgcgagg gcgacagcgg tggcccgttt gtgatgaaat   660
ctccgttcaa caaccgttgg taccagatgg gtatcgtgag cgcgggtgcg ggttgcgacc   720
gtgacggtaa atacggcttc tatacccatg tgtttcgcct gaaaaagtgg atccagaaag   780
tcattgatca gttcggcgag taagtcgac                                    809
```

<210> SEQ ID NO 6
<211> LENGTH: 260
<212> TYPE: PRT
<213> ORGANISM: Artificial Sequence
<220> FEATURE:
<223> OTHER INFORMATION: Human W215A E217A thrombin B chain (with methionine residue added to the N-terminal end)

<400> SEQUENCE: 6

```
Met Ile Val Glu Gly Ser Asp Ala Glu Ile Gly Met Ser Pro Trp Gln
1               5                   10                  15

Val Met Leu Phe Arg Lys Ser Pro Gln Glu Leu Leu Cys Gly Ala Ser
            20                  25                  30

Leu Ile Ser Asp Arg Trp Val Leu Thr Ala Ala His Cys Leu Leu Tyr
        35                  40                  45

Pro Pro Trp Asp Lys Asn Phe Thr Glu Asn Asp Leu Leu Val Arg Ile
    50                  55                  60

Gly Lys His Ser Arg Thr Arg Tyr Glu Arg Asn Ile Glu Lys Ile Ser
65                  70                  75                  80

Met Leu Glu Lys Ile Tyr Ile His Pro Arg Tyr Asn Trp Arg Glu Asn
                85                  90                  95

Leu Asp Arg Asp Ile Ala Leu Met Lys Leu Lys Lys Pro Val Ala Phe
            100                 105                 110

Ser Asp Tyr Ile His Pro Val Cys Leu Pro Asp Arg Glu Thr Ala Ala
        115                 120                 125

Ser Leu Leu Gln Ala Gly Tyr Lys Gly Arg Val Thr Gly Trp Gly Asn
    130                 135                 140

Leu Lys Glu Thr Trp Thr Ala Asn Val Gly Lys Gly Gln Pro Ser Val
145                 150                 155                 160

Leu Gln Val Val Asn Leu Pro Ile Val Glu Arg Pro Val Cys Lys Asp
                165                 170                 175

Ser Thr Arg Ile Arg Ile Thr Asp Asn Met Phe Cys Ala Gly Tyr Lys
            180                 185                 190

Pro Asp Glu Gly Lys Arg Gly Asp Ala Cys Glu Gly Asp Ser Gly Gly
        195                 200                 205
```

```
Pro Phe Val Met Lys Ser Pro Phe Asn Asn Arg Trp Tyr Gln Met Gly
    210                 215                 220

Ile Val Ser Ala Gly Ala Gly Cys Asp Arg Asp Gly Lys Tyr Gly Phe
225                 230                 235                 240

Tyr Thr His Val Phe Arg Leu Lys Lys Trp Ile Gln Lys Val Ile Asp
                245                 250                 255

Gln Phe Gly Glu
            260

<210> SEQ ID NO 7
<211> LENGTH: 179
<212> TYPE: DNA
<213> ORGANISM: Artificial Sequence
<220> FEATURE:
<223> OTHER INFORMATION: Optimized coding sequence for human thrombin A
      chain, with 14 amino acids added to the N-terminal end

<400> SEQUENCE: 7
gctagcagga ggaattcacc atgacggcaa cgagcgagta ccagaccttt ttcgacggta      60
gaacctttgg cagcggcgaa gcggattgcg gtctgcgtcc gctgttcgag aagaaatccc     120
tggaagataa aaccgagcgc gagttgctgg aaagctatat cgacggtcgt taagtcgac     179

<210> SEQ ID NO 8
<211> LENGTH: 50
<212> TYPE: PRT
<213> ORGANISM: Artificial Sequence
<220> FEATURE:
<223> OTHER INFORMATION: Human thrombin A chain, with 14 amino acids
      added to the N-terminal end

<400> SEQUENCE: 8

Met Thr Ala Thr Ser Glu Tyr Gln Thr Phe Phe Asp Gly Arg Thr Phe
1               5                   10                  15

Gly Ser Gly Glu Ala Asp Cys Gly Leu Arg Pro Leu Phe Glu Lys Lys
            20                  25                  30

Ser Leu Glu Asp Lys Thr Glu Arg Glu Leu Leu Glu Ser Tyr Ile Asp
        35                  40                  45

Gly Arg
    50

<210> SEQ ID NO 9
<211> LENGTH: 956
<212> TYPE: DNA
<213> ORGANISM: Artificial Sequence
<220> FEATURE:
<223> OTHER INFORMATION: Optimized coding sequence for human thrombin
      A / W215A E217A B chains (W215A E217A prethrombin-2), with 14
      amino acids added to the N-terminal end

<400> SEQUENCE: 9
gctagcagga ggaattcacc atgacggcaa ctagcgaata ccaaactttt tttgacggtc      60
gtaccttcgg cagcggcgag gctgactgtg gcctgcgccc actgtttgaa agaaaagcc     120 tggaagataa aaccgagcgt gagctgctgg agtcttacat cgacggtcgt attgttgaag    180
gttcggacgc agaaatcggt atgtcaccat ggcaagttat gttgtttcgc aaaagcccgc    240
aagagctgct gtgtggtgcc tcctgatttt ccgaccgctg gtcctgaccg cagcgcact     300 gtctgctgta tccgccgtgg gataagaatt tcaccgagaa tgacctgttg gtgcgcattg    360
gcaaacacag ccgtacgcgc tacgaacgta acatcgagaa gatcagcatg ctggagaaaa    420
tctacattca ccctcgttat aactggcgtg agaacttgga ccgtgacatc gctctgatga    480
```

```
agctgaagaa accggttgcg ttcagcgatt acattcatcc ggtttgtctg ccggatcgcg    540
agactgccgc gagcctgtta caagccggct ataagggtcg tgtaacgggc tggggtaatc    600
tgaaggaaac ctggaccgcg aatgtcggta aggtcagcc gagcgtgctg caagtggtta     660
atctgccgat tgttgaacgt ccggtctgca aggatagcac ccgcattcgt atcacggaca    720
acatgttttg cgcaggctac aagccagatg aaggcaagcg tggtgatgct gcgagggcg     780 acagcggtgg cccgtttgtg atgaaatctc cgttcaacaa ccgttggtac agatgggta    840 tcgtgagcgc gggtgcgggt tgcgaccgtg acggtaaata cggcttctat acccatgtgt    900
ttcgcctgaa aaagtggatc cagaaagtca ttgatcagtt cggcgagtaa gtcgac        956
```

<210> SEQ ID NO 10
<211> LENGTH: 309
<212> TYPE: PRT
<213> ORGANISM: Artificial Sequence
<220> FEATURE:
<223> OTHER INFORMATION: Human thrombin A / W215A E217A B chains (W215A E217A prethrombin-2), with 14 amino acids added to the N-terminal end

<400> SEQUENCE: 10

```
Met Thr Ala Thr Ser Glu Tyr Gln Thr Phe Phe Asp Gly Arg Thr Phe
 1               5                  10                  15

Gly Ser Gly Glu Ala Asp Cys Gly Leu Arg Pro Leu Phe Glu Lys Lys
             20                  25                  30

Ser Leu Glu Asp Lys Thr Glu Arg Glu Leu Leu Glu Ser Tyr Ile Asp
         35                  40                  45

Gly Arg Ile Val Glu Gly Ser Asp Ala Glu Ile Gly Met Ser Pro Trp
     50                  55                  60

Gln Val Met Leu Phe Arg Lys Ser Pro Gln Glu Leu Leu Cys Gly Ala
 65                  70                  75                  80

Ser Leu Ile Ser Asp Arg Trp Val Leu Thr Ala Ala His Cys Leu Leu
                 85                  90                  95

Tyr Pro Pro Trp Asp Lys Asn Phe Thr Glu Asn Asp Leu Leu Val Arg
            100                 105                 110

Ile Gly Lys His Ser Arg Thr Arg Tyr Glu Arg Asn Ile Glu Lys Ile
        115                 120                 125

Ser Met Leu Glu Lys Ile Tyr Ile His Pro Arg Tyr Asn Trp Arg Glu
    130                 135                 140

Asn Leu Asp Arg Asp Ile Ala Leu Met Lys Leu Lys Lys Pro Val Ala
145                 150                 155                 160

Phe Ser Asp Tyr Ile His Pro Val Cys Leu Pro Asp Arg Glu Thr Ala
                165                 170                 175

Ala Ser Leu Leu Gln Ala Gly Tyr Lys Gly Arg Val Thr Gly Trp Gly
            180                 185                 190

Asn Leu Lys Glu Thr Trp Thr Ala Asn Val Gly Lys Gly Gln Pro Ser
        195                 200                 205

Val Leu Gln Val Val Asn Leu Pro Ile Val Glu Arg Pro Val Cys Lys
    210                 215                 220

Asp Ser Thr Arg Ile Arg Ile Thr Asp Asn Met Phe Cys Ala Gly Tyr
225                 230                 235                 240

Lys Pro Asp Glu Gly Lys Arg Gly Asp Ala Cys Glu Gly Asp Ser Gly
                245                 250                 255

Gly Pro Phe Val Met Lys Ser Pro Phe Asn Asn Arg Trp Tyr Gln Met
            260                 265                 270
```

Gly Ile Val Ser Ala Gly Ala Gly Cys Asp Arg Asp Gly Lys Tyr Gly
         275                 280                 285

Phe Tyr Thr His Val Phe Arg Leu Lys Lys Trp Ile Gln Lys Val Ile
         290                 295                 300

Asp Gln Phe Gly Glu
305

<210> SEQ ID NO 11
<211> LENGTH: 1310
<212> TYPE: DNA
<213> ORGANISM: Artificial Sequence
<220> FEATURE:
<223> OTHER INFORMATION: Optimized coding sequence for mature ecarin
      from Echis carinatus (with methionine residue added to the N-
      terminal end)

<400> SEQUENCE: 11

```
gctagcagga ggaattcacc atggtcccgc cacatgaacg caaatttgag aaaaagttta     60
tcgagctggt tgttgttgtt gatcacagca tggtgacgaa atacaataac gacagcaccg    120
cgattcgtac ctggatctac gagatgctga ataccgttaa tgaaatctat ttgccgttta    180
acattagagt ggccctggtg gtctggagt tttggtgcaa cggtgatctg attaacgtta    240
cgtctaccgc ggatgatacg ctgcatagct ttggtgagtg cgtgccagc gatctgttga    300
accgcaagcg tcacgaccac gcacagctcc ttaccaacgt cactctggac cactccacgc    360
tgggcatcac cttcgtctac ggcatgtgca agtctgaccg tagcgtcgag ctgattctgg    420
actacagcaa tatcaccttt aacatggcat acattatcgc acgagatg gccatagcc      480
tgggtatgct gcacgatacc aagttctgta cgtgcggtgc gaaaccgtgc attatgttcg    540
gcaaagaaag cattccgcct ccaaaagaat ttagctcctg cagctatgat cagtataaca    600
aatacttgct gaaatacaat cctaaatgca tcctggaccc gccgttgcgt aaagacatcg    660
cgagcccggc agtctgcggt aatgaaattt gggaagaggg cgaagagtgt gattgtggta    720
gcccggctga ctgccgcaac ccgtgttgtg atgcggcgac gtgtaagctg aagccgggtg    780
ctgagtgcgg taatggtgag tgctgtgaca atgcaaaat ccgcaaagcg ggcaccgaat    840
gtcgtccggc acgtgatgat tgcgacgttg cggagcattg taccggtcag agcgcggagt    900
gcccgcgtaa tgaattccaa cgtaacggtc agccgtgcct gaataacagc ggctattgtt    960
acaatggcga ttgcccgatc atgctgaatc agtgcatcgc actgttctcc ccgtcggcta   1020
ctgttgcgca ggacagctgc ttccaacgca acttacaagg tagctactac ggttattgca   1080
ccaaagaaat tggctactat ggtaagcgct tcccgtgtgc cccgcaagac gtgaagtgtg   1140
gtcgtctgta ttgtctggac aattctttca agaagaatat gcgttgtaag aatgactata   1200
gctacgccga cgagaacaag ggcattgtgg aaccgggcac gaagtgcgag gacggtaaag   1260
tgtgcatcaa ccgtaagtgt gtggatgtca acaccgcgta ctaagtcgac               1310
```

<210> SEQ ID NO 12
<211> LENGTH: 427
<212> TYPE: PRT
<213> ORGANISM: Artificial Sequence
<220> FEATURE:
<223> OTHER INFORMATION: Mature ecarin from Echis carinatus (with
      methionine residue added to the N-terminal end)

<400> SEQUENCE: 12

Met Val Pro Pro His Glu Arg Lys Phe Glu Lys Lys Phe Ile Glu Leu
1               5                   10                  15

-continued

```
Val Val Val Val Asp His Ser Met Val Thr Lys Tyr Asn Asn Asp Ser
            20              25              30

Thr Ala Ile Arg Thr Trp Ile Tyr Glu Met Leu Asn Thr Val Asn Glu
        35              40              45

Ile Tyr Leu Pro Phe Asn Ile Arg Val Ala Leu Val Gly Leu Glu Phe
    50              55              60

Trp Cys Asn Gly Asp Leu Ile Asn Val Thr Ser Thr Ala Asp Asp Thr
65              70              75              80

Leu His Ser Phe Gly Glu Trp Arg Ala Ser Asp Leu Leu Asn Arg Lys
                85              90              95

Arg His Asp His Ala Gln Leu Leu Thr Asn Val Thr Leu Asp His Ser
            100             105             110

Thr Leu Gly Ile Thr Phe Val Tyr Gly Met Cys Lys Ser Asp Arg Ser
        115             120             125

Val Glu Leu Ile Leu Asp Tyr Ser Asn Ile Thr Phe Asn Met Ala Tyr
    130             135             140

Ile Ile Ala His Glu Met Gly His Ser Leu Gly Met Leu His Asp Thr
145             150             155             160

Lys Phe Cys Thr Cys Gly Ala Lys Pro Cys Ile Met Phe Gly Lys Glu
                165             170             175

Ser Ile Pro Pro Lys Glu Phe Ser Ser Cys Ser Tyr Asp Gln Tyr
            180             185             190

Asn Lys Tyr Leu Leu Lys Tyr Asn Pro Lys Cys Ile Leu Asp Pro Pro
        195             200             205

Leu Arg Lys Asp Ile Ala Ser Pro Ala Val Cys Gly Asn Glu Ile Trp
    210             215             220

Glu Glu Gly Glu Glu Cys Asp Cys Gly Ser Pro Ala Asp Cys Arg Asn
225             230             235             240

Pro Cys Cys Asp Ala Ala Thr Cys Lys Leu Lys Pro Gly Ala Glu Cys
                245             250             255

Gly Asn Gly Glu Cys Cys Asp Lys Cys Lys Ile Arg Lys Ala Gly Thr
            260             265             270

Glu Cys Arg Pro Ala Arg Asp Asp Cys Asp Val Ala Glu His Cys Thr
        275             280             285

Gly Gln Ser Ala Glu Cys Pro Arg Asn Glu Phe Gln Arg Asn Gly Gln
    290             295             300

Pro Cys Leu Asn Asn Ser Gly Tyr Cys Tyr Asn Gly Asp Cys Pro Ile
305             310             315             320

Met Leu Asn Gln Cys Ile Ala Leu Phe Ser Pro Ser Ala Thr Val Ala
                325             330             335

Gln Asp Ser Cys Phe Gln Arg Asn Leu Gln Gly Ser Tyr Tyr Gly Tyr
            340             345             350

Cys Thr Lys Glu Ile Gly Tyr Tyr Gly Lys Arg Phe Pro Cys Ala Pro
        355             360             365

Gln Asp Val Lys Cys Gly Arg Leu Tyr Cys Leu Asp Asn Ser Phe Lys
    370             375             380

Lys Asn Met Arg Cys Lys Asn Asp Tyr Ser Tyr Ala Asp Glu Asn Lys
385             390             395             400

Gly Ile Val Glu Pro Gly Thr Lys Cys Glu Asp Gly Lys Val Cys Ile
                405             410             415

Asn Arg Lys Cys Val Asp Val Asn Thr Ala Tyr
            420             425
```

<210> SEQ ID NO 13
<211> LENGTH: 5882
<212> TYPE: DNA
<213> ORGANISM: Artificial Sequence
<220> FEATURE:
<223> OTHER INFORMATION: pPRO33 vector

<400> SEQUENCE: 13

| | | | | | |
|---|---|---|---|---|---|
| atcgattcag | cttttcagcc | gccgccagaa | cgtcgtccgg | ctgatgccta | aataattcgc | 60 |
| cgctgctgtt | ttatcgccat | taaatttctc | cagtgcctgt | tgtggtgtca | gtaagcgtgg | 120 |
| agcgggagtt | ttcgccgact | cgcgcgccag | ttccggcagt | agcagttgca | taaactgcgg | 180 |
| cgttaaatcc | ggcgtcggtt | ccacacttaa | aaacagcgcc | agtcgttcca | tcatattgcg | 240 |
| cagttcacga | atattgcctg | gccagtcgta | gtgcagcagc | acagtttcac | ttgcctgtaa | 300 |
| cccctggcgt | aatgcagcag | aaaatggggc | ggagagcgcc | gccagagaca | ctttcaaaaa | 360 |
| gctttccgcc | agcggaagaa | tatccgccac | ccgctcgcgc | agtggtggca | attgcagacg | 420 |
| caaaatactc | agccgataaa | acagatcacg | gcgaaacgt | ccttgctgca | tatcttcttc | 480 |
| cagattgcag | tgagtggcgc | taatgacccg | tacatctacc | ggaacaggct | gatgcccgcc | 540 |
| gacgcgggtg | acctcttttt | cttccagcac | ccgcagcagc | cgggtctgca | aaggtagcgg | 600 |
| catttcgcca | atctcatcca | gaaacagcgt | accgccgtgg | gcaatttcga | acagcccggc | 660 |
| gcgacctccg | cgtcgcgagc | cggtaaacgc | cccttcctca | tagccaaaca | gttctgcttc | 720 |
| cagcagcgat | tcggcaatcg | ccccgcagtt | gacggcaaca | aacggatgcg | acttttttgcc | 780 |
| ctgtcgcgca | tcgtggcggg | caaaatattc | ccgatgaatc | gcctgggccg | ccagctcttt | 840 |
| gcccgtcccc | gtttcccct | caatcaacac | cgccgcactg | agcgggcat | acagcaaaat | 900 |
| agtctgccgt | acttgttcca | tctgtggtga | ttgaccgagc | atatcgccca | gcacgtaacg | 960 |
| agtacgcagg | gcgttgcggg | tggcatcgtg | agtgttatgg | cgtaacgaca | tgcgcgtcat | 1020 |
| atccagcgca | tcgctgaacg | cctggcgcac | ggtggcggcg | gaatagataa | aaattccggt | 1080 |
| cattccggct | tcttctgcca | aatcggtaat | cagccctgcg | ccgaccaccg | cttcggtgcc | 1140 |
| gttagctttt | agctcgttaa | tctgcccgcg | tgcgtcttcc | tcggtaatgt | agctacgttg | 1200 |
| gtcgaggcgc | aaattaaagg | tttttttgaaa | cgccaccagc | gctggaatgg | tttcctgata | 1260 |
| ggtgacaacg | ccgatagaag | aggtgagttt | tccggctttt | gccagtgcct | gtaacacatc | 1320 |
| gtagccgctc | ggtttaatca | aaataactgg | cactgacagg | cggcttttca | ggtacgcgcc | 1380 |
| gttagagcca | gccgcgatga | tggcgtcaca | gcgttcgttt | gccagtttct | tgcggatgta | 1440 |
| ggtcactgct | ttttcaaagc | caagctgaat | aggggtaatg | ttcgccaggt | gatcaaactc | 1500 |
| gaggctgata | tcgcgaaaca | gctcgaacag | gcgcgttaca | gataccgtcc | agataaccgg | 1560 |
| tttgtcgtca | ttaagccgtg | gtggatgtgc | catagcgcac | cgcaaagtta | agaaaccgaa | 1620 |
| tattgggttt | agtcttgttt | cataattgtt | gcaatgaaac | gcggtgaaac | attgcctgaa | 1680 |
| acgttaactg | aaacgcatat | ttgcggatta | gttcatgact | ttatctctaa | caaattgaaa | 1740 |
| ttaaacattt | aatttttatta | aggcaattgt | ggcacacccc | ttgctttgtc | tttatcaacg | 1800 |
| caaataacaa | gttgataaca | agctagcgaa | ttcgagctcg | gtacccgggg | atcctctaga | 1860 |
| gtcgacctgc | aggcatgcaa | gcttggctgt | tttggcggat | gagagaagat | tttcagcctg | 1920 |
| atacagatta | aatcagaacg | cagaagcggt | ctgataaaac | agaatttgcc | tggcggcagt | 1980 |
| agcgcggtgg | tcccacctga | ccccatgccg | aactcagaag | tgaaacgccg | tagcgccgat | 2040 |
| ggtagtgtgg | ggtctcccca | tgcgagagta | gggaactgcc | aggcatcaaa | taaaacgaaa | 2100 |

```
ggctcagtcg aaagactggg cctttcgttt tatctgttgt ttgtcggtga acgctctcct   2160
gagtaggaca aatccgccgg gagcggattt gaacgttgcg aagcaacggc ccggagggtg   2220
gcgggcagga cgcccgccat aaactgccag gcatcaaatt aagcagaagg ccatcctgac   2280
ggatggcctt tttgcgtttc tacaaactct tttgtttatt tttctaaata cattcaaata   2340
tgtatccgct catgagacaa taaccctgat aaatgcttca ataatattga aaaggaaga   2400
gtatgagtat tcaacatttc cgtgtcgccc ttattccctt ttttgcggca ttttgccttc   2460
ctgttttgc tcacccagaa acgctggtga agtaaaaga tgctgaagat cagttgggtg    2520
cagcaaacta ttaactggcg aactacttac tctagcttcc cggcaacaat taatagactg   2580
gatggaggcg gataaagttg caggaccact tctgcgctcg gcccttccgg ctggctggtt   2640
tattgctgat aaatctggag ccggtgagcg tgggtctcgc ggtatcattg cagcactggg   2700
gccagatggt aagccctccc gtatcgtagt tatctacacg acggggagtc aggcaactat   2760
ggatgaacga aatagacaga tcgctgagat aggtgcctca ctgattaagc attggtaact   2820
gtcagaccaa gtttactcat atatacttta gattgattta cgcgccctgt agcggcgcat   2880
taagcgcggc gggtgtggtg gttacgcgca gcgtgaccgc tacacttgcc agcgccctag   2940
cgcccgctcc tttcgctttc ttcccttcct ttctcgccac gttcgccggc tttccccgtc   3000
aagctctaaa tcggggctc cctttagggt tccgatttag tgctttacgg cacctcgacc    3060
ccaaaaaact tgatttgggt gatggttcac gtagtgggcc atcgccctga tagacggttt   3120
ttcgcccttt gacgttggag tccacgttct ttaatagtgg actcttgttc caaactggaa   3180
caacactcaa ccctatctcg ggctattctt ttgatttata agggattttg ccgatttcgg   3240
cctattggtt aaaaaatgag ctgatttaac aaaaatttaa cgcgaatttt aacaaaatat   3300
taacgtttac aatttaaaag gatctaggtg aagatccttt ttgataatct catgaccaaa   3360
atcccttaac gtgagttttc gttccactga gcgtcagacc ccgtagaaaa gatcaaagga   3420
tcttcttgag atcctttttt tctgcgcgta atctgctgct tgcaaacaaa aaaaccaccg   3480
ctaccagcgg tggtttgttt gccggatcaa gagctaccaa ctcttttcc gaaggtaact   3540
ggcttcagca gagcgcagat accaaatact gtccttctag tgtagccgta gttaggccac   3600
cacttcaaga actctgtagc accgcctaca tacctcgctc tgctaatcct gttaccagtc   3660
aggcatttga gaagcacacg gtcacactgc ttccggtagt caataaaccg gtaaaccagc   3720
aatagacata gcggctatt taacgaccct gccctgaacc gacgaccggg tcgaatttgc    3780
tttcgaattt ctgccattca tccgcttatt atcacttatt caggcgtagc aaccaggcgt   3840
ttaagggcac caataactgc cttaaaaaaa ttacgccccg ccctgccact catcgcagta   3900
ctgttgtaat tcattaagca ttctgccgac atggaagcca tcacaaacgg catgatgaac   3960
ctgaatcgcc agcggcatca gcaccttgtc gccttgcgta taatatttgc ccatggtgaa   4020
aacgggggcg aagaagttgt ccatattggc cacgtttaaa tcaaaactgg tgaaactcac   4080
ccagggattg gctgagacga aaaacatatt ctcaataaac cctttaggga ataggccag    4140
gttttcaccg taacacgcca catcttgcga atatatgtgt agaaactgcc ggaaatcgtc   4200
gtggtattca ctccagagcg atgaaaacgt ttcagtttgc tcatgaaaaa cggtgtaaca   4260
agggtgaaca ctatcccata tcaccagctc accgtctttc attgccatac ggaattccgg   4320
atgagcattc atcaggcggg caagaatgtg aataaaggcc ggataaaact tgtgcttatt   4380
tttctttacg gtctttaaaa aggccgtaat atccagctga acggtctggt tataggtaca   4440
```

| | |
|---|---:|
| ttgagcaact gactgaaatg cctcaaaatg ttctttacga tgccattggg atatatcaac | 4500 |
| ggtggtatat ccagtgattt ttttctccat tttagcttcc ttagctcctg aaaatctcga | 4560 |
| taactcaaaa aatacgcccg gtagtgatct tatttcatta tggtgaaagt tggaacctct | 4620 |
| tacgtgccga tcaacgtctc attttcgcca aaagttggcc cagggcttcc cggtatcaac | 4680 |
| agggacacca ggatttattt attctgcgaa gtgatcttcc gtcacaggta tttattcggc | 4740 |
| gcaaagtgcg tcgggtgatg ctgccaactt actgatttag tgtatgatgg tgttttgag | 4800 |
| gtgctccagt ggcttctgtt tctatcagct gtccctcctg ttcagctact gacggggtgg | 4860 |
| tgcgtaacgg caaaagcacc gccggacatc agcgctagta gcggagtgta tactggctta | 4920 |
| ctatgttggc actgatgagg gtgtcagtga agtgcttcat gtggcaggag aaaaaaggct | 4980 |
| gcaccggtgc gtcagcagaa tatgtgatac aggatatatt ccgcttcctc gctcactgac | 5040 |
| tcgctacgct cggtcgttcg actgcggcga gcggaaatgg cttacgaacg gggcggagat | 5100 |
| ttcctggaag atgccaggaa gatacttaac agggaagtga gagggccgcg gcaaagccgt | 5160 |
| ttttccatag gctccgcccc cctgacaagc atcacgaaat ctgacgctca aatcagtggt | 5220 |
| ggcgaaaccc gacaggacta taaagatacc aggcgtttcc ccctggcggc tccctcgtgc | 5280 |
| gctctcctgt tcctgccttt cggtttaccg gtgtcattcc gctgttatgg ccgcgtttgt | 5340 |
| ctcattccac gcctgacact cagttccggg taggcagttc gctccaagct ggactgtatg | 5400 |
| cacgaacccc ccgttcagtc cgaccgctgc gccttatccg gtaactatcg tcttgagtcc | 5460 |
| aacccggaaa gacatgcaaa agcaccactg gcagcagcca ctggtaattg atttagagga | 5520 |
| gttagtcttg aagtcatgcg ccggttaagg ctaaactgaa aggacaagtt ttggtgactg | 5580 |
| cgctcctcca agccagttac ctcggttcaa agagttggta gctcagagaa ccttcgaaaa | 5640 |
| accgccctgc aaggcggttt tttcgttttc agagcaagag attacgcgca gaccaaaacg | 5700 |
| atctcaagaa gatcatctta ttaatcagat aaaatatttg ctcatgagcc cgaagtggcg | 5760 |
| agcccgatct tccccatcgg tgatgtcggc gatataggcg ccagcaaccg cacctgtggc | 5820 |
| gccggtgatg ccggccacga tgcgtccggc gtagaggatc tgctcatgtt tgacagctta | 5880 |
| tc | 5882 |

<210> SEQ ID NO 14
<211> LENGTH: 5977
<212> TYPE: DNA
<213> ORGANISM: Artificial Sequence
<220> FEATURE:
<223> OTHER INFORMATION: pPRO33_A expression construct

<400> SEQUENCE: 14

| | |
|---|---:|
| atcgattcag cttttcagcc gccgccagaa cgtcgtccgg ctgatgccta aataattcgc | 60 |
| cgctgctgtt ttatcgccat taaatttctc cagtgcctgt tgtggtgtca gtaagcgtgg | 120 |
| agcgggagtt ttcgccgact cgcgcgccag ttccggcagt agcagttgca taaactgcgg | 180 |
| cgttaaatcc ggcgtcggtt ccacacttaa aaacagcgcc agtcgttcca tcatattgcg | 240 |
| cagttcacga atattgcctg ccagtcgta gtgcagcagc acagtttcac ttgcctgtaa | 300 |
| cccctggcgt aatgcagcag aaaatggggc ggagagcgcc gccagagaca ctttcaaaaa | 360 |
| gctttccgcc agcggaagaa tatccgccac ccgctcgcgc agtggtggca attgcagacg | 420 |
| caaaatactc agccgataaa acagatcacg cgaaaacgt ccttgctgca tatcttcttc | 480 |
| cagattgcag tgagtggcgc taatgacccg tacatctacc ggaacaggct gatgcccgcc | 540 |
| gacgcgggtg acctcttttt cttccagcac ccgcagcagc cgggtctgca aaggtagcgg | 600 |

```
catttcgcca atctcatcca gaaacagcgt accgccgtgg gcaatttcga acagcccggc      660
gcgacctccg cgtcgcgagc cggtaaacgc cccttcctca tagccaaaca gttctgcttc      720
cagcagcgat tcggcaatcg ccccgcagtt gacggcaaca aacggatgcg acttttttgcc    780 ctgtcgcgca tcgtggcggg caaaatattc ccgatgaatc gcctgggccg ccagctcttt      840
gcccgtcccc gtttcccccct caatcaacac cgccgcactg gagcgggcat acagcaaaat    900
agtctgccgt acttgttcca tctgtggtga ttgaccgagc atatcgccca gcacgtaacg      960
agtacgcagg gcgttgcggg tggcatcgtg agtgttatgg cgtaacgaca tgcgcgtcat     1020
atccagcgca tcgctgaacg cctggcgcac ggtggcggcg aatagataaa aaattccggt    1080
cattccggct tcttctgcca aatcggtaat cagccctgcg ccgaccaccg cttcggtgcc     1140
gttagctttt agctcgttaa tctgcccgcg tgcgtcttcc tcggtaatgt agctacgttg     1200
gtcgaggcgc aaattaaagg ttttttgaaa cgccaccagc gctggaatgg tttcctgata    1260
ggtgacaacg ccgatagaag aggtgagttt tccggcttt gccagtgcct gtaacacatc      1320
gtagccgctc ggtttaatca aaataactgg cactgacagg cggcttttca ggtacgcgcc     1380
gttagagcca gccgcgatga tggcgtcaca gcgttcgttt gccagtttct tgcggatgta    1440
ggtcactgct ttttcaaagc caagctgaat aggggtaatg ttcgccaggt gatcaaactc    1500
gaggctgata tcgcgaaaca gctcgaacag gcgcgttaca gataccgtcc agataaccgg   1560
tttgtcgtca ttaagccgtg gtggatgtgc catagcgcac cgcaaagtta agaaaccgaa     1620
tattgggttt agtcttgttt cataattgtt gcaatgaaac gcggtgaaac attgcctgaa    1680
acgttaactg aaacgcatat ttgcggatta gttcatgact ttatctctaa caaattgaaa    1740
ttaaacattt aattttatta aggcaattgt ggcacacccc ttgctttgtc tttatcaacg    1800
caaataacaa gttgataaca agctagcagg aggaattcac catgacccttt ggctcgggag   1860 aggcagactg tgggctgcga cctctgttcg agaagaagtc gctggaggac aaaaccgaaa    1920
gagagctcct ggaatcctac atcgacgggc gctaagtcga cctgcaggca tgcaagcttg    1980
gctgttttgg cggatgagag aagattttca gcctgataca gattaaatca gaacgcagaa   2040
gcggtctgat aaaacagaat ttgcctggcg gcagtagcgc ggtggtccca cctgacccca   2100
tgccgaactc agaagtgaaa cgccgtagcg ccgatggtag tgtggggtct ccccatgcga    2160
gagtagggaa ctgccaggca tcaaataaaa cgaaaggctc agtcgaaaga ctgggccttt   2220
cgttttatct gttgtttgtc ggtgaacgct ctcctgagta ggacaaatcc gccgggagcg   2280
gatttgaacg ttgcgaagca acggcccgga gggtggcggg caggacgccc gccataaact    2340
gccaggcatc aaattaagca gaaggccatc ctgacggatg cctttttgc gtttctacaa    2400 actcttttgt ttattttct aaatacattc aaatatgtat ccgctcatga caataaccc     2460 ctgataaatg cttcaataat attgaaaaag gaagagtatg agtattcaac atttccgtgt    2520
cgcccttatt cccttttttg cggcattttg ccttcctgtt tttgctcacc cagaaacgct    2580
ggtgaaagta aaagatgctg aagatcagtt gggtgcagca actattaac tggcgaacta     2640 cttactctag cttcccggca acaattaata gactggatgg aggcggataa agttgcagga    2700
ccacttctgc gctcggccct tccggctggc tggtttattg ctgataaatc tggagccggt    2760
gagcgtgggt ctcgcggtat cattgcagca ctggggccag atggtaagcc ctcccgtatc    2820
gtagttatct acacgacggg gagtcaggca actatggatg aacgaaatag acagatcgct    2880
gagataggtg cctcactgat taagcattgg taactgtcag accaagttta ctcatatata    2940
```

```
ctttagattg atttacgcgc cctgtagcgg cgcattaagc gcggcgggtg tggtggttac    3000
gcgcagcgtg accgctacac ttgccagcgc cctagcgccc gctcctttcg ctttcttccc    3060
ttcctttctc gccacgttcg ccggctttcc ccgtcaagct ctaaatcggg gctcccttt    3120 agggttccga tttagtgctt tacggcacct cgaccccaaa aaacttgatt tgggtgatgg    3180
ttcacgtagt gggccatcgc cctgatagac ggttttttcgc cctttgacgt tggagtccac   3240
gttctttaat agtggactct tgttccaaac tggaacaaca ctcaacccta tctcgggcta    3300
ttcttttgat ttataaggga ttttgccgat ttcggcctat tggttaaaaa atgagctgat    3360
ttaacaaaaa tttaacgcga attttaacaa aatattaacg tttacaattt aaaaggatct    3420
aggtgaagat ccttttttgat aatctcatga ccaaaatccc ttaacgtgag ttttcgttcc    3480
actgagcgtc agaccccgta gaaaagatca aaggatcttc ttgagatcct ttttttctgc    3540
gcgtaatctg ctgcttgcaa acaaaaaaac caccgctacc agcggtggtt tgtttgccgg    3600
atcaagagct accaactctt tttccgaagg taactggctt cagcagagcg cagataccaa    3660
atactgtcct tctagtgtag ccgtagttag gccaccactt caagaactct gtagcaccgc    3720
ctacatacct cgctctgcta atcctgttac cagtcaggca tttgagaagc acacggtcac    3780
actgcttccg gtagtcaata aaccggtaaa ccagcaatag acataagcgg ctatttaacg    3840
accctgccct gaaccgacga cccgggtcgaa tttgctttcg aatttctgcc attcatccgc    3900
ttattatcac ttattcaggc gtagcaacca ggcgtttaag ggcaccaata actgccttaa    3960
aaaaattacg ccccgccctg ccactcatcg cagtactgtt gtaattcatt aagcattctg    4020
ccgacatgga agccatcaca aacggcatga tgaacctgaa tcgccagcgg catcagcacc    4080
ttgtcgcctt gcgtataata tttgcccatg gtgaaaacgg gggcgaagaa gttgtccata    4140
ttggccacgt ttaaatcaaa actggtgaaa ctcacccagg gattggctga dacgaaaaac    4200
atattctcaa taaacccttt agggaaatag gccaggtttt caccgtaaca cgccacatct    4260
tgcgaatata tgtgtagaaa ctgccggaaa tcgtcgtggt attcactcca gagcgatgaa    4320
aacgtttcag tttgctcatg gaaaacggtg taacaagggt gaacactatc ccatatcacc    4380
agctcaccgt ctttcattgc catacggaat tccggatgag cattcatcag gcgggcaaga    4440
atgtgaataa aggccggata aaacttgtgc ttatttttct ttacggtctt taaaaaggcc    4500
gtaatatcca gctgaacggt ctggttatag gtacattgag caactgactg aaatgcctca    4560
aaatgttctt tacgatgcca ttgggatata tcaacggtgg tatatccagt gatttttttc    4620
tccattttag cttccttagc tcctgaaaat ctcgataact caaaaaatac gcccggtagt    4680
gatcttattt cattatggtg aaagttggaa cctcttacgt gccgatcaac gtctcatttt    4740
cgccaaaagt tggcccaggg cttcccggta tcaacaggga caccaggatt tatttattct    4800
gcgaagtgat cttccgtcac aggtatttat tcggcgcaaa gtgcgtcggg tgatgctgcc    4860
aacttactga tttagtgtat gatggtgttt ttgaggtgct ccagtggctt ctgtttctat    4920
cagctgtccc tcctgttcag ctactgacgg ggtggtgcgt aacggcaaaa gcaccgccgg    4980
acatcagcgc tagtagcgga gtgtatactg gcttactatg ttggcactga tgagggtgtc    5040
agtgaagtgc ttcatgtggc aggagaaaaa aggctgcacc ggtgcgtcag cagaatatgt    5100
gatacaggat atattccgct tcctcgctca ctgactcgct acgctcggtc gttcgactgc    5160
ggcgagcgga atggcttac gaacggggcg gagatttcct ggaagatgcc aggaagatac    5220
ttaacaggga agtgagaggg ccgcggcaaa gccgttttc cataggctcc gcccccctga    5280
caagcatcac gaaatctgac gctcaaatca gtggtggcga aacccgacag gactataaag    5340
```

```
ataccaggcg tttccccctg gcggctccct cgtgcgctct cctgttcctg cctttcggtt    5400
taccggtgtc attccgctgt tatggccgcg tttgtctcat ccacgcctg acactcagtt     5460 ccgggtaggc agttcgctcc aagctggact gtatgcacga accccccgtt cagtccgacc    5520
gctgcgcctt atccggtaac tatcgtcttg agtccaaccc ggaaagacat gcaaaagcac    5580
cactggcagc agccactggt aattgattta gaggagttag tcttgaagtc atgcgccggt    5640
taaggctaaa ctgaaaggac aagttttggt gactgcgctc ctccaagcca gttacctcgg    5700
ttcaaagagt tggtagctca gagaaccttc gaaaaccgc cctgcaaggc ggttttttcg     5760
ttttcagagc aagagattac gcgcagacca aacgatctc aagaagatca tcttattaat     5820
cagataaaat atttgctcat gagcccgaag tggcgagccc gatcttcccc atcggtgatg    5880
tcggcgatat aggcgccagc aaccgcacct gtggcgccgg tgatgccggc cacgatgcgt    5940
ccggcgtaga ggatctgctc atgtttgaca gcttatc                             5977
```

<210> SEQ ID NO 15
<211> LENGTH: 6016
<212> TYPE: DNA
<213> ORGANISM: Artificial Sequence
<220> FEATURE:
<223> OTHER INFORMATION: pPRO33_A+ expression construct

<400> SEQUENCE: 15

```
atcgattcag cttttcagcc gccgccagaa cgtcgtccgg ctgatgccta ataattcgc       60 cgctgctgtt ttatcgccat taaatttctc cagtgcctgt tgtggtgtca gtaagcgtgg    120
agcgggagtt ttcgccgact cgcgcgccag ttccggcagt agcagttgca taaactgcgg    180
cgttaaatcc ggcgtcggtt ccacacttaa aaacagcgcc agtcgttcca tcatattgcg    240
cagttcacga atattgcctg ccagtcgta gtgcagcagc acagtttcac ttgcctgtaa    300
cccctggcgt aatgcagcag aaaatggggc ggagagcgcc gccagagaca ctttcaaaaa    360
gctttccgcc agcggaagaa tatccgccac ccgctcgcgc agtggtggca attgcagacg    420
caaaatactc agccgataaa acagatcacg gcgaaaacgt ccttgctgca tatcttcttc    480
cagattgcag tgagtggcgc taatgacccg tacatctacc ggaacaggct gatgcccgcc    540
gacgcgggtg acctcttttt cttccagcac ccgcagcagc cgggtctgca aaggtagcgg    600
catttcgcca atctcatcca gaaacagcgt accgccgtgg caatttcga acagcccggc    660 gcgacctccg cgtcgcgagc cggtaaacgc cccttcctca tagccaaaca gttctgcttc    720
cagcagcgat tcggcaatcg ccccgcagtt gacggcaaca aacggatgcg acttttttgcc    780 ctgtcgcgca tcgtggcggg caaaatattc ccgatgaatc gcctgggccg ccagctcttt    840
gcccgtcccc gtttccccct caatcaacac cgccgcactg gagcgggcat acagcaaaat    900
agtctgccgt acttgttcca tctgtggtga ttgaccgagc atatcgccca gcacgtaacg    960
agtacgcagg cgttgcggg tggcatcgtg agtgttatgg cgtaacgaca tgcgcgtcat    1020
atccagcgca tcgctgaacg cctggcgcac ggtggcggcg aatagataa aaattccggt    1080 cattccggct tcttctgcca aatcggtaat cagccctgcg ccgaccaccg cttcggtgcc    1140
gttagctttt agctcgttaa tctgcccgcg tgcgtcttcc tcggtaatgt agctacgttg    1200
gtcgaggcgc aaattaaagg ttttttgaaa cgccaccagc gctggaatgg tttcctgata    1260
ggtgacaacg ccgatagaag aggtgagttt tccggctttt gccagtgcct gtaacacatc    1320
gtagccgctc ggtttaatca aaataactgg cactgacagg cggcttttca ggtacgcgcc    1380
```

```
gttagagcca gccgcgatga tggcgtcaca gcgttcgttt gccagtttct tgcggatgta   1440
ggtcactgct ttttcaaagc caagctgaat aggggtaatg ttcgccaggt gatcaaactc   1500
gaggctgata tcgcgaaaca gctcgaacag cgcgcgttaca gataccgtcc agataaccgg  1560
tttgtcgtca ttaagccgtg gtggatgtgc catagcgcac cgcaaagtta agaaaccgaa   1620
tattgggttt agtcttgttt cataattgtt gcaatgaaac gcggtgaaac attgcctgaa   1680
acgttaactg aaacgcatat ttgcggatta gttcatgact ttatctctaa caaattgaaa   1740
ttaaacattt aattttatta aggcaattgt ggcacacccc ttgctttgtc tttatcaacg   1800
caaataacaa gttgataaca agctagcagg aggaattcac catgacggca acgagcgagt   1860
accagacctt tttcgacggt agaacctttg gcagcggcga agcggattgc ggtctgcgtc   1920
cgctgttcga agaaatcc ctggaagata aaccgagcg cgagttgctg aaagctata    1980 tcgacggtcg ttaagtcgac ctgcaggcat gcaagcttgg ctgttttggc ggatgagaga   2040
agattttcag cctgatacag attaaatcag aacgcagaag cggtctgata aaacagaatt   2100
tgcctggcgg cagtagcgcg gtggtccac ctgaccccat gccgaactca gaagtgaaac    2160
gccgtagcgc cgatggtagt gtgggtctc cccatgcgag agtagggaac tgccaggcat    2220
caaataaaac gaaaggctca gtcgaaagac tgggcctttc gttttatctg ttgtttgtcg   2280
gtgaacgctc tcctgagtag acaaatccg ccgggagcgg atttgaacgt tgcgaagcaa    2340
cggcccggag ggtggcgggc aggacgcccg ccataaactg ccaggcatca aattaagcag   2400
aaggccatcc tgacggatgg ccttttgcg tttctacaaa ctcttttgtt tattttcta     2460 aatacattca aatatgtatc cgctcatgag acaataaccc tgataaatgc ttcaataata   2520
ttgaaaaagg aagagtatga gtattcaaca tttccgtgtc gcccttattc cctttttgc    2580 ggcatttgc cttcctgttt ttgctcaccc agaaacgctg gtgaaagtaa agatgctga     2640 agatcagttg ggtgcagcaa actattaact ggcgaactac ttactctagc ttcccggcaa   2700
caattaatag actggatgga gcggataaa gttgcaggac cacttctgcg ctcggccctt    2760
ccggctggct ggtttattgc tgataaatct ggagccggtg agcgtgggtc tcgcggtatc   2820
attgcagcac tggggccaga tggtaagccc tcccgtatcg tagttatcta cacgacgggg   2880
agtcaggcaa ctatggatga acgaaataga cagatcgctg ataggtgc ctcactgatt     2940 aagcattggt aactgtcaga ccaagtttac tcatatatac tttagattga tttacgcgcc   3000
ctgtagcggc gcattaagcg cggcgggtgt ggtggttacg cgcagcgtga ccgctacact   3060
tgccagcgcc ctagcgcccg ctcctttcgc tttcttccct tcctttctcg ccacgttcgc   3120
cggctttccc cgtcaagctc taaatcgggg gctcccttta gggttccgat ttagtgcttt   3180
acggcacctc gaccccaaaa aacttgattt gggtgatggt tcacgtagtg gccatcgcc    3240 ctgatagacg ttttttcgcc ctttgacgtt ggagtccacg ttctttaata gtggactctt   3300
gttccaaact ggaacaacac tcaaccctat ctcgggctat tcttttgatt tataagggat   3360
tttgccgatt tcggcctatt ggttaaaaaa tgagctgatt taacaaaaat ttaacgcgaa   3420
ttttaacaaa atattaacgt ttacaattta aaaggatcta ggtgaagatc cttttgata    3480 atctcatgac caaatcccct taacgtgagt ttcgttcca ctgagcgtca gacccctag     3540 aaaagatcaa aggatcttct tgagatcctt ttttctgcg cgtaatctgc tgcttgcaaa    3600
caaaaaaacc accgctacca gcggtggttt gtttgccgga tcaagagcta ccaactcttt   3660
ttccgaaggt aactggcttc agcagagcgc agataccaaa tactgtcctt ctagtgtagc   3720
cgtagttagg ccaccacttc aagaactctg tagcaccgcc tacatacctc gctctgctaa   3780
```

```
tcctgttacc agtcaggcat ttgagaagca cacggtcaca ctgcttccgg tagtcaataa    3840
accggtaaac cagcaataga cataagcggc tatttaacga ccctgccctg aaccgacgac    3900
cgggtcgaat ttgctttcga atttctgcca ttcatccgct tattatcact tattcaggcg    3960
tagcaaccag gcgtttaagg gcaccaataa ctgccttaaa aaaattacgc cccgccctgc    4020
cactcatcgc agtactgttg taattcatta agcattctgc cgacatggaa gccatcacaa    4080
acggcatgat gaacctgaat cgccagcggc atcagcacct tgtcgccttg cgtataatat    4140
ttgcccatgg tgaaaacggg ggcgaagaag ttgtccatat tggccacgtt aaatcaaaa     4200 ctggtgaaac tcacccaggg attggctgag acgaaaaaca tattctcaat aaaccctta    4260 gggaaatagg ccaggttttc accgtaacac gccacatctt gcgaatatat gtgtagaaac    4320
tgccggaaat cgtcgtggta ttcactccag agcgatgaaa acgtttcagt ttgctcatgg    4380
aaaacggtgt aacaagggtg aacactatcc catatcacca gctcaccgtc tttcattgcc    4440
atacggaatt ccggatgagc attcatcagg cgggcaagaa tgtgaataaa ggccggataa    4500
aacttgtgct tattttttctt tacggtctttt aaaaaggccg taatatccag ctgaacggtc    4560
tggttatagg tacattgagc aactgactga atgcctcaa aatgttcttt acgatgccat      4620
tgggatatat caacggtggt atatccagtg attttttttct ccattttagc ttccttagct    4680
cctgaaaatc tcgataactc aaaaaatacg cccggtagtg atcttatttc attatggtga    4740
aagttggaac ctcttacgtg ccgatcaacg tctcattttc gccaaaagtt ggcccagggc    4800
ttcccggtat caacagggac accaggattt atttattctg cgaagtgatc ttccgtcaca    4860
ggtatttatt cggcgcaaag tgcgtcgggt gatgctgcca acttactgat ttagtgtatg    4920
atggtgtttt tgaggtgctc cagtggcttc tgtttctatc agctgtccct cctgttcagc    4980
tactgacggg gtggtgcgta acggcaaaag caccgccgga catcagcgct agtagcggag    5040
tgtatactgg cttactatgt tggcactgat gagggtgtca gtgaagtgct tcatgtggca    5100
ggagaaaaaa ggctgcaccg gtgcgtcagc agaatatgtg atacaggata tattccgctt    5160
cctcgctcac tgactcgcta cgctcggtcg ttcgactgcg gcgagcggaa atggcttacg    5220 aacgggggcgg agatttcctg gaagatgcca ggaagatact taacagggaa gtgagagggc    5280
cgcggcaaag ccgtttttcc ataggctccg ccccccttgac aagcatcacg aaatctgacg    5340
ctcaaatcag tggtggcgaa acccgacagg actataaaga taccaggcgt ttccccctgg    5400
cggctccctc gtgcgctctc ctgttcctgc ctttcggttt accggtgtca ttccgctgtt    5460
atggccgcgt ttgtctcatt ccacgcctga cactcagttc cgggtaggca gttcgctcca    5520
agctggactg tatgcacgaa ccccccgttc agtccgaccg ctgcgcctta tccggtaact    5580
atcgtcttga gtccaacccg gaagacatg caaaagcacc actggcagca gccactggta    5640
attgatttag aggagttagt cttgaagtca tgcgccggtt aaggctaaac tgaaaggaca    5700
agttttggtg actgcgctcc tccaagccag ttacctcggt tcaaagagtt ggtagctcag    5760
agaaccttcg aaaaaccgcc ctgcaaggcg ttttttcgt tttcagagca agagattacg    5820
cgcagaccaa aacgatctca agaagatcat cttattaatc agataaaata tttgctcatg    5880
agcccgaagt ggcgagcccg atcttcccca tcggtgatgt cggcgatata ggcgccagca    5940
accgcacctg tggcgccggt gatgccggcc acgatgcgtc cggcgtagag gatctgctca    6000
tgtttgacag cttatc                                                    6016
```

<210> SEQ ID NO 16

<211> LENGTH: 5302
<212> TYPE: DNA
<213> ORGANISM: Artificial Sequence
<220> FEATURE:
<223> OTHER INFORMATION: pBAD_WE-B expression construct

<400> SEQUENCE: 16

| | | | | | |
|---|---|---|---|---|---|
| atcgatgcat | aatgtgcctg | tcaaatggac | gaagcaggga | ttctgcaaac | cctatgctac | 60 |
| tccgtcaagc | cgtcaattgt | ctgattcgtt | accaattatg | acaacttgac | ggctacatca | 120 |
| ttcactttt | cttcacaacc | ggcacggaac | tcgctcgggc | tggccccggt | gcattttta | 180 |
| aatacccgcg | agaaatagag | ttgatcgtca | aaccaacat | tgcgaccgac | ggtggcgata | 240 |
| ggcatccggg | tggtgctcaa | aagcagcttc | gcctggctga | tacgttggtc | ctcgcgccag | 300 |
| cttaagacgc | taatccctaa | ctgctggcgg | aaaagatgtg | acagacgcga | cggcgacaag | 360 |
| caaacatgct | gtgcgacgct | ggcgatatca | aaattgctgt | ctgccaggtg | atcgctgatg | 420 |
| tactgacaag | cctcgcgtac | ccgattatcc | atcggtggat | ggagcgactc | gttaatcgct | 480 |
| tccatgcgcc | gcagtaacaa | ttgctcaagc | agatttatcg | ccagcagctc | cgaatagcgc | 540 |
| ccttccctt | gcccggcgtt | aatgatttgc | ccaaacaggt | cgctgaaatg | cggctggtgc | 600 |
| gcttcatccg | ggcgaaagaa | ccccgtattg | gcaaatattg | acggccagtt | aagccattca | 660 |
| tgccagtagg | cgcgcggacg | aaagtaaacc | cactggtgat | accattcgcg | agcctccgga | 720 |
| tgacgaccgt | agtgatgaat | ctctcctggc | gggaacagca | aaatatcacc | cggtcggcaa | 780 |
| acaaattctc | gtccctgatt | tttcaccacc | ccctgaccgc | gaatggtgag | attgagaata | 840 |
| taaccttca | ttcccagcgg | tcggtcgata | aaaaatcga | gataaccgtt | ggcctcaatc | 900 |
| ggcgttaaac | ccgccaccag | atgggcatta | acgagtatc | ccggcagcag | gggatcattt | 960 |
| tgcgcttcag | ccatactttt | catactcccg | ccattcagag | aagaaaccaa | ttgtccatat | 1020 |
| tgcatcagac | attgccgtca | ctgcgtcttt | tactggctct | tctcgctaac | caaaccggta | 1080 |
| accccgctta | ttaaaagcat | tctgtaacaa | agcgggacca | aagccatgac | aaaaacgcgt | 1140 |
| aacaaaagtg | tctataatca | cggcagaaaa | gtccacattg | attatttgca | cggcgtcaca | 1200 |
| ctttgctatg | ccatagcatt | tttatccata | agattagcgg | atcctacctg | acgctttta | 1260 |
| tcgcaactct | ctactgtttc | tccataccg | tttttttggg | ctagcaggag | gaattcacca | 1320 |
| tgattgttga | aggttcggac | gcagaaatcg | gtatgtcacc | atggcaagtt | atgttgtttc | 1380 |
| gcaaaagccc | gcaagagctg | ctgtgtggtg | cctccctgat | ttccgaccgc | tgggtcctga | 1440 |
| ccgcagcgca | ctgtctgctg | tatccgccgt | gggataagaa | tttcaccgag | aatgacctgt | 1500 |
| tggtgcgcat | tggcaaacac | agccgtacgc | gctacgaacg | taacatcgag | aagatcagca | 1560 |
| tgctggagaa | aatctacatt | caccctcgtt | ataactggcg | tgagaacttg | gaccgtgaca | 1620 |
| tcgctctgat | gaagctgaag | aaaccggttg | cgttcagcga | ttacattcat | ccggtttgtc | 1680 |
| tgccggatcg | cgagactgcc | gcgagccgt | tacaagccgg | ctataagggt | cgtgtaacgg | 1740 |
| gctgggtaa | tctgaaggaa | acctggaccg | cgaatgtcgg | taaaggtcag | ccgagcgtgc | 1800 |
| tgcaagtggt | taatctgccg | attgttgaac | gtccggtctg | caaggatagc | acccgcattc | 1860 |
| gtatcacgga | caacatgttt | tgcgcaggct | acaagccaga | tgaaggcaag | cgtggtgatg | 1920 |
| cttgcgaggg | cgacagcggt | ggcccgtttg | tgatgaaatc | tccgttcaac | aaccgttggt | 1980 |
| accagatggg | tatcgtgagc | gcgggtgcgg | gttgcgaccg | tgacggtaaa | tacggcttct | 2040 |
| atacccatgt | gtttcgcctg | aaaaagtgga | tccagaaagt | cattgatcag | ttcggcgagt | 2100 |
| aagtcgacct | gcaggcatgc | aagcttggct | gttttggcgg | atgagagaag | atttcagcc | 2160 |

```
tgatacagat taaatcagaa cgcagaagcg gtctgataaa acagaatttg cctggcggca    2220
gtagcgcggt ggtcccacct gacccatgc cgaactcaga agtgaaacgc cgtagcgccg     2280
atggtagtgt ggggtctccc catgcgagag tagggaactg ccaggcatca aataaaacga    2340
aaggctcagt cgaaagactg ggcctttcgt tttatctgtt gtttgtcggt gaacgctctc    2400
ctgagtagga caaatccgcc gggagcggat ttgaacgttg cgaagcaacg gcccggaggg    2460
tggcgggcag gacgcccgcc ataaactgcc aggcatcaaa ttaagcagaa ggccatcctg    2520
acggatggcc ttttgcgtt tctacaaact cttttgttta ttttctaaa tacattcaaa      2580 tatgtatccg ctcatgagac aataaccctg ataaatgctt caataatatt gaaaaggaa     2640 gagtatgagt attcaacatt tccgtgtcgc ccttattccc ttttttgcgg cattttgcct    2700
tcctgttttt gctcacccag aaacgctggt gaaagtaaaa gatgctgaag atcagttggg    2760
tgcacgagtg ggttacatcg aactggatct caacagcggt aagatccttg agagttttcg    2820
ccccgaagaa cgttttccaa tgatgagcac ttttaaagtt ctgctatgtg gcgcggtatt    2880
atcccgtgtt gacgccgggc aagagcaact cggtcgccgc atacactatt ctcagaatga    2940
cttggttgag tactcaccag tcacagaaaa gcatcttacg gatggcatga cagtaagaga    3000
attatgcagt gctgccataa ccatgagtga taacactgcg gccaacttac ttctgacaac    3060
gatcggagga ccgaaggagc taaccgcttt tttgcacaac atgggggatc atgtaactcg    3120
ccttgatcgt tgggaaccgg agctgaatga agccatacca aacgacgagc gtgacaccac    3180
gatgcctgta gcaatggcaa caacgttgcg caaactatta actggcgaac tacttactct    3240
agcttcccgg caacaattaa tagactggat ggaggcggat aaagttgcag gaccacttct    3300
gcgctcggcc cttccggctg gctggtttat tgctgataaa tctggagccg gtgagcgtgg    3360
gtctcgcggt atcattgcag cactggggcc agatggtaag ccctcccgta tcgtagttat    3420
ctacacgacg gggagtcagg caactatgga tgaacgaaat agacagatcg ctgagatagg    3480
tgcctcactg attaagcatt ggtaactgtc agaccaagtt tactcatata ctttagat     3540 tgatttacgc gccctgtagc ggcgcattaa gcgcggcggg tgtggtggtt acgcgcagcg    3600
tgaccgctac acttgccagc gccctagcgc ccgctccttt cgctttcttc ccttcctttc    3660
tcgccacgtt cgccggcttt ccccgtcaag ctctaaatcg ggggctccct ttagggttcc    3720
gatttagtgc tttacggcac ctcgacccca aaaaacttga tttgggtgat ggttcacgta    3780
gtgggccatc gccctgatag acggttttc gccctttgac gttggagtcc acgttcttta    3840
atagtggact cttgttccaa acttgaacaa cactcaaccc tatctcgggc tattcttttg    3900
atttataagg gattttgccg atttcggcct attggttaaa aaatgagctg atttaacaaa    3960
aatttaacgc gaattttaac aaaatattaa cgtttacaat ttaaaaggat ctaggtgaag    4020
atcctttttg ataatctcat gaccaaaatc ccttaacgtg agttttcgtt ccactgagcg    4080
tcagaccccg tagaaaagat caaaggatct tcttgagatc ctttttttct gcgcgtaatc    4140
tgctgcttgc aaacaaaaaa accaccgcta ccagcggtgg tttgtttgcc ggatcaagag    4200
ctaccaactc tttttccgaa ggtaactggc ttcagcagag cgcagatacc aaatactgtc    4260
cttctagtgt agccgtagtt aggccaccac ttcaagaact ctgtagcacc gcctacatac    4320
ctcgctctgc taatcctgtt accagtggct gctgccagtg gcgataagtc gtgtcttacc    4380
gggttggact caagacgata gttaccggat aaggcgcagc ggtcgggctg aacggggggt    4440
tcgtgcacac agcccagctt ggagcgaacg acctacaccg aactgagata cctacagcgt    4500
```

```
gagctatgag aaagcgccac gcttcccgaa gggagaaagg cggacaggta tccggtaagc    4560
ggcagggtcg gaacaggaga gcgcacgagg gagcttccag ggggaaacgc ctggtatctt    4620
tatagtcctg tcgggtttcg ccacctctga cttgagcgtc gattttgtg atgctcgtca    4680 gggggggcgga gcctatggaa aaacgccagc aacgcggcct ttttacggtt cctggccttt    4740
tgctggcctt ttgctcacat gttctttcct gcgttatccc ctgattctgt ggataaccgt    4800
attaccgcct ttgagtgagc tgataccgct cgccgcagcc gaacgaccga gcgcagcgag    4860
tcagtgagcg aggaagcgga agagcgcctg atgcggtatt ttctccttac gcatctgtgc    4920
ggtatttcac accgcatagg gtcatggctg cgccccgaca cccgccaaca cccgctgacg    4980
cgccctgacg ggcttgtctg ctcccggcat ccgcttacag acaagctgtg accgtctccg    5040
ggagctgcat gtgtcagagg ttttcaccgt catcaccgaa acgcgcgagg cagcaaggag    5100
atggcgccca acagtccccc ggccacgggg cctgccacca tacccacgcc gaaacaagcg    5160
ctcatgagcc cgaagtggcg agcccgatct tccccatcgg tgatgtcggc gatataggcg    5220
ccagcaaccg cacctgtggc gccggtgatg ccggccacga tgcgtccggc gtagaggatc    5280
tgctcatgtt tgacagctta tc                                              5302

<210> SEQ ID NO 17
<211> LENGTH: 5449
<212> TYPE: DNA
<213> ORGANISM: Artificial Sequence
<220> FEATURE:
<223> OTHER INFORMATION: pBAD_A+/WE-B expression construct

<400> SEQUENCE: 17
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120 ttcactttt cttcacaacc ggcacggaac tcgctcgggc tggccccggt gcatttttta     180
aatacccgcg agaaatagag ttgatcgtca aaaccaacat tgcgaccgac ggtggcgata     240
ggcatccggg tggtgctcaa aagcagcttc gcctggctga tacgttggtc ctcgcgccag     300
cttaagacgc taatccctaa ctgctggcgg aaaagatgtg acagacgcga cggcgacaag     360
caaacatgct gtgcgacgct ggcgatatca aaattgctgt ctgccaggtg atcgctgatg     420
tactgacaag cctcgcgtac ccgattatcc atcggtggat ggagcgactc gttaatcgct     480
tccatgcgcc gcagtaacaa ttgctcaagc agatttatcg ccagcagctc cgaatagcgc     540
ccttcccctt gccggcgtt aatgatttgc ccaaacaggt cgctgaaatg cggctggtgc     600
gcttcatccg ggcgaaagaa ccccgtattg gcaaatattg acggccagtt aagccattca     660
tgccagtagg cgcgcggacg aaagtaaacc cactggtgat accattcgcg agcctccgga     720
tgacgaccgt agtgatgaat ctctcctggc gggaacagca aaatatcacc cggtcggcaa     780
acaaattctc gtccctgatt tttcaccacc ccctgaccgc gaatggtgag attgagaata     840
taacctttca ttcccagcgg tcggtcgata aaaaatcga gataaccgtt ggcctcaatc     900
ggcgttaaac ccgccaccag atgggcatta acgagtatc ccggcagcag gggatcattt     960
tgcgcttcag ccatactttt catactcccg ccattcagaa gaaaccaa ttgtccatat    1020 tgcatcagac attgccgtca ctgcgtcttt tactggctct tctcgctaac caaaccggta    1080
accccgctta ttaaaagcat tctgtaacaa agcgggacca aagccatgac aaaaacgcgt    1140
aacaaaagtg tctataatca cggcagaaaa gtccacattg attatttgca cggcgtcaca    1200
ctttgctatg ccatagcatt tttatccata agattagcgg atcctacctg acgcttttta    1260
```

```
tcgcaactct ctactgtttc tccatacccg ttttttgggg ctagcaggag gaattcacca    1320
tgacggcaac tagcgaatac caaacttttt ttgacggtcg taccttcggc agcggcgagg    1380
ctgactgtgg cctgcgccca ctgtttgaaa agaaaagcct ggaagataaa accgagcgtg    1440
agctgctgga gtcttacatc gacggtcgta ttgttgaagg ttcggacgca gaaatcggta    1500
tgtcaccatg gcaagttatg ttgtttcgca aaagcccgca agagctgctg tgtggtgcct    1560
ccctgatttc cgaccgctgg gtcctgaccg cagcgcactg tctgctgtat ccgccgtggg    1620
ataagaattt caccgagaat gacctgttgg tgcgcattgg caaacacagc cgtacgcgct    1680
acgaacgtaa catcgagaag atcagcatgc tggagaaaat ctacattcac cctcgttata    1740
actggcgtga gaacttggac cgtgacatcg ctctgatgaa gctgaagaaa ccggttgcgt    1800
tcagcgatta cattcatccg gtttgtctgc cggatcgcga gactgccgcg agcctgttac    1860
aagccggcta aagggtcgt gtaacgggct ggggtaatct gaaggaaacc tggaccgcga    1920
atgtcggtaa aggtcagccg agcgtgctgc aagtggttaa tctgccgatt gttgaacgtc    1980
cggtctgcaa ggatagcacc cgcattcgta tcacggacaa catgttttgc gcaggctaca    2040
agccagatga aggcaagcgt ggtgatgctt gcgagggcga cagcggtggc ccgtttgtga    2100
tgaaatctcc gttcaacaac cgttggtacc agatgggtat cgtgagcgcg ggtgcgggtt    2160
gcgaccgtga cggtaaatac ggcttctata cccatgtgtt tcgcctgaaa aagtggatcc    2220
agaaagtcat tgatcagttc ggcgagtaag tcgacctgca ggcatgcaag cttggctgtt    2280
ttggcggatg agagaagatt ttcagcctga tacagattaa atcagaacgc agaagcggtc    2340
tgataaaaca gaatttgcct ggcggcagta gcgcggtggt cccacctgac cccatgccga    2400
actcagaagt gaaacgccgt agcgccgatg gtagtgtggg gtctccccat gcgagagtag    2460
ggaactgcca ggcatcaaat aaaacgaaag gctcagtcga agactgggc cttcgtttt    2520
atctgttgtt tgtcggtgaa cgctctcctg agtaggacaa atccgccggg agcggatttg    2580
aacgttgcga agcaacggcc cggagggtgg cgggcaggac gcccgccata aactgccagg    2640
catcaaatta agcagaaggc catcctgacg gatggccttt ttgcgtttct acaaactctt    2700
ttgtttattt ttctaaatac attcaaatat gtatccgctc atgagacaat aaccctgata    2760
aatgcttcaa taatattgaa aaaggaagag tatgagtatt caacatttcc gtgtcgccct    2820
tattcccttt tttgcggcat tttgccttcc tgttttgct cacccagaaa cgctggtgaa    2880
agtaaaagat gctgaagatc agttgggtgc acgagtgggt tacatcgaac tggatctcaa    2940
cagcggtaag atccttgaga gttttcgccc cgaagaacgt tttccaatga tgagcacttt    3000
taaagttctg ctatgtggcg cggtattatc ccgtgttgac gccgggcaag agcaactcgg    3060
tcgccgcata cactattctc agaatgactt ggttgagtac tcaccagtca cagaaaagca    3120
tcttacggat ggcatgacag taagagaatt atgcagtgct gccataacca tgagtgataa    3180
cactgcggcc aacttacttc tgacaacgat cggaggaccg aaggagctaa ccgcttttt    3240
gcacaacatg ggggatcatg taactcgcct tgatcgttgg gaaccggagc tgaatgaagc    3300
cataccaaac gacgagcgtg acaccacgat gcctgtagca atggcaacaa cgttgcgcaa    3360
actattaact ggcgaactac ttactctagc ttcccggcaa caattaatag actggatgga    3420
ggcggataaa gttgcaggac cacttctgcg ctcggccctt ccggctggct ggtttattgc    3480
tgataaatct ggagccggtg agcgtgggtc tcgcggtatc attgcagcac tggggccaga    3540
tggtaagccc tcccgtatcg tagttatcta cacgacgggg agtcaggcaa ctatggatga    3600
```

```
acgaaataga cagatcgctg agataggtgc ctcactgatt aagcattggt aactgtcaga    3660
ccaagtttac tcatatatac tttagattga tttacgcgcc ctgtagcggc gcattaagcg    3720
cggcgggtgt ggtggttacg cgcagcgtga ccgctacact tgccagcgcc ctagcgcccg    3780
ctcctttcgc tttcttccct ccctttctcg ccacgttcgc cggctttccc cgtcaagctc    3840
taaatcgggg gctcccttta gggttccgat ttagtgcttt acggcacctc gaccccaaaa    3900
aacttgattt gggtgatggt tcacgtagtg ggccatcgcc ctgatagacg ttttttcgcc    3960
ctttgacgtt ggagtccacg ttctttaata gtggactctt gttccaaact tgaacaacac    4020
tcaaccctat ctcgggctat tcttttgatt tataagggat tttgccgatt tcggcctatt    4080
ggttaaaaaa tgagctgatt taacaaaaat ttaacgcgaa ttttaacaaa atattaacgt    4140
ttacaattta aaaggatcta ggtgaagatc cttttttgata atctcatgac caaaatccct    4200
taacgtgagt tttcgttcca ctgagcgtca gaccccgtag aaaagatcaa aggatcttct    4260
tgagatcctt ttttttctgcg cgtaatctgc tgcttgcaaa caaaaaaacc accgctacca    4320
gcggtggttt gtttgccgga tcaagagcta ccaactcttt ttccgaaggt aactggcttc    4380
agcagagcgc agataccaaa tactgtcctt ctagtgtagc cgtagttagg ccaccacttc    4440
aagaactctg tagcaccgcc tacatacctc gctctgctaa tcctgttacc agtggctgct    4500
gccagtggcg ataagtcgtg tcttaccggg ttggactcaa gacgatagtt accggataag    4560
gcgcagcggt cgggctgaac ggggggttcg tgcacacagc ccagcttgga gcgaacgacc    4620
tacaccgaac tgagatacct acagcgtgag ctatgagaaa gcgccacgct tcccgaaggg    4680
agaaaggcgg acaggtatcc ggtaagcggc agggtcggaa caggagagcg cacgagggag    4740
cttccagggg gaaacgcctg gtatctttat agtcctgtcg ggtttcgcca cctctgactt    4800
gagcgtcgat ttttgtgatg ctcgtcaggg gggcggagcc tatggaaaaa cgccagcaac    4860
gcggcctttt tacggttcct ggccttttgc tggccttttg ctcacatgtt ctttcctgcg    4920
ttatcccctg attctgtgga taaccgtatt accgcctttg agtgagctga taccgctcgc    4980
cgcagccgaa cgaccgagcg cagcgagtca gtgagcgagg aagcggaaga gcgcctgatg    5040
cggtattttc tccttacgca tctgtgcggt atttcacacc gcatagggtc atggctgcgc    5100
cccgacaccc gccaacaccc gctgacgcgc cctgacgggc ttgtctgctc ccggcatccg    5160
cttacagaca agctgtgacc gtctccggga gctgcatgtg tcagaggttt tcaccgtcat    5220
caccgaaacg cgcgaggcag caaggagatg gcgcccaaca gtcccccggc cacggggcct    5280
gccaccatac ccacgccgaa acaagcgctc atgagcccga agtggcgagc ccgatcttcc    5340
ccatcggtga tgtcggcgat ataggcgcca gcaaccgcac ctgtggcgcc ggtgatgccg    5400
gccacgatgc gtccggcgta gaggatctgc tcatgtttga cagcttatc                5449
```

<210> SEQ ID NO 18
<211> LENGTH: 7147
<212> TYPE: DNA
<213> ORGANISM: Artificial Sequence
<220> FEATURE:
<223> OTHER INFORMATION: pPRO33_ecarin expression construct

<400> SEQUENCE: 18

```
atcgattcag cttttcagcc gccgccagaa cgtcgtccgg ctgatgccta aataattcgc      60
cgctgctgtt ttatcgccat taaatttctc cagtgcctgt tgtggtgtca gtaagcgtgg     120
agcgggagtt ttcgccgact cgcgcgccag ttccggcagt agcagttgca taaactgcgg     180
cgttaaatcc ggcgtcggtt ccacacttaa aaacagcgcc agtcgttcca tcatattgcg     240
```

```
cagttcacga atattgcctg gccagtcgta gtgcagcagc acagtttcac ttgcctgtaa        300
cccctggcgt aatgcagcag aaaatggggc ggagagcgcc gccagagaca ctttcaaaaa        360
gctttccgcc agcggaagaa tatccgccac ccgctcgcgc agtggtggca attgcagacg        420
caaaatactc agccgataaa acagatcacg gcgaaaacgt ccttgctgca tatcttcttc        480
cagattgcag tgagtggcgc taatgacccg tacatctacc ggaacaggct gatgcccgcc        540
gacgcgggtg acctcttttt cttccagcac ccgcagcagc cgggtctgca aaggtagcgg        600
catttcgcca atctcatcca gaaacagcgt accgccgtgg gcaatttcga acagcccggc        660
gcgacctccg cgtcgcgagc cggtaaacgc cccttcctca tagccaaaca gttctgcttc        720
cagcagcgat tcggcaatcg ccccgcagtt gacggcaaca aacggatgcg acttttttgcc       780 ctgtcgcgca tcgtggcggg caaaatattc ccgatgaatc gcctgggccg ccagctcttt        840
gcccgtcccc gtttccccct caatcaacac cgccgcactg gagcgggcat acagcaaaat        900
agtctgccgt acttgttcca tctgtggtga ttgaccgagc atatcgccca gcacgtaacg        960
agtacgcagg gcgttgcggg tggcatcgtg agtgttatgg cgtaacgaca tgcgcgtcat       1020
atccagcgca tcgctgaacg cctggcgcac ggtggcggcg aatagataaa aaattccggt       1080
cattccggct tcttctgcca aatcggtaat cagccctgcg ccgaccaccg cttcggtgcc       1140
gttagctttt agctcgttaa tctgcccgcg tgcgtcttcc tcggtaatgt agctacgttg       1200
gtcgaggcgc aaattaaagg ttttttgaaa cgccaccagc gctggaatgg tttcctgata       1260
ggtgacaacg ccgatagaag aggtgagttt tccggctttt gccagtgcct gtaacacatc       1320
gtagccgctc ggtttaatca aaataactgg cactgacagg cggcttttca ggtacgcgcc       1380
gttagagcca gccgcgatga tggcgtcaca gcgttcgttt gccagtttct tgcggatgta       1440
ggtcactgct ttttcaaagc caagctgaat aggggtaatg ttcgccaggt gatcaaactc       1500
gaggctgata tcgcgaaaca gctcgaacag gcgcgttaca gataccgtcc agataaccgg       1560
tttgtcgtca ttaagccgtg gtggatgtgc catagcgcac cgcaaagtta agaaaccgaa       1620
tattgggttt agtcttgttt cataattgtt gcaatgaaac gcggtgaaac attgcctgaa       1680
acgttaactg aaacgcatat ttgcggatta gttcatgact ttatctctaa caaattgaaa       1740
ttaaacattt aatttttatta aggcaattgt ggcacacccc ttgctttgtc tttatcaacg       1800
caaataacaa gttgataaca agctagcagg aggaattcac catggtcccg ccacatgaac       1860
gcaaatttga gaaaagttt atcgagctgg ttgttgttgt tgatcacagc atggtgacga       1920
aatacaataa cgacagcacc gcgattcgta cctggatcta cgagatgctg aataccgtta       1980
atgaaatcta tttgccgttt aacattagag tggccctggt gggtctggag ttttggtgca       2040
acggtgatct gattaacgtt acgtctaccg cggatgatac gctgcatagc tttggtgagt       2100
ggcgtgccag cgatctgttg aaccgcaagc gtcacgacca cgcacagctc cttaccaacg       2160
tcactctgga ccactccacg ctgggcatca ccttcgtcta cggcatgtgc aagtctgacc       2220
gtagcgtcga gctgattctg gactacagca atatcacctt taacatggca tacattatcg       2280
cacacgagat gggccatagc ctgggtatgc tgcacgatac caagttctgt acgtgcggtg       2340
cgaaaccgtg cattatgttc ggcaaagaaa gcattccgcc tccaaaagaa tttagctcct       2400
gcagctatga tcagtataac aaatacttgc tgaaatacaa tcctaaatgc atcctggacc       2460
cgccgttgcg taaagacatc gcgagcccgg cagtctgcgg taatgaaatt tgggaagagg       2520
gcgaagagtg tgattgtggt agcccggctg actgccgcaa cccgtgttgt gatgcggcga       2580
```

```
cgtgtaagct gaagccgggt gctgagtgcg gtaatggtga gtgctgtgac aaatgcaaaa    2640
tccgcaaagc gggcaccgaa tgtcgtccgg cacgtgatga ttgcgacgtt gcggagcatt    2700
gtaccggtca gagcgcggag tgcccgcgta atgaattcca acgtaacggt cagccgtgcc    2760
tgaataacag cggctattgt tacaatggcg attgcccgat catgctgaat cagtgcatcg    2820
cactgttctc cccgtcggct actgttgcgc aggacagctg cttccaacgc aacttacaag    2880
gtagctacta cggttattgc accaaagaaa ttggctacta tggtaagcgc ttcccgtgtg    2940
ccccgcaaga cgtgaagtgt ggtcgtctgt attgtctgga caattctttc aagaagaata    3000
tgcgttgtaa gaatgactat agctacgccg acgagaacaa gggcattgtg aaccgggca    3060
cgaagtgcga ggacggtaaa gtgtgcatca accgtaagtg tgtggatgtc aacaccgcgt    3120
actaagtcga cctgcaggca tgcaagcttg gctgttttgg cggatgagag aagattttca    3180
gcctgataca gattaaatca gaacgcagaa gcggtctgat aaaacagaat ttgcctggcg    3240
gcagtagcgc ggtggtccca cctgacccca tgccgaactc agaagtgaaa cgccgtagcg    3300
ccgatggtag tgtggggtct ccccatgcga gagtagggaa ctgccaggca tcaaataaaa    3360
cgaaaggctc agtcgaaaga ctgggccttt cgttttatct gttgtttgtc ggtgaacgct    3420
ctcctgagta ggacaaatcc gccggggagcg gatttgaacg ttgcgaagca acggcccgga    3480
gggtggcggg caggacgccc gccataaact gccaggcatc aaattaagca gaaggccatc    3540
ctgacggatg cccttttgc gtttctacaa actcttttgt ttatttttct aaatacattc    3600
aaatatgtat ccgctcatga gacaataacc ctgataaatg cttcaataat attgaaaaag    3660
gaagagtatg agtattcaac atttccgtgt cgcccttatt ccctttttg cggcattttg    3720
ccttcctgtt tttgctcacc cagaaacgct ggtgaaagta aaagatgctg aagatcagtt    3780
gggtgcagca actattaac tggcgaacta cttactctag cttcccggca acaattaata    3840
gactggatgg aggcggataa agttgcagga ccacttctgc gctcggccct tccggctggc    3900
tggtttattg ctgataaatc tggagccggt gagcgtgggt ctcgcggtat cattgcagca    3960
ctggggccag atggtaagcc ctcccgtatc gtagttatct acacgacggg gagtcaggca    4020
actatggatg aacgaaatag acagatcgct gagataggtg cctcactgat taagcattgg    4080
taactgtcag accaagttta ctcatatata ctttagattg atttacgcgc cctgtagcgg    4140
cgcattaagc gcggcgggtg tggtggttac gcgcagcgtg accgctacac ttgccagcgc    4200
cctagcgccc gctcctttcg ctttcttccc ttcctttctc gccacgttcg ccggctttcc    4260
ccgtcaagct ctaaatcggg ggctcccttt agggttccga tttagtgctt tacggcacct    4320
cgaccccaaa aaacttgatt tgggtgatgg ttcacgtagt gggccatcgc cctgatagac    4380
ggtttttcgc cctttgacgt tggagtccac gttctttaat agtggactct tgttccaaac    4440
tggaacaaca ctcaacccta tctcgggcta ttcttttgat ttataaggga ttttgccgat    4500
ttcggcctat tggttaaaaa atgagctgat ttaacaaaaa tttaacgcga attttaacaa    4560
aatattaacg tttacaattt aaaaggatct aggtgaagat cctttttgat aatctcatga    4620
ccaaaatccc ttaacgtgag ttttcgttcc actgagcgtc agaccccgta gaaaagatca    4680
aaggatcttc ttgagatcct ttttttctgc gcgtaatctg ctgcttgcaa acaaaaaaac    4740
caccgctacc agcggtggtt tgtttgccgg atcaagagct accaactctt tttccgaagg    4800
taactggctt cagcagagcg cagataccaa atactgtcct tctagtgtag ccgtagttag    4860
gccaccactt caagaactct gtagcaccgc ctacatacct cgctctgcta atcctgttac    4920
cagtcaggca tttgagaagc acacggtcac actgcttccg gtagtcaata aaccggtaaa    4980
```

```
ccagcaatag acataagcgg ctatttaacg accctgccct gaaccgacga ccgggtcgaa    5040
tttgctttcg aatttctgcc attcatccgc ttattatcac ttattcaggc gtagcaacca    5100
ggcgtttaag ggcaccaata actgccttaa aaaaattacg ccccgccctg ccactcatcg    5160
cagtactgtt gtaattcatt aagcattctg ccgacatgga agccatcaca acggcatga    5220
tgaacctgaa tcgccagcgg catcagcacc ttgtcgcctt gcgtataata tttgcccatg    5280
gtgaaaacgg gggcgaagaa gttgtccata ttggccacgt ttaaatcaaa actggtgaaa    5340
ctcacccagg gattggctga gacgaaaaac atattctcaa taaacccttt agggaaatag    5400
gccaggtttt caccgtaaca cgccacatct tgcgaatata tgtgtagaaa ctgccggaaa    5460
tcgtcgtggt attcactcca gagcgatgaa aacgtttcag tttgctcatg gaaaacggtg    5520
taacaagggt gaacactatc ccatatcacc agctcaccgt ctttcattgc catacggaat    5580
tccggatgag cattcatcag gcgggcaaga atgtgaataa aggccggata aaacttgtgc    5640
ttatttttct ttacggtctt taaaaaggcc gtaatatcca gctgaacggt ctggttatag    5700
gtacattgag caactgactg aaatgcctca aaatgttctt tacgatgcca ttgggatata    5760
tcaacggtgg tatatccagt gattttttc tccattttag cttccttagc tcctgaaaat    5820
ctcgataact caaaaaatac gcccggtagt gatcttattt cattatggtg aaagttggaa    5880
cctcttacgt gccgatcaac gtctcatttt cgccaaaagt tggcccaggg cttcccggta    5940
tcaacaggga caccaggatt tatttattct gcgaagtgat cttccgtcac aggtatttat    6000
tcggcgcaaa gtgcgtcggg tgatgctgcc aacttactga tttagtgtat gatggtgttt    6060
ttgaggtgct ccagtggctt ctgtttctat cagctgtccc tcctgttcag ctactgacgg    6120
ggtggtgcgt aacggcaaaa gcaccgccgg acatcagcgc tagtagcgga gtgtatactg    6180
gcttactatg ttggcactga tgagggtgtc agtgaagtgc ttcatgtggc aggagaaaaa    6240
aggctgcacc ggtgcgtcag cagaatatgt gatacaggat atattccgct tcctcgctca    6300
ctgactcgct acgctcggtc gttcgactgc ggcgagcgga atggcttac gaacggggcg    6360
gagatttcct ggaagatgcc aggaagatac ttaacaggga agtgagaggg ccgcggcaaa    6420
gccgtttttc cataggctcc gccccctga caagcatcac gaaatctgac gctcaaatca    6480
gtggtggcga aacccgacag gactataaag ataccaggcg tttccccctg gcggctccct    6540
cgtgcgctct cctgttcctg cctttcggtt taccggtgtc attccgctgt tatggccgcg    6600
tttgtctcat tccacgcctg acactcagtt ccgggtaggc agttcgctcc aagctggact    6660
gtatgcacga accccccgtt cagtccgacc gctgcgcctt atccggtaac tatcgtcttg    6720
agtccaaccc ggaaagacat gcaaaagcac cactggcagc agccactggt aattgattta    6780
gaggagttag tcttgaagtc atgcgccggt taaggctaaa ctgaaaggac aagttttggt    6840
gactgcgctc ctccaagcca gttacctcgg ttcaaagagt tggtagctca gagaaccttc    6900
gaaaaccgc cctgcaaggc ggttttttcg ttttcagagc aagagattac gcgcagacca    6960
aaacgatctc aagaagatca tcttattaat cagataaaat atttgctcat gagcccgaag    7020
tggcgagccc gatcttcccc atcggtgatg tcggcgatat aggcgccagc aaccgcacct    7080
gtggcgccgg tgatgccggc cacgatgcgt ccggcgtaga ggatctgctc atgtttgaca    7140
gcttatc                                                             7147

<210> SEQ ID NO 19
<211> LENGTH: 5883
<212> TYPE: DNA
```

<213> ORGANISM: Artificial Sequence
<220> FEATURE:
<223> OTHER INFORMATION: pPRO43 vector

<400> SEQUENCE: 19

```
atcgatttag cttttcagac gacgccaaaa ggtcgtacgt gaaataccca aatagttggc      60
cgcagccgtc ttgtcaccat taaacttctc aagcgcttgc tgcggggtca gcaaacgcgg    120
agccggcgtc tttgcgctct cacgcgccag ctccggcagc agcaactgca tgaattgcgg    180
agtcagatcc ggggtcggct caacggacag gaacagcgcg aggcgttcca tcatattacg    240
cagctcgcgg atgttacccg gccagtcata atgcagcagc accgtttcgc tcgcctgcag    300
accctggcgc agtgccgcag agaacggtgc gctcagggct gccagcgaga ctttcaggaa    360
agactccgcc agcggtaaaa tgtcggcgac acgttcacgc aacggcggga gctgcagacg    420
cagaatgctc aggcggtaga acaggtcgcg acgaaaacgg ccctgttgca tatcctcttc    480
cagattgcag tgggtcgcgc taatcacgcg cacgtctacc ggaaccggtt gatgaccacc    540
gacgcgggtc acttctttct cttccagcac acgcagcaga cgggtttgca atggcagcgg    600
catctcaccg atctcgtcca ggaacaaggt gccgccgtgg gcaatttcaa acaaaccagc    660
acggccaccg cgacggctac ccgtgaatgc gccctcttcg tagccaaaca gctcagcttc    720
cagcaggctt ccgcgattg caccgcaatt aactgccaca acggatgag atttcttacc    780
ctggcgggca tcgtgacggg cgaaatactc acgatggatt gcttgcgcag ccagttcctt    840
acccgtacca gtctcgcctt cgatcagaac agccgcgctg ctacgtgcat acagcagaat    900
ggtctggcga acttgctcca tttgagggct ttggcccagc atatcaccca ggacataacg    960
ggtacgcagc gcattacgcg tcgcatcgtg ggtgttgtgg cgcaggctca ttctggtcat   1020
gtccagggcg tcgctgaacg cctgacgcac cgttgccgcg ctgtagataa agatgcccgt   1080
catgcccgct tcttcggcca agtccgtgat cagacccgca ccaaccacag cctcggtacc   1140
gttcgctttc agttcgttga tctggccacg tgcatcttcc tcggtaatgt agctgcgttg   1200
gtccaggcgc agattaaagg tcttttgaaa cgcgaccagc gcagggatcg tttcctggta   1260
ggtgacaacg ccaatcgagg aggtcagttt gcctgccttc gccagcgcct gcaagacatc   1320
gtaaccgctc ggcttaatca ggatcaccgg cacggacaga cgggatttca ggtaggcacc   1380
attgctaccc gctgcgataa tggcgtcaca acgctcgttg gccagctttt tgcgaatgta   1440
ggtaacggct ttctcgaaac ccagctgaat cggagtgatg ttcgccaggt gatcaaactc   1500
caggctaatg tcgcggaaca actcgaacag acgggtgacg ctaacggtcc aaataactgg   1560
tttatcatcg ttcaaacgcg gtgggtgtgc catggtgaat acctcctgtt aagaaaccga   1620
atattgggtt taaacttgtt tcataattgt tgcaatgaaa cgcggtgaaa cattgcctga   1680
aacgttaact gaaacgcata tttgcggatt agttcatgac tttatctcta acaaattgaa   1740
attaaacatt taatttattt aaggcaattg tggcacaccc cttgctttgt ctttatcaac   1800
gcaaataaca agttgataac aagctagcga attcgagctc ggtacccggg gatcctctag   1860
agtcgacctg caggcatgca agcttggctg ttttggcgga tgagagaaga ttttcagcct   1920
gatacagatt aaatcagaac gcagaagcgg tctgataaaa cagaatttgc ctggcggcag   1980
tagcgcggtg gtcccacctg accccatgcc gaactcagaa gtgaaacgcc gtagcgccga   2040
tggtagtgtg gggtctcccc atgcgagagt agggaactgc caggcatcaa ataaaacgaa   2100
aggctcagtc gaaagactgg gcctttcgtt ttatctgttg tttgtcggtg aacgctctcc   2160
tgagtaggac aaatccgccg ggagcggatt tgaacgttgc gaagcaacgg cccggagggt   2220
```

```
ggcgggcagg acgcccgcca taaactgcca ggcatcaaat taagcagaag gccatcctga    2280
cggatggcct ttttgcgttt ctacaaactc ttttgtttat ttttctaaat acattcaaat    2340
atgtatccgc tcatgagaca ataaccctga taaatgcttc aataatattg aaaaaggaag    2400
agtatgagta ttcaacattt ccgtgtcgcc cttattccct ttttgcggc attttgcctt     2460
cctgttttg ctcacccaga aacgctggtg aaagtaaaag atgctgaaga tcagttgggt     2520
gcagcaaact attaactggc gaactactta ctctagcttc ccggcaacaa ttaatagact    2580
ggatggaggc ggataaagtt gcaggaccac ttctgcgctc ggcccttccg gctggctggt    2640
ttattgctga taaatctgga gccggtgagc gtgggtctcg cggtatcatt gcagcactgg    2700
ggccagatgg taagccctcc cgtatcgtag ttatctacac gacggggagt caggcaacta    2760
tggatgaacg aaatagacag atcgctgaga taggtgcctc actgattaag cattggtaac    2820
tgtcagacca gtttactca tatatacttt agattgattt acgcgccctg tagcggcgca     2880
ttaagcgcgg cgggtgtggt ggttacgcgc agcgtgaccg ctacacttgc cagcgcccta    2940
gcgcccgctc ctttcgcttt cttcccttcc tttctcgcca cgttcgccgg ctttccccgt    3000
caagctctaa atcgggggct ccctttaggg ttccgattta gtgctttacg gcacctcgac    3060
cccaaaaaac ttgatttggg tgatggttca cgtagtgggc catcgccctg atagacggtt    3120
tttcgccctt tgacgttgga gtccacgttc tttaatagtg gactcttgtt ccaaactgga    3180
acaacactca accctatctc gggctattct tttgatttat aagggatttt gccgatttcg    3240
gcctattggt taaaaaatga gctgatttaa caaaaattta acgcgaattt taacaaaata    3300
ttaacgttta caatttaaaa ggatctaggt gaagatcctt tttgataatc tcatgaccaa    3360
aatcccttaa cgtgagtttt cgttccactg agcgtcagac cccgtagaaa agatcaaagg    3420
atcttcttga tccttttttt ttctgcgcgt aatctgctgc ttgcaaacaa aaaaaccacc    3480
gctaccagcg gtggtttgtt tgccggatca agagctacca actctttttc cgaaggtaac    3540
tggcttcagc agagcgcaga taccaaatac tgtccttcta gtgtagccgt agttaggcca    3600
ccacttcaag aactctgtag caccgcctac atacctcgct ctgctaatcc tgttaccagt    3660
caggcatttg agaagcacac ggtcacactg cttccggtag tcaataaacc ggtaaaccag    3720
caatagacat aagcggctat ttaacgaccc tgccctgaac cgacgaccgg gtcgaatttg    3780
ctttcgaatt tctgccattc atccgcttat tatcacttat tcaggcgtag caaccaggcg    3840
tttaagggca ccaataactg ccttaaaaaa attacgcccc gccctgccac tcatcgcagt    3900
actgttgtaa ttcattaagc attctgccga catggaagcc atcacaaacg gcatgatgaa    3960
cctgaatcgc cagcggcatc agcaccttgt cgccttgcgt ataatatttg cccatggtga    4020
aaacgggggc gaagaagttg tccatattgg ccacgtttaa atcaaaactg gtgaaactca    4080
cccagggatt ggctgagacg aaaaacatat tctcaataaa ccctttaggg aataggcca    4140
ggttttcacc gtaacacgcc acatcttgcg aatatatgtg tagaaactgc cggaaatcgt    4200
cgtggtattc actccagagc gatgaaaacg tttcagtttg ctcatggaaa acggtgtaac    4260
aagggtgaac actatcccat atcaccagct caccgtcttt cattgccata cggaattccg    4320
gatgagcatt catcaggcgg gcaagaatgt gaataaaggc cggataaaac ttgtgcttat    4380
ttttctttac ggtctttaaa aaggccgtaa tatccagctg aacggtctgg ttataggtac    4440
attgagcaac tgactgaaat gcctcaaaat gttctttacg atgccattgg gatatatcaa    4500
cggtggtata tccagtgatt ttttctcca ttttagcttc cttagctcct gaaaatctcg     4560
```

```
ataactcaaa aaatacgccc ggtagtgatc ttatttcatt atggtgaaag ttggaacctc    4620
ttacgtgccg atcaacgtct cattttcgcc aaaagttggc ccagggcttc ccggtatcaa    4680 caggacacc aggatttatt tattctgcga agtgatcttc cgtcacaggt atttattcgg     4740
cgcaaagtgc gtcgggtgat gctgccaact tactgattta gtgtatgatg gtgtttttga    4800
ggtgctccag tggcttctgt ttctatcagc tgtccctcct gttcagctac tgacggggtg    4860
gtgcgtaacg gcaaaagcac cgccggacat cagcgctagt agcggagtgt atactggctt    4920
actatgttgg cactgatgag ggtgtcagtg aagtgcttca tgtggcagga gaaaaaaggc    4980
tgcaccggtg cgtcagcaga atatgtgata caggatatat ccgcttcct cgctcactga     5040 ctcgctacgc tcggtcgttc gactgcggcg agcggaaatg gcttacgaac ggggcggaga    5100
tttcctggaa gatgccagga agatacttaa caggaagtg agagggccgc ggcaaagccg     5160
tttttccata ggctccgccc ccctgacaag catcacgaaa tctgacgctc aaatcagtgg    5220
tggcgaaacc cgacaggact ataaagatac caggcgtttc cccctggcgg ctccctcgtg    5280
cgctctcctg ttcctgcctt tcggtttacc ggtgtcattc cgctgttatg gccgcgtttg    5340
tctcattcca cgcctgacac tcagttccgg gtaggcagtt cgctccaagc tggactgtat    5400
gcacgaaccc cccgttcagt ccgaccgctg cgccttatcc ggtaactatc gtcttgagtc    5460
caacccggaa agacatgcaa aagcaccact ggcagcagcc actggtaatt gatttagagg    5520
agttagtctt gaagtcatgc gccggttaag gctaaactga aaggacaagt tttggtgact    5580
gcgctcctcc aagccagtta cctcggttca aagagttggt agctcagaga accttcgaaa    5640
aaccgccctg caaggcggtt ttttcgtttt cagagcaaga gattacgcgc agaccaaaac    5700
gatctcaaga agatcatctt attaatcaga taaaatattt gctcatgagc ccgaagtggc    5760
gagcccgatc ttccccatcg gtgatgtcgg cgatataggc gccagcaacc gcacctgtgg    5820
cgccggtgat gccggccacg atgcgtccgg cgtagaggat ctgctcatgt ttgacagctt    5880
atc                                                                  5883

<210> SEQ ID NO 20
<211> LENGTH: 35
<212> TYPE: DNA
<213> ORGANISM: Artificial Sequence
<220> FEATURE:
<223> OTHER INFORMATION: J23104 promoter

<400> SEQUENCE: 20
ttgacagcta gctcagtcct aggtattgtg ctagc                                35

<210> SEQ ID NO 21
<211> LENGTH: 6545
<212> TYPE: DNA
<213> ORGANISM: Artificial Sequence
<220> FEATURE:
<223> OTHER INFORMATION: pJ1231-03C plasmid

<400> SEQUENCE: 21
tcagaattgg ttaattggtt gtaacactga cccctatttg tttattttc taaatacatt      60 caaatatgta tccgctcatg agacaataac cctgataaat gcttcaataa tattgaaaaa    120
ggaagaatat gagccatatt caacgggaaa cgtcgaggcc gcgattaaat tccaacatgg    180
atgctgattt atatgggtat aaatgggctc gcgataatgt cggcaatca ggtgcgacaa     240 tctatcgctt gtatgggaag cccgatgcgc cagagttgtt tctgaaacat ggcaaaggta    300
gcgttgccaa tgatgttaca gatgagatgg tcagactaaa ctggctgacg gaatttatgc    360
```

```
cacttccgac catcaagcat tttatccgta ctcctgatga tgcatggtta ctcaccactg    420
cgatccccgg aaaaacagcg ttccaggtat tagaagaata tcctgattca ggtgaaaata    480
ttgttgatgc gctggcagtg ttcctgcgcc ggttgcactc gattcctgtt tgtaattgtc    540
cttttaacag cgatcgcgta tttcgcctcg ctcaggcgca atcacgaatg aataacggtt    600
tggttgatgc gagtgatttt gatgacgagc gtaatggctg gcctgttgaa caagtctgga    660
aagaaatgca taaactttty ccattctcac cggattcagt cgtcactcat ggtgatttct    720
cacttgataa ccttattttt gacgagggga aattaatagg ttgtattgat gttggacgag    780
tcggaatcgc agaccgatac caggatcttg ccatcctatg gaactgcctc ggtgagtttt    840
ctccttcatt acagaaacgg cttttcaaa aatatggtat tgataatcct gatatgaata    900
aattgcaatt tcatttgatg ctcgatgagt ttttctaact catgaccaaa atcccttaac    960
gtgagttacg cgcgcgtcgt tccactgagc gtcagacccc gtagaaaaga tcaaaggatc   1020
ttcttgagat ccttttttc tgcgcgtaat ctgctgcttg caaacaaaaa aaccaccgct   1080
accagcggtg gtttgtttgc cggatcaaga gctaccaact ctttttccga aggtaactgg   1140
cttcagcaga gcgcagatac caaatactgt tcttctagtg tagccgtagt tagcccacca   1200
cttcaagaac tctgtagcac cgcctacata cctcgctctg ctaatcctgt taccagtggc   1260
tgctgccagt ggcgataagt cgtgtcttac cgggttggac tcaagacgat agttaccgga   1320
taaggcgcag cggtcgggct gaacggggg ttcgtgcaca cagcccagct tggagcgaac   1380
gacctacacc gaactgagat acctacagcg tgagctatga gaaagcgcca cgcttcccga   1440
agggagaaag gcggacaggt atccggtaag cggcagggtc ggaacaggag agcgcacgag   1500
ggagcttcca gggggaaacg cctggtatct ttatagtcct gtcgggtttc gccacctctg   1560
acttgagcgt cgatttttgt gatgctcgtc agggggggcgg agcctatgga aaaacgccag   1620
caacgcggcc ttttacggt tcctggcctt tgctggcct tttgctcaca tgttctttcc   1680
tgcgttatcc cctgattctg tggataaccg tattaccgcc tttgagtgag ctgataccgc   1740
tcggggtcgt gcaggtagtt tatcattatc aatactcgcc atttcaaaga atacgtaaat   1800
aattaatagt agtgatttc ctaactttat ttagtcaaaa aattagcctt ttaattctgc   1860
tgtaacccgt acatgcccaa atagggggc gggttacaca gaatatataa catcgtaggt   1920
gtctgggtga acagtttatt cctggcatcc actaaatata atggagcccg ctttttaagc   1980
tggcatccag aaaaaaaaag aatcccagca ccaaatatt gttttcttca ccaaccatca   2040
gttcataggt ccattctctt agcgcaacta cagagaacag gggcacaaac aggcaaaaaa   2100
cgggcacaac ctcaatggag tgatgcaacc agcctggagt aaatgatgac acaaggcaat   2160
tgacccacgc atgtatctat ctcatttct tacaccttct attccttct gctctctctg   2220 atttggaaaa agctgaaaaa aaaggttgaa accagttccc tgaaattatt ccctacttg   2280 actaataagt atataaagac ggtaggtatt gattgtaatt ctgtaaatct atttcttaaa   2340
cttcttaaat tctacttta tagttagtct ttttttagt tttaaaacac cagaacttag   2400
tttcgacgga taaatgaca gctttaactg aaggggccaa gcttttcgaa aaagagatcc   2460
catatatcac cgaacttgaa ggtgacgttg agggtatgaa gttatcata aaggagaag   2520 gcacaggtga tgcgacaacg ggtacaatca aggcaaagta catttgtaca actggggacc   2580
tgcctgtccc atgggccact tggtgtcta ctttgtctta cggcgtacaa tgttttgcta   2640
agtacccttc acacatcaaa gatttcttta agtctgcaat gcctgaagga tacacacagg   2700
```

```
aacgtacaat ttcatttgag ggcgacggtg tctataaaac aagagctatg gttacttatg    2760
aaagaggttc catctacaac agagtgacac taacgggcga aaatttcaaa aaggatggac    2820
atattttgcg taaaaacgta gctttccaat gcccaccatc aatactatac attctgccag    2880
atactgtaaa caatggtatt agagtcgagt ttaatcaagc ttatgatata gaaggtgtca    2940
ctgaaaaatt ggttacaaaa tgcagccaaa tgaatagacc attggcagga tctgccgctg    3000
tgcatatccc tagataccat cacattacct accacaccaa attaagtaaa gacagggatg    3060
aacgaagaga tcatatgtgt ttagttgagg ttgttaaggc agttgatctc gacacttacc    3120
aataaatcat gtaattagtt atgtcacgct tacattcacg ccctccccc acatccgctc    3180 taaccgaaaa ggaaggagtt agacaacctg aagtctaggt ccctatttat ttttttatag    3240
ttatgttagt attaagaacg ttatttatat ttcaaatttt tctttttttt ctgtacagac    3300
gcgtgtacgc atgtaacatt atactgaaaa ccttgcttga gaaggttttg ggacgctcga    3360
aggctttaat ttgcggcccc tcacctgcac gcaaaatagg ataattatac tctatttctc    3420
aacaagtaat tggttgtttg gccgagcggt ctaaggcgcc tgattcaaga aatatcttga    3480
ccgcagttaa ctgtgggaat actcaggtat cgtaagatgc aagagttcga atctcttagc    3540
aaccattatt ttttttcctca acataacgag aacacacagg ggcgctatcg cacagaatca    3600
aattcgatga ctggaaattt tttgttaatt tcagaggtcg cctgacgcat ataccttttt    3660
caactgaaaa attgggagaa aaaggaaagg tgagagcgcc ggaaccggct tttcatatag    3720
aatagagaag cgttcatgac taaatgcttg catcacaata cttgaagttg acaatattat    3780
ttaaggacct attgtttttt ccaataggtg gttagcaatc gtcttacttt ctaacttttc    3840 ttaccttta catttcagca atatatatat atatatttca aggatatacc attctaatgt    3900
ctgcccctaa gaagatcgtc gttttgccag gtgaccacgt tggtcaagaa atcacagccg    3960
aagccattaa ggttcttaaa gctatttctg atgttcgttc caatgtcaag ttcgatttcg    4020
aaaatcattt aattggtggt gctgctatcg atgctacagg tgttccactt ccagatgagg    4080
cgctggaagc ctccaagaag gctgatgccg ttttgttagg tgctgtgggt ggtcctaaat    4140
ggggtaccgg tagtgttaga cctgaacaag gtttactaaa aatccgtaaa gaacttcaat    4200
tgtacgccaa cttaagacca tgtaactttg catccgactc tctttagac ttatctccaa    4260 tcaagccaca atttgctaaa ggtactgact tcgttgttgt cagagaatta gtgggaggta    4320
tttactttgg taagagaaag aagatgatg gtgatggtgt cgcttgggat agtgaacaat    4380
acaccgttcc agaagtgcaa agaatcacaa gaatggccgc tttcatggcc ctacaacatg    4440
agccaccatt gcctatttgg tccttggata aagctaatgt tttggcctct tcaagattat    4500
ggagaaaaac tgtggaggaa accatcaaga acgaattccc tacattgaag gttcaacatc    4560
aattgattga ttctgccgcc atgatcctag ttaagaaccc aacccaccta aatggtatta    4620
taatcaccag caacatgttt ggtgatatca tctccgatga agcctccgtt atcccaggtt    4680
ccttgggttt gttgccatct gcgtccttgg cctctttgcc agacaagaac accgcatttg    4740
gtttgtacga accatgccac ggttctgctc cagatttgcc aaagaataag gtcaacccta    4800
tcgccactat cttgtctgct gcaatgatgt tgaaattgtc attgaacttg cctgaagaag    4860
gtaaggccat tgaagatgca gttaaaaagg ttttggatgc aggcatcaga actggtgatt    4920
taggtggttc caacagtacc accgaagtcg gtgatgctgt cgccgaagaa gttaagaaaa    4980
tccttgctta aaaagattct cttttttat gatttgta cataaactt ataaatgaaa    5040 ttcataatag aaacgacacg aaattacaaa atggaatatg ttcatagggt aacgctatga    5100
```

```
tccaatatca aaggaaatga tagcattgaa ggatgagact aatccaattg aggagtggca    5160
gcatatagaa cagctaaagg gtagtgctga aggaagcata cgatacccg catggaatgg     5220
gataatatca caggaggtac tagactacct ttcatcctac ataaatagac gcatataagt    5280
acgcatttaa gcataaacac gcactatgcc gttcttctca tgtatatata tatacaggca   5340
acacgcagat ataggtgcga cgtgaacagt gagctgtatg tgcgcagctc gcgttgcatt    5400
ttcggaagcg ctcgttttcg gaaacgcttt gaagttccta ttccgaagtt cctattctct    5460
agaaagtata ggaacttcag agcgcttttg aaaaccaaaa gcgctctgaa gtcgcacttt   5520
caaaaaacca aaacgcacc ggactgtaac gagctactaa aatattgcga ataccgcttc    5580
cacaaacatt gctcaaaagt atctctttgc tatatatctc tgtgctatat ccctatataa   5640
cctacccatc caccttttcgc tccttgaact tgcatctaaa ctcgacctct acatttttta  5700
tgtttatctc tagtattact ctttagacaa aaaaattgta gtaagaacta ttcatagagt   5760
gaatcgaaaa caatacgaaa atgtaaacat ttcctatacg tagtatatag agacaaaata   5820
gaagaaaccg ttcataattt tctgaccaat gaagaatcat caacgctatc actttctgtt   5880
cacaaagtat gcgcaatcca catcggtata gaatataatc ggggatgcct ttatcttgaa   5940
aaaatgcacc cgcagcttcg ctagtaatca gtaaacgcgg gaagtggagt caggcttttt    6000
ttatggaaga gaaatagac accaaagtag ccttcttcta accttaacgg acctacagtg    6060
caaaaagtta tcaagagact gcattataga gcgcacaaag gagaaaaaaa gtaatctaag    6120
atgctttgtt agaaaatag cgctctcggg atgcattttt gtagaacaaa aagaagtat     6180
agattctttg ttggtaaaat agcgctctcg cgttgcattt ctgttctgta aaaatgcagc   6240
tcagattctt tgtttgaaaa attagcgctc tcgcgttgca ttttgtttt acaaaaatga    6300
agcacagatt cttcgttggt aaaatagcgc tttcgcgttg catttctgtt ctgtaaaaat   6360
gcagctcaga ttcttttgttt gaaaaattag cgctctcgcg ttgcattttt gttctacaaa   6420
atgaagcaca gatgcttcgt tcaggtggca cttttcgggg aaatgtgcgc ggaacccta    6480
tttgtttatt tttctaaata cattcaaata tgtatccgct catgagacaa taaccctgat    6540
attgg                                                               6545
```

<210> SEQ ID NO 22
<211> LENGTH: 6009
<212> TYPE: DNA
<213> ORGANISM: Artificial Sequence
<220> FEATURE:
<223> OTHER INFORMATION: pJ1234-03C plasmid

<400> SEQUENCE: 22

```
tcagaattgg ttaattggtt gtaacactga cccctatttg tttatttttc taaatacatt     60
caaatatgta tccgctcatg agacaataac cctgataaat gcttcaataa tattgaaaaa    120
ggaagaatat gagtattcaa catttccgtg tcgcccttat tcccttttt gcggcatttt    180
gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcactttta agttctgcta tgtggcgcgg   360
tattatcccg tattgacgcc gggcaagagc aactcggtcg ccgcatacac tattctcaga   420
atgacttggt tgagtactca ccagtcacag aaaagcatct tacgatggc atgacagtaa    480
gagaattatg cagtgctgcc ataaccatga gtgataacac tgcggccaac ttacttctga   540
```

```
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcgatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatccgga gccggtgagc    840
gtggttctcg cggtatcatc gcagcgctgg ggccagatgg taagcccctcc cgtatcgtag    900 ttatctacac gacggggagt caggcaacta tggatgaacg aaatagacag atcgctgaga    960
taggtgcctc actgattaag cattggtaac tcatgaccaa aatcccttaa cgtgagttac   1020
gcgcgcgtcg ttccactgag cgtcagaccc cgtagaaaag atcaaaggat cttcttgaga   1080 tcctttttt ctgcgcgtaa tctgctgctt gcaaacaaaa aaaccaccgc taccagcggt   1140
ggtttgtttg ccggatcaag agctaccaac tcttttccg aaggtaactg gcttcagcag   1200
agcgcagata ccaaatactg ttcttctagt gtagccgtag ttagcccacc acttcaagaa   1260
ctctgtagca ccgcctacat acctcgctct gctaatcctg ttaccagtgg ctgctgccag   1320
tggcgataag tcgtgtctta ccgggttgga ctcaagacga tagttaccgg ataaggcgca   1380
gcggtcgggc tgaacggggg gttcgtgcac acagcccagc ttggagcgaa cgacctacac   1440
cgaactgaga tacctacagc gtgagctatg agaaagcgcc acgcttcccg aagggagaaa   1500
ggcggacagg tatccggtaa gcggcagggt cggaacagga gagcgcacga gggagcttcc   1560
agggggaaac gcctggtatc tttatagtcc tgtcgggttt cgccacctct gacttgagcg   1620
tcgatttttg tgatgctcgt caggggggcg gagcctatgg aaaaacgcca gcaacgcggc   1680
ctttttacgg ttcctggcct tttgctggcc ttttgctcac atgttctttc ctgcgttatc   1740
ccctgattct gtggataacc gtattaccgc ctttgagtga gctgataccg ctcggggtcg   1800
tgcaggtagt ttatcattat caatactcgc catttcaaag aatacgtaaa taattaatag   1860
tagtgatttt cctaacttta tttagtcaaa aaattagcct tttaattctg ctgtaacccg   1920
tacatgccca aaatagggggg cgggttacac agaatatata acatcgtagg tgtctgggtg   1980
aacagtttat tcctggcatc cactaaatat aatggagccc gcttttttaag ctggcatcca   2040 gaaaaaaaaa gaatcccagc accaaaatat tgttttcttc accaaccatc agttcatagg   2100
tccattctct tagcgcaact acagagaaca ggggcacaaa caggcaaaaa acgggcacaa   2160
cctcaatgga gtgatgcaac cagcctggag taaatgatga cacaaggcaa ttgacccacg   2220
catgtatcta tctcattttc ttacaccttc tattaccttc tgctctctct gatttggaaa   2280
aagctgaaaa aaaaggttga aaccagttcc ctgaaattat tcccctactt gactaataag   2340
tatataaaga cggtaggtat tgattgtaat tctgtaaatc tatttcttaa acttcttaaa   2400
ttctactttt atagttagtc ttttttttag ttttaaaaca ccagaactta gtttcgacgg   2460
ataaaatgac agctttaact gaaggggcca agcttttcga aaaagagatc ccatatatca   2520
ccgaacttga aggtgacgtt gagggtatga agtttatcat aaaaggagaa ggcacaggtg   2580
atgcgacaac gggtacaatc aaggcaaagt acatttgtac aactgggac ctgcctgtcc   2640 catgggccac tttggtgtct actttgtctt acgcgtaca atgttttgct aagtacccttt   2700 cacacatcaa agatttcttt aagtctgcaa tgcctgaagg atacacacag gaacgtacaa   2760
tttcatttga gggcgacggt gtctataaaa caagagctat ggttacttat gaaagaggtt   2820
ccatctacaa cagagtgaca ctaacggcg aaaattcaa aaaggatgga catatttgc   2880 gtaaaaacgt agctttccaa tgcccaccat caatactata cattctgcca gatactgtaa   2940
```

```
acaatggtat tagagtcgag tttaatcaag cttatgatat agaaggtgtc actgaaaaat    3000
tggttacaaa atgcagccaa atgaatagac cattggcagg atctgccgct gtgcatatcc    3060
ctagatacca tcacattacc taccacacca aattaagtaa agacagggat gaacgaagag    3120
atcatatgtg tttagttgag gttgttaagg cagttgatct cgacacttac caataaatca    3180
tgtaattagt tatgtcacgc ttacattcac gccctccccc cacatccgct ctaaccgaaa    3240
aggaaggagt tagacaacct gaagtctagg tccctattta ttttttata gttatgttag      3300 tattaagaac gttatttata tttcaaattt ttcttttttt tctgtacaga cgcgtgtacg    3360
catgtaacat tatactgaaa accttgcttg agaaggtttt gggacgctcg aaggctttaa    3420
tttgcggccc ctcacctgca cgcaaaaagc ttttcaattc aattcatcat tttttttta     3480 ttcttttttt tgatttcggt ttctttgaaa ttttttttgat tcggtaatct ccgaacagaa   3540
ggaagaacga aggaaggagc acagacttag attggtatat atacgcatat gtagtgttga    3600
agaaacatga aattgcccag tattcttaac ccaactgcac agaacaaaaa ccagcaggaa     3660
acgaagataa atcatgtcga aagctacata taaggaacgt gctgctactc atcctagtcc    3720
tgttgctgcc aagctatttta atatcatgca cgaaaagcaa acaaacttgt gtgcttcatt    3780
ggatgttcgt accaccaagg aattactgga gttagttgaa gcattaggtc ccaaaatttg     3840
tttactaaaa acacatgtgg atatcttgac tgattttttcc atggagggca cagttaagcc    3900
gctaaaggca ttatccgcca agtacaattt tttactcttc gaagatagaa aatttgctga     3960
cattggtaat acagtcaaat tgcagtactc tgcgggtgta tacagaatag cagaatgggc    4020
agacattacg aatgcacacg gtgtggtggg cccaggtatt gttagcggtt tgaagcaggc    4080
ggcagaagaa gtaacaaagg aacctagagg cctttttgatg ttagcagaat tgtcatgcaa    4140
gggctcccta tctactggag aatatactaa gggtactgtt gacattgcga aaagcgacaa    4200
agattttgtt atcggcttta ttgctcaaag agacatgggt ggaagagatg aaggttacga    4260
ttggttgatt atgacacccg gtgtgggttt agatgacaag ggagatgcat tgggtcaaca    4320
gtatagaacc gtggatgatg ttgtctctac aggatctgac attattattg ttggaagagg    4380
actatttgca aagggaaggg atgctaaggt agagggtgaa cgttacagaa aagcaggctg    4440
ggaagcatat ttgagaagat gcggccagca aaactaaaaa actgtattat aagtaaatgc    4500
atgtatacta aactcacaaa ttagagcttc aatttaatta tatcagttat tacccacgct    4560
atgatccaat atcaaaggaa atgatagcat tgaaggatga gactaatcca attgaggagt    4620
ggcagcatat agaacagcta aagggtagtg ctgaaggaag catacgatac cccgcatgga    4680
atgggataat atcacaggag gtactagact acctttcatc ctacataaat agacgcatat    4740
aagtacgcat ttaagcataa acacgcacta tgccgttctt ctcatgtata tatatataca    4800
ggcaacacgc agatataggt gcgacgtgaa cagtgagctg tatgtgcgca gctcgcgttg    4860
cattttcgga agcgctcgtt ttcggaaacg ctttgaagtt cctattccga agttcctatt    4920
ctctagaaag tataggaact tcagagcgct tttgaaaacc aaaagcgctc tgaagtcgca    4980
ctttcaaaaa accaaaaacg caccggactg taacgagcta ctaaaatatt gcgaataccg    5040
cttccacaaa cattgctcaa aagtatctct ttgctatata tctctgtgct atatccctat    5100
ataacctacc catccaccct tcgctccttg aacttgcatc taaactcgac ctctacattt    5160
tttatgttta tctctagtat tactctttag acaaaaaaat tgtagtaaga actattcata    5220
gagtgaatcg aaaacaatac gaaaatgtaa acatttccta tacgtagtat atagagacaa    5280
```

```
aatagaagaa accgttcata attttctgac caatgaagaa tcatcaacgc tatcactttc    5340
tgttcacaaa gtatgcgcaa tccacatcgg tatagaatat aatcggggat gcctttatct    5400
tgaaaaaatg cacccgcagc ttcgctagta atcagtaaac gcgggaagtg gagtcaggct    5460 tttttatgg  aagagaaaat agacaccaaa gtagccttct tctaaccta  acggacctac    5520 agtgcaaaaa gttatcaaga gactgcatta tagagcgcac aaaggagaaa aaaagtaatc    5580
taagatgctt tgttagaaaa atagcgctct cgggatgcat ttttgtagaa caaaaaagaa    5640
gtatagattc tttgttggta aaatagcgct ctcgcgttgc atttctgttc tgtaaaaatg    5700
cagctcagat tctttgtttg aaaaattagc gctctcgcgt tgcatttttg ttttacaaaa    5760
atgaagcaca gattcttcgt tggtaaaata gcgctttcgc gttgcatttc tgttctgtaa    5820
aaatgcagct cagattcttt gtttgaaaaa ttagcgctct cgcgttgcat ttttgttcta    5880
caaaatgaag cacagatgct tcgttcaggt ggcactttc  ggggaaatgt gcgcggaacc    5940
cctatttgtt tattttctta aatacattca aatatgtatc cgctcatgag acaataaccc    6000
tgatattgg                                                           6009
```

COORDINATED COEXPRESSION OF THROMBIN

REFERENCE TO RELATED APPLICATIONS

This application is a national stage entry of International Application No. PCT/US14/14968, which is a continuation-in-part of, and claims all benefits and rights of priority of, International Application No. PCT/US13/53562 filed on 5 Aug. 2013, which claims the benefit of U.S. Provisional Application No. 61/679,751, filed on Aug. 5, 2012, and U.S. Provisional Application No. 61/747,246, filed on Dec. 29, 2012, the entire disclosures of all of which are incorporated by reference herein.

STATEMENT REGARDING FEDERALLY SPONSORED RESEARCH OR DEVELOPMENT

The content of this application was partially supported by the National Institutes of Health (NHLBI grant 1R44HL117589).

THE NAMES OF THE PARTIES TO A JOINT RESEARCH AGREEMENT

AbSci, LLC and Aronora, Inc. are parties to a joint research agreement.

REFERENCE TO THE SEQUENCE LISTING

This application includes a sequence listing submitted electronically, in a file entitled "AbSciA-01PCT-ST25", created on 5 Feb. 2014 and having a size of 96 kilobytes (KB), which is incorporated by reference herein.

FIELD OF THE INVENTION

The present invention is in the general technical fields of molecular biology and biotechnological manufacturing. More particularly, the present invention is in the technical field of recombinant protein expression, and specifically the technical field of expression of thrombin.

BACKGROUND OF THE INVENTION

Thrombin is a serine protease that plays opposing functional roles in blood coagulation: it is both a procoagulant that converts fibrinogen into an insoluble fibrin clot, and an anticoagulant that activates protein C, and thrombin also has an extracellular protease-activated receptor (PAR) activation function (Di Cera, "Thrombin", Mol Aspects Med 2008 August; 29(4): 203-254, doi: 10.1016/j.mam.2008.01.001, Epub 2008 Feb. 1). Wild-type thrombin expressed in mammalian cells is often used for its procoagulant properties, particularly to address the problem of surgical bleeding. Thrombin variants engineered for optimal activity toward protein C and minimal activity toward fibrinogen have shown remarkable anticoagulant and antithrombotic properties of therapeutic interest, both in vitro and in vivo (Cantwell and Di Cera, "Rational design of a potent anticoagulant thrombin", J Biol Chem 2000 Dec. 22; 275(51): 39827-39830; Epub 2000 Nov. 1; Gruber et al., "The thrombin mutant W215A/E217A shows safe and potent anticoagulant and antithrombotic effects in vivo", J Biol Chem 2002 Aug. 2; 277(31): 27581-27584; Epub 2002 Jun. 17; U.S. Pat. Nos. 6,706,512; 7,223,583). The antithrombotic effect of anticoagulant thrombin variants in non-human primates is more efficacious than the direct administration of activated protein C, and is safer to use than the administration of low molecular weight heparins (Gruber et al., "Relative antithrombotic and antihemostatic effects of protein C activator versus low-molecular-weight heparin in primates", Blood 2007 May 1; 109(9): 3733-3740; Epub 2007 Jan. 16).

The production of thrombin in vivo proceeds through a series of intermediate forms, including prothrombin, prethrombin-1, and prethrombin-2. Each step of this process involves a highly regulated cleavage of the precursor form of thrombin, until mature thrombin is produced (DiBella et al., "Expression and folding of recombinant bovine prethrombin-2 and its activation to thrombin", J Biol Chem 1995 Jan. 6; 270(1): 163-169). Mature thrombin is formed of two polypeptide chains, the A chain and the B chain, with a disulfide bond between the A and the B chain, and can be produced by cleavage of prethrombin-2 at a specific site.

Thrombin, including anticoagulant thrombin variants, has been expressed in cultured mammalian host cells such as BHK21 cells (Guinto et al., "Unexpected crucial role of residue 225 in serine proteases", Proc Natl Acad Sci USA 1999 Mar. 2; 96(5): 1852-1857; Cantwell and Di Cera 2000, supra), and in *E. coli* (US Patent Application Publication 2012/0164129 A1). Thrombin prepared in this way is typically expressed as prethrombin-2, which needs to be converted to mature thrombin (or "activated") by treatment with an enzyme, for example by treatment with prothrombinase complex which contains activated factor X, or immobilized ecarin, an enzyme purified from snake venom, or other activators.

Therefore, there exists a need for alternative methods of producing mature recombinant thrombin that do not require additional expensive or inconvenient steps such as refolding reactions (if expressed in bacteria as inclusion bodies), or purification of a thrombin precursor from the media, followed by activation of the precursor to thrombin with an activator.

SUMMARY OF THE INVENTION

The present invention provides methods for producing thrombin using coordinated coexpression systems, and in particular those that use inducible coexpression systems capable of controlled induction of each gene product required for the production of thrombin, and the thrombin produced by these methods.

One embodiment of the invention is a host cell comprising at least one expression construct comprising a polynucleotide sequence encoding a polypeptide selected from the group consisting of (a) a polypeptide comprising the amino acid sequence of the thrombin A chain, wherein the host cell further comprises a polynucleotide sequence encoding the amino acid sequence of the thrombin B chain, and said polynucleotide sequence encoding the amino acid sequence of the thrombin A chain is not contiguous with said polynucleotide sequence encoding the amino acid sequence of the thrombin B chain; (b) a polypeptide comprising the amino acid sequence of the thrombin B chain, wherein the host cell further comprises a polynucleotide sequence encoding the amino acid sequence of the thrombin A chain, and said polynucleotide sequence encoding the amino acid sequence of the thrombin A chain is not contiguous with said polynucleotide sequence encoding the amino acid sequence of the thrombin B chain; and (c) a polypeptide that comprises the amino acid sequences of the thrombin A chain and the thrombin B chain, and is longer than prethombin-2 and shorter than prethrombin-1. In certain embodiments of the invention, at least one expression construct of the host cell comprises an inducible promoter. Another embodiment of the invention is a host cell comprising two or more types of expression constructs, wherein at least one type of expression construct comprises an inducible promoter and a polynucleotide sequence encoding a polypeptide to be transcribed from the inducible promoter; wherein said polypeptide is selected from the group consisting of: (a) preprothrombin; (b) prothrombin; (c) prethrombin-1; (d) prethrombin-2; and (e) fragments of any of (a)-(c) that comprise the amino acid sequences of the thrombin A chain and the thrombin B chain. In certain embodiments of the invention, the expression construct of each type comprises an inducible promoter that is different from the inducible promoter of the expression construct of each other type, or an origin of replication that is different from the origin of replication of the expression construct of each other type.

In certain aspects of the invention, the polypeptide encoded by the expression construct is a polypeptide comprising the amino acid sequence of the thrombin A chain and comprises an amino acid sequence selected from the group consisting of: SEQ ID NO:3 and SEQ ID NO:8, or a polypeptide comprising the amino acid sequence of the thrombin B chain and comprises an amino acid sequence selected from the group consisting of SEQ ID NO:4 and SEQ ID NO:6. In additional embodiments of the invention, the polypeptide comprises a thrombin amino acid sequence variation selected from the group consisting of: E14eA/D141A/E18A; G14mP; R93A/W215A/E217A; T172Y/W215A/E217A; S195A; W215A; W215A/E217A; W215E; W215G; a deletion of residues E146-K149e; W215G/a deletion of residues E146-K149e; W215L; W215V; E217A; and E229K. In further instances of the invention, the polypeptide comprises the thrombin amino acid sequence variation W215A/E217A, which in certain instances is selected from the group consisting of: SEQ ID NO:6 and SEQ ID NO:10. The invention also provides host cells wherein at least one expression construct comprises a polynucleotide sequence encoding a metalloprotease, which in some embodiments is an ecarin polypeptide, and further instances comprises the amino acid sequence of SEQ ID NO:12.

In particular embodiments, the invention provides host cells with expression constructs wherein at least one inducible promoter is an L-arabinose-inducible promoter, or is a propionate-inducible promoter, or is selected from the group consisting of: the araBAD promoter, the prpBCDE promoter, the rhaSR promoter, and the xlyA promoter. In additional instances, each inducible promoter is not a lactose-inducible promoter. Also provided are host cells wherein at least one expression construct further comprises a polynucleotide sequence encoding a transcriptional regulator that binds to an inducible promoter; in certain instances the transcriptional regulator is selected from the group consisting of: AraC, PrpR, RhaR, and Xy1R. In further embodiments of the invention, the polynucleotide sequence encoding the transcriptional regulator and the inducible promoter to which said transcriptional regulator binds are in the same expression construct. Other instances of the invention provide host cells wherein at least one expression construct was produced by a method comprising a step of inserting a polynucleotide sequence into a plasmid selected from the group consisting of: pBAD18, pBAD18-Cm, pBAD18-Kan, pBAD24, pBAD28, pBAD30, pBAD33, pPRO18, pPRO18-Cm, pPRO18-Kan, pPRO24, pPRO30, pPRO33, and pPRO43. Host cells comprising two types of expression constructs are also provided, and in some embodiments, one type of expression construct is produced by a method comprising a step of inserting a polynucleotide sequence into a pBAD24 plasmid, and the other type of expression construct is produced by a method comprising a step of inserting a polynucleotide sequence into a plasmid selected from the group consisting of pPRO33 and pPRO43.

A further aspect of the invention are host cells having an alteration of gene function of at least one gene encoding a transporter protein for an inducer of at least one said inducible promoter, where the gene encoding a transporter protein in some instances is selected from the group consisting of araE, araF, araG, araH, rhaT, xylF, xylG, and xylH. Additionally provided are host cells having a reduced level of gene function of at least one gene encoding a protein that metabolizes an inducer of at least one said inducible promoter and in certain embodiments is selected from the group consisting of araA, araB, araD, prpB, prpD, rhaA, rhaB, rhaD, xylA, and xylB. Other instances of the invention are host cells having a reduced level of gene function of at least one gene encoding a protein involved in biosynthesis of an inducer of at least one said inducible promoter, wherein the gene encoding a protein involved in biosynthesis of an inducer of at least one said inducible promoter is, in particular embodiments, selected from the group consisting of scpA/sbm, argK/ygfD, scpB/ygfG, scpC/ygfH, rmlA, rmlB, rmlC, and rmlD. Host cells are also provided which have an altered gene function of a gene that affects the reduction/oxidation environment of the host cell cytoplasm and which in certain instances is selected from the group consisting of gor and gshB. Additional embodiments of the invention are host cells having a reduced level of gene function of a gene that encodes a reductase, such as trxB. In other instances, the invention provides host cells comprising at least one expression construct encoding at least one disulfide bond isomerase protein, which in some aspects is DsbC, and which in further embodiments is a form of DsbC lacking a signal peptide. Other instances of the invention are host cells comprising at least one polynucleotide encoding Erv1p, and prokaryotic host cells, which in some embodiments are *E. coli*.

The invention also provides an *E. coli* host cell comprising two types of expression constructs, wherein one type of expression construct is produced by a method comprising a step of inserting a polynucleotide sequence into a pBAD24 plasmid, and the other type of expression construct is produced by a method comprising a step of inserting a polynucleotide sequence into a plasmid selected from the group consisting of pPRO33 and pPRO43; and further comprising two or more of the following: (a) a deletion of the araBAD genes; (b) an altered gene function of the araE gene; (c) an altered gene function of the araFGH genes; (d) a lacY(A177C) gene; (e) a reduced gene function of the prpB and prpD genes; (f) a reduced gene function of the sbm/scpA-ygfD/argK-ygfGH/scpBC genes without affecting expression of the ygfI gene; (g) a reduced gene function of the gor and trxB genes; (h) a reduced gene function of the AscG gene; (i) a polynucleotide encoding a form of DsbC lacking a signal peptide; (j) a polynucleotide encoding Erv1p; (k) a polynucleotide encoding protein disulfide isomerase; and (l) a polynucleotide encoding a chaperone. In some embodiments, the host cell has an altered gene function of the araE gene which is the expression of araE from a constitutive promoter, and in other aspects, the host cell comprises a reduced gene function of the sbm/scpA-ygfD/argK-ygfGH/scpBC genes without affecting expression of the ygfI gene; a reduced gene function of the gor and trxB genes; and a polynucleotide encoding a form of DsbC lacking a signal peptide, and in certain embodiments, such host cells further comprise at least one expression construct comprising a polynucleotide sequence encoding a gene product to be transcribed from an inducible promoter.

Additional aspects of the invention are methods of producing thrombin polypeptides, such methods comprising growing a culture of the host cell of claim 1, or growing a culture of the host cell of claim 2 or 3 and adding an inducer of at least one inducible promoter to the culture, which in some instances is propionate. In further embodiments of the invention, the host cell is E. coli. The invention also provides methods further comprising purifying the thrombin polypeptides, which in some aspects comprise a His tag and are purified using a nickel column, and in other embodiments are purified using polyphosphate. Thrombin produced by the methods of the invention is provided, which is some instances is human thrombin, and in certain embodiments has an amino acid sequence comprising the W215A/E217A variation, which can in further instances comprise amino acids 2 through 37 of SEQ ID NO:3 and amino acids 2 through 260 of SEQ ID NO:6, or is aglycosylated. In additional embodiments of the invention, thrombin polypeptides produced by the methods of the invention comprise an A chain that shares at least 80% amino acid identity across at least 30 amino acids of SEQ ID NO:3 and a B chain that shares at least 80% amino acid identity across at least 50 amino acids of SEQ ID NO:4 or SEQ ID NO:6; and in particular instances the resulting thrombin molecule has a discernable level of thrombin activity.

Also provided are kits comprising host cells of the invention, and kits comprising thrombin produced by the methods of the invention.

DETAILED DESCRIPTION OF THE INVENTION

Figure 1:
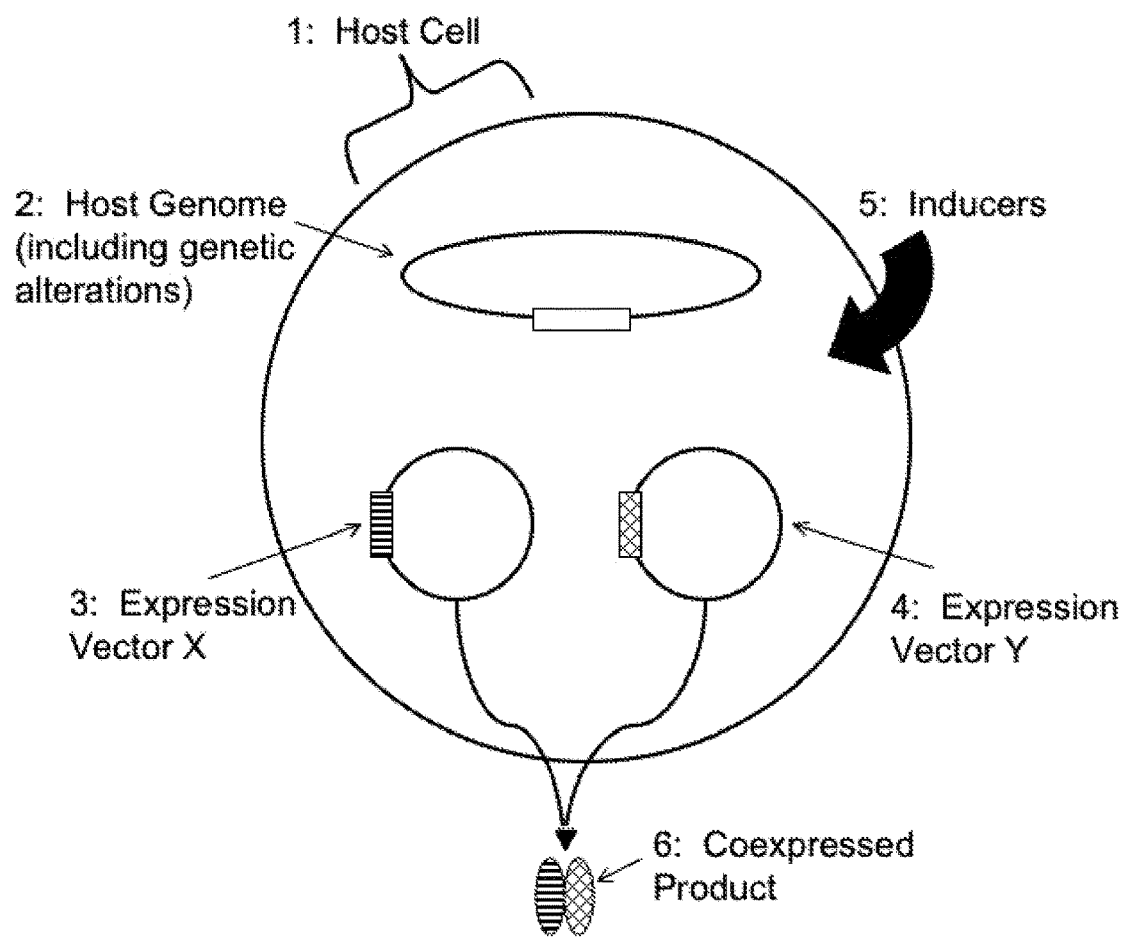
FIG. 1 is a schematic illustration of the inducible coexpression system, which includes a host cell (1), with a genome that preferably contains genetic alterations (2), comprising two different inducible expression vectors (3) and (4), which express different gene products upon application of inducers (5), forming a coexpressed product such as thrombin (6).

The problem of expression of thrombin which does not require expensive or time-consuming additional procedures, such as expression of a thrombin precursor and activation of that precursor to produce thrombin, is addressed by development of the coordinated coexpression systems of the invention.

The embodiments of the invention involve coexpressing thrombin polypeptides, preferably the thrombin A chain and B chain as separate polypeptides, or thrombin precursor forms in conjunction with proteins such as chaperones or proteases, that are useful for the expression of active forms of thrombin.

It is possible to achieve coordinated coexpression of thrombin polypeptides in several ways. The coordinated coexpression of polypeptides is the coexpression of two or more polypeptides in a way that allows for control of the relative levels of the polypeptides that are produced, and preferably for control of the relative levels of the polypeptides as they are being expressed in the cell. As one example of coordinated coexpression, bicistronic (also called discistronic) vectors can be used, in which the coding sequences for each polypeptide are expressed in tandem from a single promoter, with an internal ribosome entry site (IRES) or ribosome binding site (RBS) between the coding sequences allowing for translation of the downstream gene (Mazor et al., "Isolation of full-length IgG antibodies from combinatorial libraries expressed in *Escherichia coli*", Methods Mol Biol 2009; 525: 217-239, xiv; doi: 10.1007/978-1-59745-554-1_11). The use of bicistronic vectors is limited, however, in that both polypeptides are presumed to be expressed at the same level from the common transcript, in a 1:1 ratio, whether or not that is actually the most effective ratio for expression of the desired protein product. There is no easy way to 'fine-tune' the relative expression levels of the polypeptides when using a bicistronic vector approach.

Another well known example of coordinated coexpression is the use of plasmids containing the lac and ara promoters to coexpress different polypeptides. These systems do not induce protein homogeneously across the entire growth culture population in wild-type *E. coli* (Khlebnikov and Keasling, "Effect of lacY expression on homogeneity of induction from the $P_{tac}$ and $P_{trc}$ promoters by natural and synthetic inducers", Biotechnol Prog 2002 May-June; 18(3): 672-674). When expression of the transport proteins for inducers is dependent on the presence of inducer, as is the case for wild-type *E. coli* lac and am systems, the cellular concentration of the inducer must reach a threshold level to initiate the production of transport proteins, but once that threshold has been reached, an uncontrolled positive feedback loop can occur, with the result being a high level of inducer in the cell and correspondingly high levels of expression from inducible promoters: the "all-or-none" phenomenon. Increasing the concentration of the inducer in the growth medium increases the proportion of cells in the population that are in high-expression mode. Although this type of system results in concentration-dependent induction of protein expression at the population scale, and thus some control of the overall relative levels of the polypeptides that are produced, it is suboptimal for expression and production of proteins that require tight control of coexpression at the intracellular level, including those that are toxic, have poor solubility, or require specific relative concentrations of coexpressed polypeptides for other reasons.

Some efforts have been made to address the "all-or-none" induction phenomenon by eliminating inducer-dependent transport of the inducer. One example is having a null mutation in the lactose permease gene (lacYam) and using an alternate inducer of the lac promoter such as IPTG (isopropyl-thio-β-D-galactoside), which can get through the cell membrane to some degree in the absence of a transporter (Jensen et al., "The use of lac-type promoters in control analysis", Eur J Biochem 1993 Jan. 15; 211(1-2): 181-191). Another approach is the use of an arabinose-inducible promoter in a strain deficient in the arabinose transporter genes, but with a mutation in the lactose permease gene, lacY(A117C), that allows it to transport arabinose into the cell (Morgan-Kiss et al., "Long-term and homogeneous regulation of the *Escherichia coli* araBAD promoter by use of a lactose transporter of relaxed specificity", Proc Natl Acad Sci USA 2002 May 28; 99(11): 7373-7377). Even though these developments improve control of the lac and ara promoters when used separately, they cannot be used together, since one requires a null mutation in the lactose permease gene (lacYam), and the other uses a substitution mutation in the lactose permease gene, lacY(A117C).

The preferred coordinated coexpression methods for coexpressing thrombin polypeptides utilize compatible homogeneously inducible promoter systems that are, in some embodiments, activated by different inducers. The advantages of this homogeneously inducible coexpression system include, without limitation: 1) improved compatibility of components within the inducible coexpression system; 2) improved control of thrombin polypeptide coexpression by independently titratable induction; 3) improved expression of thrombin proteins, which are difficult to express due to the requirement of disulfide bond formation, optionally coexpressed with other polypeptides; and 4) streamlined optimization of thrombin polypeptide coexpression.

Thrombin Produced by the Coordinated Coexpression Methods of the Invention.

The term "thrombin polypeptides" refers generally to mammalian thrombin polypeptides, with a particular subset of thrombin polypeptides being primate thrombin polypeptides, such as those having the following UniProtKB database accession numbers: F6QU78 (*Callithrix jacchus*, white-tufted-ear marmoset); G1RVB3 (*Nomascus leucogenys* (*Hylobates leucogenys*), northern white-cheeked gibbon); A0N064 (*Macaca mulatta*, rhesus macaque); G7PQA7 (*Macaca fascicularis*, crab-eating macaque (cynomolgus monkey)); G7NDG8 (*Macaca mulatta*, rhesus macaque); Q5R537 (*Pongo abelii* (*Pongo pygmaeus abelii*), Sumatran orangutan); G3QVP5 (*Gorilla gorilla gorilla*, lowland gorilla); H2Q3I2 (*Pan troglodytes*, chimpanzee); and P00734 (*Homo sapiens*, human). Mammalian thrombin polypeptides share over 80% amino acid identity, and primate thrombin polypeptides over 90% amino acid identity, with the amino acid sequence of human thrombin. The high degree of amino acid sequence conservation between these polypeptides makes it quite easy to determine the amino acid sequences of mammalian thrombin polypeptides that correspond to various forms and variants of human thrombin polypeptides. Therefore, examples and embodiments of the invention described with reference to the human thrombin polypeptide sequence are intended to be applicable to mammalian thrombin polypeptides generally, unless otherwise indicated.

The reference thrombin molecule is the human alpha-thrombin molecule as described by Bode et al. 1989 (infra). Human thrombin has a disulfide bond between the A and B chains, between residues C336 and C482 (amino acid numbering of human preprothrombin, SEQ ID NO:1), and three intrachain disulfide bonds connecting the following residues of the B chain: C391 with C407; C536 with C550; and C564 with C594. The term "thrombin" refers to a mammalian thrombin molecule formed by two polypeptide chains, an A chain and a B chain, and includes variants that differ from the reference mammalian thrombin. The terms "A chain" and "B chain" refer to polypeptides that form thrombin, and thus include variants that differ from the reference mammalian thrombin A chain and/or B chain. Thrombin molecules preferably have a discernable level of one or more activities such as, but not limited to, prothrombin-cleaving activity, protein C activation, fibrinogen-cleaving, and fibrin-clotting activity, as described further herein.

The amino acid sequence of human preprothrombin (from UniProtKB database accession number P00734) has been provided as SEQ ID NO:1. The amino acids that are present in mature thrombin have been numbered according to a few different systems. Table 1 shows part of the amino acid sequence of human preprothrombin (i.e. a portion of SEQ ID NO:1), and the numbering of those amino acids according to (1) their position in the A and B chains of mature thrombin, (2) the numbering system of Bode et al. 1989 (infra), and (3) human preprothrombin (SEQ ID NO:1).

TABLE 1

Sequential amino acid numbering for the amino acids of the A and B chains of mature human thrombin, and the numbering used by Bode et al.[1], with reference to the amino acid sequence of human preprothrombin (SEQ ID NO: 1).

| Mature Thrombin | Amino Acid Residues | Bode et al.[1] Numbering | Amino Acids of SEQ ID NO: 1 |
|---|---|---|---|
| A Chain Amino Acids: | | | |
| 1-8 | TFGSGEAD | 1h-1a | 328-335 |
| 9-22 | CGLRPLFEKKSLED | 1-14 | 336-349 |
| 23-36 | KTERELLESYIDGR | 14a-14m, 15 | 350-363 |
| B Chain Amino Acids: | | | |
| 1-22 | IVEGSDAEIGMSPWQVMLFRKS | 16-36, 36a | 364-385 |
| 23-46 | PQELLCGASLISDRWVLTAAHCLL | 37-60 | 386-409 |
| 47-55 | YPPWDKNFT | 60a-60i | 410-418 |
| 56-73 | ENDLLVRIGKHSRTRYER | 61-77, 77a | 419-436 |
| 74-94 | NIEKISMLEKIYIHPRYNWRE | 78-97, 97a | 437-457 |
| 95-129 | NLDRDIALMKLKKPVAFSDYIHPVCLPDRETAASL | 98-129, 129a-129c | 458-492 |
| 130-154 | LQAGYKGRVTGWGNLKETWTANVGK | 130-149, 149a-149e | 493-517 |
| 155-190 | GQPSVLQVVNLPIVERPVCKDSTRIRITDNMFCAGY | 150-184, 184a | 518-553 |
| 191-196 | KPDEGK | 185-186, 186a-186d | 554-559 |
| 197-216 | RGDACEGDSGGPFVMKSPFN | 187-204, 204a-204b | 560-579 |
| 217-233 | NRWYQMGIVSWGEGCDR | 205-217, 219-221, 221a | 580-596 |
| 234-259 | DGKYGFYTHVFRLKKWIQKVIDQFGE | 222-247 | 597-622 |

[1]Bode et al., "The refined 1.9 Å crystal structure of human α-thrombin: interaction with D-Phe-Pro-Arg chloromethylketone and significance of the Tyr-Pro-Pro-Trp insertion segment", EMBO J 1989 Nov; 8(11): 3467-3475. [Tyr-Pro-Pro-Trp is amino acids 410-413 of SEQ ID NO: 1].

The preprothrombin amino acid sequence represents the full thrombin polypeptide as it is initially expressed; amino acids 1-24 of SEQ ID NO:1 are the signal peptide, and amino acids 25-43 of SEQ ID NO:1 are a propeptide that is removed to form prothrombin (amino acids 44-622 of SEQ ID NO:1). Amino acids 44-198 of SEQ ID NO:1 are removed when prothrombin is cleaved by thrombin to form prethrombin-1 (amino acids 199-622 of SEQ ID NO:1). Amino acids 199-327 of SEQ ID NO:1 are removed when prethrombin-1 is cleaved by activated factor X (Xa) (or other enzymes) to form prethrombin-2 (amino acids 328-622 of SEQ ID NO:1). Finally, prethrombin-2 is cleaved by Xa to form the A chain (also called the light chain) (amino acids 328-363 of SEQ ID NO:1), and the B chain (also called the heavy chain) (amino acids 364-622 of SEQ ID NO:1) of mature thrombin. Examples of the human thrombin A chain and B chain, with N-terminal methionine residues added, are provided as SEQ ID NOs 3 and 4, respectively.

Thrombin polypeptides produced by the methods of the invention can include variations from the wild-type or reference thrombin amino acid sequence for a given species. These variations can be in the A chain or B chain of thrombin, or in both chains. A variety of in vitro assays exist for measuring the activities of thrombin variants, including the ability to cleave prothrombin, fibrinogen, and fibrin; the activation of protein C, and the interaction with PAR1 (Cantwell and Di Cera, "Rational design of a potent anticoagulant thrombin", J Biol Chem 2000 Dec. 22; 275(51): 39827-39830; Epub 2000 Nov. 1). Examples of assays for thrombin activity, including of thrombin- and fibrinogen-cleavage assays, are provided in Example 4. Anticoagulant effects of thrombin variants can also be determined using in vivo assays in experimental animals (Gruber et al., "The thrombin mutant W215A/E217A shows safe and potent anticoagulant and antithrombotic effects in vivo", J Biol Chem 2002 Aug. 2; 277(31): 27581-27584; Epub 2002 Jun. 17). Examples of thrombin polypeptide variants are described below; the amino acid positions of the variations in the thrombin amino acid sequences are given using the numbering system of Bode et al. (supra), unless otherwise indicated.

The double thrombin mutant referred to as W215A/E217A thrombin (or WE-thrombin) is constructed by combining the two single mutations W215A and E217A in the human thrombin molecule [Cantwell, (2000) J. Biol. Chem. 275:39827-39830]. W215A and E217A refer to amino acid residue positions in the thrombin amino acid residue sequence using the position numbers as described in Bode et al. (supra), that correspond to amino acids 590 and 592 of SEQ ID NO:1, respectively. The human thrombin referred to as E-WE-thrombin is WE-thrombin that has been produced in E. coli (US Patent Application Publication 2012/0164129 A1). WE-thrombin has enhanced protein C activating properties, and reduced fibrinogen-cleaving activity, making it a highly anticoagulant thrombin. The R93A/W215A/E217A triple mutant of human thrombin is a thrombin variant in which the heparin-binding R93 residue has been mutated, producing an RWE-thrombin which appears to have a longer half-life than WE-thrombin. The T172Y/W215A/E217A triple mutant of human thrombin is another thrombin variant that can be produced using the methods of the invention. Another type of anticoagulant thrombin is the E229K variant (Leung et al., "Regulation of tissue inflammation by thrombin-activatable carboxypeptidase B (or TAFI)", Adv Exp Med Biol 2008; 632: 61-69).

Some thrombin polypeptide variants comprise altered or novel cleavage sites that promote cleavage of prethrombin-2 by thrombin. Some of these variants comprise changes to the FXa cleavage site between the A and B chains (DGR, amino acids 361 through 363 of SEQ ID NO:1), to make it more like the thrombin cleavage site in preprothrombin (VPR or IPR); these variants all include the G14mP substitution (International Patent Application Publication WO2013/064542 A1; US Patent Application Publication 2006/205041 A1). The E14eA/D141A/E18A triple mutant causes prethrombin-2 to spontaneously convert to thrombin (Pozzi et al., "Crystal structures of prethrombin-2 reveal alternative conformations under identical solution conditions and the mechanism of zymogen activation", Biochemistry 2011 Nov. 29; 50(47): 10195-10202; doi: 10.1021/bi2015019; Epub 2011 Nov. 8; US Patent Application Publication 2013/0309753 A1).

A large number of thrombin polypeptide variants have been characterized by Marino et al., ("Engineering thrombin for selective specificity toward protein C and PAR1", J Biol Chem 2010 Jun. 18; 285(25): 19145-19152; doi: 10.1074/jbc.M110.119875; Epub 2010 Apr. 19), including alanine-substitution mutants at 97 different positions within the thrombin molecule, 19 single-substitution mutants at the W215 position (particularly W215E, W215L, and W215V, and also W215A, W215C, W215D, W215F, etc.), and a double mutant including the W215G substitution mutant and a deletion of residues E146-K149e.

Other thrombin variants include Y225F, Y225I, Y225P (Guinto et al., "Unexpected crucial role of residue 225 in serine proteases", Proc Natl Acad Sci USA 1999 Mar. 2; 96(5): 1852-1857); R221aA, K224A (Dang et al., "Rational engineering of activity and specificity in a serine protease", Nat Biotechnol 1997 February; 15(2): 146-149); H57A, H57S, D102N, G193A, S195A, S195G (US Patent Application Publication 2007/0282095 A1); and M84A (US Patent Application Publication 2013/017591 A1).

The thrombin variant S195A is completely inactive as a serine protease, because the active site serine has been changed to an alanine. This thrombin variant is useful for its anticoagulant properties, which are likely a result of competition with wild-type thrombin.

Thrombin polypeptides produced by the methods of the invention are not limited to the above examples, but can include any type of thrombin polypeptide variant; preferably, thrombin polypeptides produced by the methods of the invention comprise an A chain that shares at least 80% amino acid identity across at least 30 amino acids of SEQ ID NO:3 and a B chain that shares at least 80% amino acid identity across at least 50 amino acids of SEQ ID NO:4 or of SEQ ID NO:6. Preferably, when such thrombin polypeptides, including thrombin polypeptide variants, are produced, the resulting thrombin molecule has a discernable level of thrombin activity as assayed according to one of the methods described in Examples 2 and 4 below.

The methods of the invention are designed to produce thrombin polypeptides that have been correctly folded and/or assembled into functional products, and that have a desired number of disulfide bonds in the desired locations within such thrombin polypeptides (which can be determined by methods such as that of Example 8). The number of disulfide bonds for a gene product such as a polypeptide is the total number of intramolecular and intermolecular bonds formed by that gene product when it is present in a desired functional product. For example, a light chain of a human IgG antibody typically has three disufide bonds (two intramolecular bonds and one intermolecular bond), and a heavy chain of a human IgG antibody typically has seven disufide bonds (four intramolecular bonds and three intermolecular bonds). In some embodiments, thrombin polypeptides are coexpressed with other gene products, such as chaperones, that are beneficial to the production of the thrombin polypeptides. Chaperones are proteins that assist the non-covalent folding or unfolding, and/or the assembly or disassembly, of other gene products, but do not occur in the resulting monomeric or multimeric gene product structures when the structures are performing their normal biological functions (having completed the processes of folding and/or assembly). Chaperones can be expressed from an inducible promoter or a constitutive promoter within an expression construct, or can be expressed from the host cell chromosome; preferably, expression of chaperone protein(s) in the host cell is at a sufficiently high level to produce coexpressed gene products that are properly folded and/or assembled into the desired product. Examples of chaperones present in E. coli host cells are the folding factors DnaK/DnaJ/GrpE, DsbC/DsbG, GroEL/GroES, IbpA/IbpB, Skp, Tig (trigger factor), and FkpA, which have been used to prevent protein aggregation of cytoplasmic or periplasmic proteins. DnaK/DnaJ/GrpE, GroEL/GroES, and ClpB can function synergistically in assisting protein folding and therefore expression of these chaperones in combinations has been shown to be beneficial for protein expression (Makino et al., "Strain engineering for improved expression of recombinant proteins in bacteria", Microb Cell Fact 2011 May 14; 10: 32). When expressing eukaryotic proteins in prokaryotic host cells, a eukaryotic chaperone protein, such as protein disulfide isomerase (PDI) from the same or a related eukaryotic species, is coexpressed or inducibly coexpressed with the desired gene product in certain embodiments of the invention.

There is broad versatility in utilizing the inducible coexpression systems of the present invention in numerous coexpression applications, and in the properties of the products.

Signal Peptides.

Thrombin polypeptides coexpressed by the methods of the invention can contain signal peptides or lack them, depending on whether it is desirable for the thrombin polypeptides to be exported from the host cell cytoplasm into the periplasm, or to be retained in the cytoplasm, respectively. Signal peptides (also termed signal sequences, leader sequences, or leader peptides) are characterized by a stretch of hydrophobic amino acids, approximately five to twenty amino acids long and often around ten to fifteen amino acids in length, that has a tendency to form a single alpha-helix. This hydrophobic stretch is often immediately preceded by a shorter stretch enriched in positively charged amino acids (particularly lysine). Signal peptides that are to be cleaved from the mature polypeptide typically end in a stretch of amino acids that is recognized and cleaved by signal peptidase. Signal peptides can be characterized functionally by the ability to direct transport of a polypeptide, either co-translationally or post-translationally, through the plasma membrane of prokaryotes (or the inner membrane of grain negative bacteria like E. coli), or into the endoplasmic reticulum of eukaryotic cells. The degree to which a signal peptide enables a polypeptide to be transported into the periplasmic space of a host cell like E. coli, for example, can be determined by separating periplasmic proteins from proteins retained in the cytoplasm, using methods such as that provided in Example 9.

Glycosylation.

Thrombin polypeptides coexpressed by the methods of the invention may be glycosylated or unglycosylated. Glycosylated polypeptides are polypeptides that comprise a covalently attached glycosyl group, and include polypeptides comprising all the glycosyl groups normally attached to particular residues of that polypeptide (fully glycosylated polypeptides), partially glycosylated polypeptides, polypeptides with glycosylation at one or more residues where glycosylation does not normally occur (altered glycosylation), and polypeptides glycosylated with at least one glycosyl group that differs in structure from the glycosyl group normally attached to one or more specified residues (modified glycosylation). An example of modified glycosylation is the production of "defucosylated" or "fucosedeficient" polypeptides, polypeptides lacking fucosyl moieties in the glycosyl groups attached to them, by expression of polypeptides in host cells lacking the ability to fucosylate polypeptides. Unglycosylated polypeptides are polypeptides that do not comprise a covalently bound glycosyl group. An unglycosylated polypeptide can be the result of deglycosylation of a polypeptide, or of production of an aglycosylated polypeptide. Deglycosylated polypeptides can be obtained by enzymatically deglycosylating glycosylated polypeptides, whereas aglycosylated polypeptides can be produced by expressing polypeptides in host cells that do not have the capability to glycosylate polypeptides, such as prokaryotic cells or cells in which the function of at least one glycosylation enzyme has been eliminated or reduced. In a particular embodiment, the coexpressed polypeptides are aglycosylated, and in a more specific embodiment, the aglycosylated polypeptides are coexpressed in prokaryotic cells such as *E. coli*.

Other Modifications of Thrombin Polypeptides.

Thrombin polypeptides coexpressed by the methods of the invention may be covalently linked to other types of molecules. Molecules that may be covalently linked to coexpressed thrombin polypeptides, without limiting the scope of the invention, include polypeptides (such as receptors, ligands, cytokines, growth factors, polypeptide hormones, DNA-binding domains, protein interaction domains such as PDZ domains, kinase domains, antibodies, and fragments of any such polypeptides); water-soluble polymers (such as polyethylene glycol (PEG), carboxymethylcellulose, dextran, polyvinyl alcohol, polyoxyethylated polyols (such as glycerol), polyethylene glycol propionaldehyde, and similar compounds, derivatives, or mixtures thereof); and cytotoxic agents (such as chemotherapeutic agents, growth-inhibitory agents, toxins (such as enzymatically active toxins of bacterial, fungal, plant, or animal origin, or fragments thereof), and radioactive isotopes).

In addition, thrombin polypeptides to be coexpressed by the methods of the invention can be designed to include molecular moieties that aid in the purification and/or detection of the thrombin polypeptides. Many such moieties are known in the art; as one example, a thrombin polypeptide can be designed to include a polyhistidine 'tag' sequence—a run of six or more histidines, preferably six to ten histidine residues, and most preferably six histidines—at its N- or C-terminus. The presence of a polyhistidine sequence on the end of a polypeptide allows it to be bound by cobalt- or nickel-based affinity media, and separated from other polypeptides. The polyhistidine tag sequence can be removed by exopeptidases. As another example, fluorescent protein sequences can be expressed as part of a polypeptide gene product, with the amino acid sequence for the fluorescent protein preferably added at the N- or C-terminal end of the amino acid sequence of the polypeptide gene product. The resulting fusion protein fluoresces when exposed to light of certain wavelengths, allowing the presence of the fusion protein to be detected visually. A well-known fluorescent protein is the green fluorescent protein of *Aequorea victoria*, and many other fluorescent proteins are commercially available, along with nucleotide sequences encoding them.

Expression Constructs.

Expression constructs are polynucleotides designed for the expression of one or more gene products of interest, and thus are not naturally occurring molecules. Expression constructs can be integrated into a host cell chromosome, or maintained within the host cell as polynucleotide molecules replicating independently of the host cell chromosome, such as plasmids or artificial chromosomes. An example of an expression construct is a polynucleotide resulting from the insertion of one or more polynucleotide sequences into a host cell chromosome, where the inserted polynucleotide sequences alter the expression of chromosomal coding sequences. An expression vector is a plasmid expression construct specifically used for the expression of one or more gene products. One or more expression constructs can be integrated into a host cell chromosome or be maintained on an extrachromosomal polynucleotide such as a plasmid or artificial chromosome. The following are descriptions of particular types of polynucleotide sequences that can be used in expression constructs for the coexpression of gene products.

Origins of Replication.

Expression constructs must comprise an origin of replication, also called a replicon, in order to be maintained within the host cell as independently replicating polynucleotides. Different replicons that use the same mechanism for replication cannot be maintained together in a single host cell through repeated cell divisions. As a result, plasmids can be categorized into incompatibility groups depending on the origin of replication that they contain, as shown in Table 2.

TABLE 2

Origins of Replication and Representative Plasmids for Use in Expression Constructs [1]

| Incompatibility Group: | Origin of Replication: | Copy Number: | Representative Plasmids (ATCC Deposit No.): |
|---|---|---|---|
| colE1, pMB1 | colE1 | 15-20 | colE1 (ATCC 27138) |
| | pMB1 | 15-20 | pBR322 (ATCC 31344) |
| | Modified pMB1 | 500-700 | pUC9 (ATCC 37252) |
| IncFII, pT181 F, P1, p15A, pSC101, R6K, RK2 [2] | R1(ts) | 15-120 | pMOB45 (ATCC 37106) |
| | p15A | 18-22 | pACYC177 (ATCC 37031); pACYC184 (ATCC 37033); pPRO33 (Addgene 17810) [3] |
| | pSC101 | ~5 | pSC101 (ATCC 37032): pGBM1 (ATCC 87497) |
| | RK2 | 4-7 [2] | RK2 (ATCC 37125) |
| CloDF13 [4] | CloDF13 | 20-40 [4] | pCDFDuet ™-1 (EMD Millipore Catalog No. 71340-3) |
| ColA [4] | ColA | 20-40 [4] | pCOLADuet ™-1 (EMD Millipore Catalog No. 71406-3) |
| RSF1030 [4] | RSF1030 (also called NTP1) | >100 [4] | pRSFDuet ™-1 (EMD Millipore Catalog No. 71341-3) |

Notes for Table 2:
[1] Adapted from www.bio.davidson.edu/courses/Molbio/Protocols/ORIs.html, and Sambrook and Russell, "Molecular Cloning: A laboratory manual", 3rd Ed., Cold Spring Harbor Laboratory Press, 2001.
[2] Kües and Stahl, "Replication of plasmids in gram-negative bacteria", Microbiol Rev 1989 December; 53(4): 491-516.
[3] The pPRO33 plasmid (U.S. Pat. No. 8,178,338 B2; May 15, 2012; Keasling, Jay) is available from Addgene (www.addgene.org) as Addgene plasmid 17810.
[4] openwetware.org/wiki/CH391L/S12/Origins_of_Replication; accessed 3 Aug. 2013.

Origins of replication can be selected for use in expression constructs on the basis of incompatibility group, copy number, and/or host range, among other criteria. As described above, if two or more different expression constructs are to be used in the same host cell for the coexpression of multiple gene products, it is best if the different expression constructs contain origins of replication from different incompatibility groups: a pMB1 replicon in one expression construct and a p15A replicon in another, for example. The average number of copies of an expression construct in the cell, relative to the number of host chromosome molecules, is determined by the origin of replication contained in that expression construct. Copy number can range from a few copies per cell to several hundred (Table 2). In one embodiment of the invention, different expression constructs are used which comprise inducible promoters that are activated by the same inducer, but which have different origins of replication. By selecting origins of replication that maintain each different expression construct at a certain approximate copy number in the cell, it is possible to adjust the levels of overall production of a gene product expressed from one expression construct, relative to another gene product expressed from a different expression construct. As an example, to coexpress subunits A and B of a multimeric protein, an expression construct is created which comprises the colE1 replicon, the ara promoter, and a coding sequence for subunit A expressed from the ara promoter: 'colE1 $P_{ara}$A'. Another expression construct is created comprising the p15A replicon, the ara promoter, and a coding sequence for subunit B: 'p15A-$P_{ara}$-B'. These two expression constructs can be maintained together in the same host cells, and expression of both subunits A and B is induced by the addition of one inducer, arabinose, to the growth medium. If the expression level of subunit A needed to be significantly increased relative to the expression level of subunit B, in order to bring the stoichiometric ratio of the expressed amounts of the two subunits closer to a desired ratio, for example, a new expression construct for subunit A could be created, having a modified pMB1 replicon as is found in the origin of replication of the pUC9 plasmid ('pUC9ori'): pUC9ori-$P_{ara}$-A. Expressing subunit A from a high-copy-number expression construct such as pUC9ori-$P_{ara}$-A should increase the amount of subunit A produced relative to expression of subunit B from p15A-$P_{ara}$-B. In a similar fashion, use of an origin of replication that maintains expression constructs at a lower copy number, such as pSC101, could reduce the overall level of a gene product expressed from that construct. Selection of an origin of replication can also determine which host cells can maintain an expression construct comprising that replicon. For example, expression constructs comprising the colE1 origin of replication have a relatively narrow range of available hosts, species within the Enterobacteriaceae family, while expression constructs comprising the RK2 replicon can be maintained in *E. coli, Pseudomonas aeruginosa, Pseudomonas putida, Azotobacter vinelandii*, and *Alcaligenes eutrophus*, and if an expression construct comprises the RK2 replicon and some regulator genes from the RK2 plasmid, it can be maintained in host cells as diverse as *Sinorhizobium meliloti, Agrobacterium tumefaciens, Caulobacter crescentus, Acinetobacter calcoaceticus*, and *Rhodobacter sphaeroides* (Kües and Stahl, "Replication of plasmids in gram-negative bacteria", Microbiol Rev 1989 December; 53(4): 491-516).

Similar considerations can be employed to create expression constructs for inducible coexpression in eukaryotic cells. For example, the 2-micron circle plasmid of *Saccharomyces cerevisiae* is compatible with plasmids from other yeast strains, such as pSR1 (ATCC Deposit Nos. 48233 and 66069; Araki et al., "Molecular and functional organization of yeast plasmid pSR1", J Mol Biol 1985 Mar. 20; 182(2): 191-203) and pKD1 (ATCC Deposit No. 37519; Chen et al., "Sequence organization of the circular plasmid pKD1 from the yeast *Kluyveromyces drosophilarum*", Nucleic Acids Res 1986 Jun. 11; 14(11): 4471-4481).

Selectable Markers.

Expression constructs usually comprise a selection gene, also termed a selectable marker, which encodes a protein necessary for the survival or growth of host cells in a selective culture medium. Host cells not containing the expression construct comprising the selection gene will not survive in the culture medium. Typical selection genes encode proteins that confer resistance to antibiotics or other toxins, or that complement auxotrophic deficiencies of the host cell. One example of a selection scheme utilizes a drug such as an antibiotic to arrest growth of a host cell. Those cells that contain an expression construct comprising the selectable marker produce a protein conferring drug resistance and survive the selection regimen. Some examples of antibiotics that are commonly used for the selection of selectable markers (and abbreviations indicating genes that provide antibiotic resistance phenotypes) are: ampicillin ($Amp^R$), chloramphenicol ($Cml^R$ or $Cm^R$), kanamycin ($Kan^R$), spectinomycin ($Spc^R$), streptomycin ($Str^R$), and tetracycline ($Tet^R$). Many of the representative plasmids in Table 2 comprise selectable markers, such as pBR322 ($Amp^R$, $Tet^R$); pMOB45 ($Cm^R$, $Tet^R$); pACYC177 ($Amp^R$, $Kan^R$); and pGBM1 ($Spc^R$, $Str^R$). The native promoter region for a selection gene is usually included, along with the coding sequence for its gene product, as part of a selectable marker portion of an expression construct. Alternatively, the coding sequence for the selection gene can be expressed from a constitutive promoter.

Ribosome Binding Site.

For polypeptide gene products, the nucleotide sequence of the region between the transcription initiation site and the initiation codon of the coding sequence of the gene product that is to be inducibly expressed corresponds to the 5' untranslated region ('UTR') of the mRNA for the polypeptide gene product. Preferably, the region of the expression construct that corresponds to the 5' UTR comprises a polynucleotide sequence similar to the consensus ribosome binding site (RBS, also called the Shine-Dalgarno sequence) that is found in the species of the host cell. In prokaryotes (archaea and bacteria), the RBS consensus sequence is GGAGG or GGAGGU, and in bacteria such as *E. coli*, the RBS consensus sequence is AGGAGG or AGGAGGU. The RBS is typically separated from the initiation codon by 5 to 10 intervening nucleotides. In expression constructs, the RBS sequence is preferably at least 55% identical to the AGGAGGU consensus sequence, more preferably at least 70% identical, and most preferably at least 85% identical, and is separated from the initiation codon by 5 to 10 intervening nucleotides, more preferably by 6 to 9 intervening nucleotides, and most preferably by 6 or 7 intervening nucleotides. The ability of a given RBS to produce a desirable translation initiation rate can be calculated at the website salis.psu.edu/software/RBSLibraryCalculatorSearchMode, using the RBS Calculator; the same tool can be used to optimize a synthetic RBS for a translation rate across a 100,000+ fold range (Salis, "The ribosome binding site calculator", Methods Enzymol 2011; 498: 19-42).

Multiple Cloning Site.

A multiple cloning site (MCS), also called a polylinker, is a polynucleotide that contains multiple restriction sites in close proximity to or overlapping each other. The restriction sites in the MCS typically occur once within the MCS sequence, and preferably do not occur within the rest of the plasmid or other polynucleotide construct, allowing restriction enzymes to cut the plasmid or other polynucleotide construct only within the MCS. Examples of MCS sequences are those in the pBAD series of expression vectors, including pBAD18, pBAD18-Cm, pBAD18-Kan, pBAD24, pBAD28, pBAD30, and pBAD33 (Guzman et al., "Tight regulation, modulation, and high-level expression by vectors containing the arabinose PBAD promoter", J Bacteriol 1995 July; 177(14): 4121-4130); or those in the pPRO series of expression vectors derived from the pBAD vectors, such as pPRO18, pPRO18-Cm, pPRO18-Kan, pPRO24, pPRO30, and pPRO33 (U.S. Pat. No. 8,178,338 B2; May 15 2012; Keasling, Jay). A multiple cloning site can be used in the creation of an expression construct: by placing a multiple cloning site 3' to (or downstream of) a promoter sequence, the MCS can be used to insert the coding sequence for a gene product to be coexpressed into the construct, in the proper location relative to the promoter so that transcription of the coding sequence will occur. Depending on which restriction enzymes are used to cut within the MCS, there may be some part of the MCS sequence remaining within the expression construct after the coding sequence or other polynucleotide sequence is inserted into the expression construct. Any remaining MCS sequence can be upstream or, or downstream of, or on both sides of the inserted sequence. A ribosome binding site can be placed upstream of the MCS, preferably immediately adjacent to or separated from the MCS by only a few nucleotides, in which case the RBS would be upstream of any coding sequence inserted into the MCS. Another alternative is to include a ribosome binding site within the MCS, in which case the choice of restriction enzymes used to cut within the MCS will determine whether the RBS is retained, and in what relation to, the inserted sequences. A further alternative is to include a RBS within the polynucleotide sequence that is to be inserted into the expression construct at the MCS, preferably in the proper relation to any coding sequences to stimulate initiation of translation from the transcribed messenger RNA.

Inducible Promoters.

The following is a description of inducible promoters that can be used in expression constructs for coexpression of gene products, along with some of the genetic modifications that can be made to host cells that contain such expression constructs. Examples of these inducible promoters and related genes are, unless otherwise specified, from *Escherichia coli* (*E. coli*) strain MG1655 (American Type Culture Collection deposit ATCC 700926), which is a substrain of *E. coli* K-12 (American Type Culture Collection deposit ATCC 10798). Table 3 lists the genomic locations, in *E. coli* MG1655, of the nucleotide sequences for these examples of inducible promoters and related genes. Nucleotide and other genetic sequences, referenced by genomic location as in Table 3, are expressly incorporated by reference herein. Additional information about *E. coli* promoters, genes, and strains described herein can be found in many public sources, including the online EcoliWiki resource, located at ecoliwiki.net.

Inducible promoters that can be included in expression constructs as part of the inducible coexpression systems of the invention include those that preferably share at least 80% polynucleotide sequence identity (more preferably, at least 90% identity, and most preferably, at least 95% identity) to at least 30 (more preferably, at least 40, and most preferably, at least 50) contiguous bases of a promoter polynucleotide sequence as defined in Table 3, where percent polynucleotide sequence identity is determined using the methods of Example 10. Under 'standard' inducing conditions (see Example 6), preferred inducible promoters have at least 75% (more preferably, at least 100%, and most preferably, at least 110%) of the strength of the corresponding 'wild-type' inducible promoter of *E. coli* K-12 substrain MG1655, as determined using the quantitative PCR method of De Mey et al. (Example 7). Within the expression construct, an inducible promoter is placed 5' to (or 'upstream of') the coding sequence for the gene product that is to be inducibly expressed, so that the presence of the inducible promoter will direct transcription of the gene product coding sequence in a 5' to 3' direction relative to the coding strand of the polynucleotide encoding the gene product.

Arabinose promoter. (As used herein, 'arabinose' means L-arabinose.) Several *E. coli* operons involved in arabinose utilization are inducible by arabinose—araBAD, araC, araE, and araFGH—but the terms 'arabinose promoter' and 'ara promoter' are typically used to designate the araBAD promoter. Several additional terms have been used to indicate the *E. coli* araBAD promoter, such as $P_{ara}$, $P_{araB}$, $P_{araBAD}$, and $P_{BAD}$. The use herein of 'ara promoter' or any of the alternative terms given above, means the *E. coli* araBAD promoter. As can be seen from the use of another term, 'araC-araBAD promoter', the araBAD promoter is considered to be part of a bidirectional promoter, with the araBAD promoter controlling expression of the araBAD operon in one direction, and the araC promoter, in close proximity to and on the opposite strand from the araBAD promoter, controlling expression of the araC coding sequence in the other direction. The AraC protein is both a positive and a negative transcriptional regulator of the araBAD promoter. In the absence of arabinose, the AraC protein represses transcription from $P_{BAD}$, but in the presence of arabinose, the AraC protein, which alters its conformation upon binding arabinose, becomes a positive regulatory element that allows transcription from $P_{BAD}$. The araBAD operon encodes proteins that metabolize L-arabinose by converting it, through the intermediates L-ribulose and L-ribulose-phosphate, to D-xylulose-5-phosphate. For the purpose of maximizing induction of expression from an arabinose-inducible promoter, it is useful to eliminate or reduce the function of AraA, which catalyzes the conversion of L-arabinose to L-ribulose, and optionally to eliminate or reduce the function of at least one of AraB and AraD, as well. Eliminating or reducing the ability of host cells to decrease the effective concentration of arabinose in the cell, by eliminating or reducing the cell's ability to convert arabinose to other sugars, allows more arabinose to be available for induction of the arabinose-inducible promoter. The genes encoding the transporters which move arabinose into the host cell are araE, which encodes the low-affinity L-arabinose proton symporter, and the araFGH operon, which encodes the subunits of an ABC superfamily high-affinity L-arabinose transporter. Other proteins which can transport L-arabinose into the cell are certain mutants of the LacY lactose permease: the LacY(A177C) and the LacY(A177V) proteins, having a cysteine or a valine amino acid instead of alanine at position 177, respectively (Morgan-Kiss et al., "Long-term and homogeneous regulation of the *Escherichia coli* araBAD promoter by use of a lactose transporter of relaxed specificity", Proc Natl Acad Sci USA 2002 May 28; 99(11): 7373-7377). In order to achieve homogenous induction of an arabinose-inducible promoter, it is useful to make transport of arabinose into the cell independent of regulation by arabinose. This can be accomplished by eliminating or reducing the activity of the AraFGH transporter proteins and altering the expression of araE so that it is only transcribed from a constitutive promoter. Constitutive expression of araE can be accomplished by eliminating or reducing the function of the native araE gene, and introducing into the cell an expression construct which includes a coding sequence for the AraE protein expressed from a constitutive promoter. Alternatively, in a cell lacking AraFGH function, the promoter controlling expression of the host cell's chromosomal araE gene can be changed from an arabinose-inducible promoter to a constitutive promoter. In similar manner, as additional alternatives for homogenous induction of an arabinose-inducible promoter, a host cell that lacks AraE function can have any functional AraFGH coding sequence present in the cell expressed from a constitutive promoter. As another alternative, it is possible to express both the araE gene and the araFGH operon from constitutive promoters, by replacing the native araE and araFGH promoters with constitutive promoters in the host chromosome. It is also possible to eliminate or reduce the activity of both the AraE and the AraFGH arabinose transporters, and in that situation to use a mutation in the LacY lactose permease that allows this protein to transport arabinose. Since expression of the lacY gene is not normally regulated by arabinose, use of a LacY mutant such as LacY(A177C) or LacY(A177V), will not lead to the 'all or none' induction phenomenon when the arabinose-inducible promoter is induced by the presence of arabinose. Because the LacY(A177C) protein appears to be more effective in transporting arabinose into the cell, use of polynucleotides encoding the LacY(A177C) protein is preferred to the use of polynucleotides encoding the LacY (A177V) protein.

Propionate Promoter.

The 'propionate promoter' or 'prp promoter' is the promoter for the *E. coli* prpBCDE operon, and is also called $P_{prpB}$. Like the ara promoter, the prp promoter is part of a bidirectional promoter, controlling expression of the prpBCDE operon in one direction, and with the prpR promoter controlling expression of the prpR coding sequence in the other direction. The PrpR protein is the transcriptional regulator of the prp promoter, and activates transcription from the prp promoter when the PrpR protein binds 2-methylcitrate ('2-MC'). Propionate (also called propanoate) is the ion, $CH_3CH_2COO^-$, of propionic acid (or 'propanoic acid'), and is the smallest of the 'fatty' acids having the general formula $H(CH_2)_nCOOH$ that shares certain properties of this class of molecules: producing an oily layer when salted out of water and having a soapy potassium salt. Commercially available propionate is generally sold as a monovalent cation salt of propionic acid, such as sodium propionate ($CH_3CH_2COONa$), or as a divalent cation salt, such as calcium propionate ($Ca(CH_3CH_2COO)_2$). Propionate is membrane-permeable and is metabolized to 2-MC by conversion of propionate to propionyl-CoA by PrpE (propionyl-CoA synthetase), and then conversion of propionyl-CoA to 2-MC by PrpC (2-methylcitrate synthase). The other proteins encoded by the prpBCDE operon, PrpD (2-methylcitrate dehydratase) and PrpB (2-methylisocitrate lyase), are involved in further catabolism of 2-MC into smaller products such as pyruvate and succinate. In order to maximize induction of a propionate-inducible promoter by propionate added to the cell growth medium, it is therefore desirable to have a host cell with PrpC and PrpE activity, to convert propionate into 2-MC, but also having eliminated or reduced PrpD activity, and optionally eliminated or reduced PrpB activity as well, to prevent 2-MC from being metabolized. Another operon encoding proteins involved in 2-MC biosynthesis is the scpA-argK-scpBC operon, also called the sbm-ygfDGH operon. These genes encode proteins required for the conversion of succinate to propionyl-CoA, which can then be converted to 2-MC by PrpC. Elimination or reduction of the function of these proteins would remove a parallel pathway for the production of the 2-MC inducer, and thus might reduce background levels of expression of a propionate-inducible promoter, and increase sensitivity of the propionate-inducible promoter to exogenously supplied propionate. It has been found that a deletion of sbm-ygfD-ygfG-ygfH-ygfI, introduced into *E. coli* BL21(DE3) to create strain JSB (Lee and Keasling, "A propionate-inducible expression system for enteric bacteria", Appl Environ Microbiol 2005 November; 71(11): 6856-6862), was helpful in reducing background expression in the absence of exogenously supplied inducer, but this deletion also reduced overall expression from the prp promoter in strain JSB. It should be noted, however, that the deletion sbm-ygfD-ygfG-ygfH-ygfI also apparently affects ygfI, which encodes a putative LysR-family transcriptional regulator of unknown function. The genes sbm-ygfDGH are transcribed as one operon, and ygfI is transcribed from the opposite strand. The 3' ends of the ygfH and ygfI coding sequences overlap by a few base pairs, so a deletion that takes out all of the sbm-ygfDGH operon apparently takes out ygfI coding function as well. Eliminating or reducing the function of a subset of the sbm-ygfDGH gene products, such as YgfG (also called ScpB, methylmalonyl-CoA decarboxylase), or deleting the majority of the sbm-ygfDGH (or scpA-argK-scpBC) operon while leaving enough of the 3' end of the ygfH (or scpC) gene so that the expression of ygfI is not affected, could be sufficient to reduce background expression from a propionate-inducible promoter without reducing the maximal level of induced expression.

Rhamnose Promoter.

(As used herein, 'rhamnose' means L-rhamnose.) The 'rhamnose promoter' or 'rha promoter', or $P_{rhaSR}$, is the promoter for the *E. coli* rhaSR operon. Like the ara and prp promoters, the rha promoter is part of a bidirectional promoter, controlling expression of the rhaSR operon in one direction, and with the rhaBAD promoter controlling expression of the rhaBAD operon in the other direction. The rha promoter, however, has two transcriptional regulators involved in modulating expression: RhaR and RhaS. The RhaR protein activates expression of the rhaSR operon in the presence of rhamnose, while RhaS protein activates expression of the L-rhamnose catabolic and transport operons, rhaBAD and rhaT, respectively (Wickstrum et al., "The AraC/XylS family activator RhaS negatively autoregulates rhaSR expression by preventing cyclic AMP receptor protein activation", J Bacteriol 2010 January; 192(1): 225-232). Although the RhaS protein can also activate expression of the rhaSR operon, in effect RhaS negatively autoregulates this expression by interfering with the ability of the cyclic AMP receptor protein (CRP) to coactivate expression with RhaR to a much greater level. The rhaBAD operon encodes the rhamnose catabolic proteins RhaA (L-rhamnose isomerase), which converts L-rhamnose to L-rhamnulose; RhaB (rhamnulokinase), which phosphorylates L-rhamnulose to form L-rhamnulose-1-P; and RhaD (rhamnulose-1-phosphate aldolase), which converts L-rhamnulose-1-P to L-lactaldehyde and DHAP (dihydroxyacetone phosphate). To maximize the amount of rhamnose in the cell available for induction of expression from a rhamnose-inducible promoter, it is desirable to reduce the amount of rhamnose that is broken down by catalysis, by eliminating or reducing the function of RhaA, or optionally of RhaA and at least one of RhaB and RhaD. *E. coli* cells can also synthesize L-rhamnose from alpha-D-glucose-1-P through the activities of the proteins RmlA, RmlB, RmlC, and RmlD (also called RfbA, RfbB, RfbC, and RfbD, respectively) encoded by the rmlB-DACX (or rfbBDACX) operon. To reduce background expression from a rhamnose-inducible promoter, and to enhance the sensitivity of induction of the rhamnose-inducible promoter by exogenously supplied rhamnose, it could be useful to eliminate or reduce the function of one or more of the RmlA, RmlB, RmlC, and RmlD proteins. L-rhamnose is transported into the cell by RhaT, the rhamnose permease or L-rhamnose:proton symporter. As noted above, the expression of RhaT is activated by the transcriptional regulator RhaS. To make expression of RhaT independent of induction by rhamnose (which induces expression of RhaS), the host cell can be altered so that all functional RhaT coding sequences in the cell are expressed from constitutive promoters. Additionally, the coding sequences for RhaS can be deleted or inactivated, so that no functional RhaS is produced. By eliminating or reducing the function of RhaS in the cell, the level of expression from the rhaSR promoter is increased due to the absence of negative autoregulation by RhaS, and the level of expression of the rhamnose catalytic operon rhaBAD is decreased, further increasing the ability of rhamnose to induce expression from the rha promoter.

Xylose Promoter.

(As used herein, 'xylose' means D-xylose.) The xylose promoter, or 'xyl promoter', or $P_{xylA}$, means the promoter for the E. coli xylAB operon. The xylose promoter region is similar in organization to other inducible promoters in that the xylAB operon and the xylFGHR operon are both expressed from adjacent xylose-inducible promoters in opposite directions on the E. coli chromosome (Song and Park, "Organization and regulation of the D-xylose operons in Escherichia coli K-12: XylR acts as a transcriptional activator", J Bacteriol. 1997 November; 179(22): 7025-7032). The transcriptional regulator of both the $P_{xylA}$ and $P_{xylF}$ promoters is Xy1R, which activates expression of these promoters in the presence of xylose. The xylR gene is expressed either as part of the xylFGHR operon or from its own weak promoter, which is not inducible by xylose, located between the xylH and xylR protein-coding sequences. D-xylose is catabolized by XylA (D-xylose isomerase), which converts D-xylose to D-xylulose, which is then phosphorylated by XylB (xylulokinase) to form D-xylulose-5-P. To maximize the amount of xylose in the cell available for induction of expression from a xylose-inducible promoter, it is desirable to reduce the amount of xylose that is broken down by catalysis, by eliminating or reducing the function of at least XylA, or optionally of both XylA and Xy1B. The xylFGHR operon encodes XylF, Xy1G, and Xy1H, the subunits of an ABC superfamily high-affinity D-xylose transporter. The xylE gene, which encodes the E. coli low-affinity xylose-proton symporter, represents a separate operon, the expression of which is also inducible by xylose. To make expression of a xylose transporter independent of induction by xylose, the host cell can be altered so that all functional xylose transporters are expressed from constitutive promoters. For example, the xylFGHR operon could be altered so that the xylFGH coding sequences are deleted, leaving XylR as the only active protein expressed from the xylose-inducible $P_{xylF}$ promoter, and with the xylE coding sequence expressed from a constitutive promoter rather than its native promoter. As another example, the xylR coding sequence is expressed from the $P_{xylA}$ or the $P_{xylF}$ promoter in an expression construct, while either the xylFGHR operon is deleted and xylE is constitutively expressed, or alternatively an xylFGH operon (lacking the xylR coding sequence since that is present in an expression construct) is expressed from a constitutive promoter and the xylE coding sequence is deleted or altered so that it does not produce an active protein.

Lactose Promoter.

The term 'lactose promoter' refers to the lactose-inducible promoter for the lacZYA operon, a promoter which is also called lacZp1; this lactose promoter is located at ca. 365603-365568 (minus strand, with the RNA polymerase binding ('-35') site at ca. 365603-365598, the Pribnow box ('-10') at 365579-365573, and a transcription initiation site at 365567) in the genomic sequence of the E. coli K-12 substrain MG1655 (NCBI Reference Sequence NC 000913.2, 11 Jan. 2012). In some embodiments, inducible coexpression systems of the invention can comprise a lactose-inducible promoter such as the lacZYA promoter. In other embodiments, the inducible coexpression systems of the invention comprise one or more inducible promoters that are not lactose-inducible promoters.

TABLE 3

Genomic Locations of E. coli Inducible Promoters and Related Genes [1]

| Promoter or Gene | Genomic Location: | Comments: |
|---|---|---|
| araBAD promoter | [2] (ca. 70165)-70074 (minus strand) | Smith and Schleif [3]: RNA pol [4] binding ('-35') 70110-70104, Pribnow box ('-10') 70092-70085 |
| araBAD operon | 70075-65855 (minus strand) | Smith and Schleif [3]: transcript start 70075, araB ATG 70048; NCBI: araB end of TAA 68348; araA ATG 68337, end of TAA 66835; araD ATG 66550, end of TAA 65855 |
| araC promoter | [2] (ca. 70166)-70241 (plus strand) | Smith and Schleif [3]: RNA pol binding ('-35') 70210-7021, Pribnow box ('-10') 70230-70236 |
| araC gene | 70242-71265 (plus strand) | Miyada [5]: transcript start 70242, araC ATG 70387; NCBI: end of TAA 71265 |
| araE promoter | [2] (ca. 2980349)-2980231 (minus strand) | Stoner and Schleif [6]: CRP binding 2980349-2980312, RNA pol binding ('-35') 2980269-2980264, Pribnow box ('-10') 2980244-2980239 |
| araE gene | 2980230-2978786 (minus strand) | Stoner and Schleif [6]: transcript start 2980230, ATG 2980204; NCBI: end of TGA 2978786 |
| araFGH promoter | [2] (ca. 1984423)-1984264 (minus strand) | Hendrickson [7]: AraC binding ca. 1984423-ca. 1984414 and 1984326-1984317, CRP binding 1984315-1984297, RNA pol binding ('-35') 1984294-1984289, Pribnow box ('-10') 1984275-1984270 |
| araFGH operon | 1984263-1980578 (minus strand) | Hendrickson [7]: transcript start 1984263; NCBI: araF ATG 1984152, end of TAA 1983163; araG ATG 1983093, end of TGA 1981579; araH ATG 1981564, end of TGA 1980578 |

TABLE 3-continued

Genomic Locations of E. coli Inducible Promoters and Related Genes [1]

| Promoter or Gene | Genomic Location: | Comments: |
|---|---|---|
| lacY gene | 362403-361150 (minus strand) | Expressed as part of the lacZYA operon. NCBI: ATG 362403, end of TAA 361150 |
| prpBCDE promoter | [2] ca. 347790- ca. 347870 (plus strand) | Keasling [8]: RNA pol binding ('−24') 347844-347848, Pribnow box ('−12') 347855-347859 |
| prpBCDE operon | (ca. 347871)- 353816 (plus strand) | Keasling [8]: inferred transcript start ca. 347871, prpB ATG 347906; NCBI: prpB end of TAA 348796; prpC ATG 349236, end of TAA 350405; prpD ATG 350439, end of TAA 351890; prpE ATG 351930, end of TAG 353816 |
| prpR promoter | [2] ca. 347789- ca. 347693 (minus strand) | Keasling [8]: CRP binding 347775-347753, RNA pol binding ('−35') 347728-347723, Pribnow box ('−10') 347707-347702 |
| prpR gene | (ca. 347692)- 346081 (minus strand) | Keasling [8]: inferred transcript start ca. 347692, prpR ATG 347667; NCBI: end of TGA 346081 |
| scpA-argK-scpBC (or sbm-ygfDGH) operon | 3058872-3064302 (plus strand) | NCBI: scpA ATG 3058872, end of TAA 3061016; argK ATG 3061009, end of TAA 3062004; scpB ATG 3062015, end of TAA 3062800; scpC ATG 3062824, end of TAA 3064302 |
| rhaBAD promoter | [2] (ca. 4095605)- 4095496 (minus strand) | Wickstrum [9]: CRP binding 4095595-4095580, RNA pol binding ('−35') 4095530-4095525, Pribnow box ('−10') 4095506-4095501 |
| rhaBAD operon | 4095495-4091471 (minus strand) | Wickstrum [9]: transcript start 4095495, rhaB ATG 4095471; NCBI: rhaB end of TGA 4094002; rhaA ATG 4094005, end of TAA 4092746; rhaD ATG 4092295, end of TAA 4091471 |
| rhaSR promoter | [2] (ca. 4095606)- 4095733 (plus strand) | Wickstrum [9]: CRP binding 4095615-4095630, RNA pol binding ('−35') 4095699-4095704, Pribnow box ('−10') 4095722-4095727 |
| rhaSR operon | 4095734-4097517 (plus strand) | Wickstrum [9]: transcript start 4095734, rhaS ATG 4095759; NCBI: rhaS end of TAA 4096595; rhaR ATG 4096669, end of TAA 4097517 |
| rfbBDACX (or rmlBDACX) operon | 2111085-2106361 (minus strand) | NCBI: rfbB GTG 2111085, end of TAA 2110000; rfbD ATG 2110000, end of TAA 2109101; rfbA ATG 2109043, end of TAA 2108162; rfbC ATG 2108162, end of TGA 2107605; rfbX ATG 2107608, end of TGA 2106361 |
| rhaT promoter | [2] (ca. 4098690)- 4098590 (minus strand) | Via [10]: CRP binding 4098690-4098675, RNA pol binding ('−35') 4098621-4098616, Pribnow box ('−10') 4098601-4098596 |
| rhaT gene | 4098589-4097514 (minus strand) | Via [10]: transcript start 4098589, rhaT ATG 4098548; NCBI: rhaT end of TAA 4097514 |
| xylAB promoter | [2] (ca. 3728960)- 3728831 (minus strand) | Song and Park [11]: CRP binding 3728919-3728901, RNA pol binding ('−35') 3728865-3728860, Pribnow box ('−10') 3728841-3728836 |
| xylAB operon | 3728830-3725940 (minus strand) | Song and Park [11]: transcript start 3728830, xylA ATG 3728788; NCBI: xylA end of TAA 3727466; xylB ATG 3727394, end of TAA 3725940 |
| xylFGHR promoter | [2] (ca. 3728961)- 3729091 (plus strand) | Song and Park [11]: RNA pol binding ('−35') 3729058-3729063, Pribnow box ('−10') 3729080-3729085 |
| xylFGHR operon | 3729092-3734180 (plus strand) | Song and Park [11]: transcript start 3729092, xylF ATG 3729154; NCBI: xylF end of TAA 3730146, xylG ATG 3730224, end of TGA 3731765; xylH ATG 3731743, end of TGA 3732924; xylR ATG 3733002, end of TAG 3734180 |
| xylE promoter | [2] ca. 4240482- ca. 4240320 (minus strand) | Davis and Henderson [12]: possible Pribnow box ('−10') 4240354-4240349, possible Pribnow box ('−10') 4240334-4240329 |

TABLE 3-continued

Genomic Locations of *E. coli* Inducible Promoters and Related Genes [1]

| Promoter or Gene | Genomic Location: | Comments: |
|---|---|---|
| xylE gene | (ca. 4240319)-4238802 (minus strand) | Davis and Henderson [12]: inferred transcript start ca. 4240319, xylE ATG 4240277, end of TAA 4238802 |

Notes for Table 3:
[1] All genomic sequence locations refer to the genomic sequence of *E. coli* K-12 substrain MG1655, provided by the National Center for Biotechnology Information (NCBI) as NCBI Reference Sequence NC_000913.2, 11 JAN. 2012.
[2] The location of the 5' (or 'upstream') end of the promoter region is approximated; for 'bidirectional' promoters, a nucleotide sequence location that is approximately equidistant between the transcription start sites is selected as the designated 5' 'end' for both of the individual promoters. In practice, the promoter portion of an expression construct can have somewhat less sequence at its 5' end than the promoter sequences as indicated in the table, or it can have a nucleotide sequence that includes additional sequence from the region 5' (or 'upstream') of the promoter sequences as indicated in the table, as long as it retains the ability to promote transcription of a downstream coding sequence in an inducible fashion.
[3] Smith and Schleif, "Nucleotide sequence of the L-arabinose regulatory region of *Escherichia coli* K12", J Biol Chem 1978 Oct. 10; 253(19): 6931-6933.
[4] 'RNA pol' indicates RNA polymerase throughout the table.
[5] Miyada, et al., "DNA sequence of the araC regulatory gene from *Escherichia coli* B/r", Nucleic Acids Res 1980 Nov. 25; 8(22): 5267-5274.
[6] Stoner and Schleif, "*E. coli* araE regulatory region araE codes for the low affinity L-arabinose uptake protein", GenBank Database Accession X00272.1, revision date 6 JUL. 1989.
[7] Hendrickson et al., "Sequence elements in the *Escherichia coli* araFGH promoter", J Bacteriol 1992 November; 174(21): 6862-6871.
[8] U.S. Pat. No. 8,178,338 B2; May 15, 2012; Keasling, Jay; FIG. 9.
[9] Wickstrum et al., "The AraC/XylS family activator RhaS negatively autoregulates rhaSR expression by preventing cyclic AMP receptor protein activation", J Bacteriol 2010 January; 192(1): 225-232.
[10] Via et al., "Transcriptional regulation of the *Escherichia coli* rhaT gene", Microbiology 1996 July; 142(Pt 7): 1833-1840.
[11] Song and Park, "Organization and regulation of the D-xylose operons in *Escherichia coli* K-12: XylR acts as a transcriptional activator", J Bacteriol. 1997 November; 179(22): 7025-7032.
[12] Davis and Henderson, "The cloning and DNA sequence of the gene xylE for xylose-proton symport in *Escherichia coli* K12", J Biol Chem 1987 Oct. 15; 262(29): 13928-13932.

Expression from Constitutive Promoters.

Expression constructs of the invention can also comprise coding sequences that are expressed from constitutive promoters. Unlike inducible promoters, constitutive promoters initiate continual gene product production under most growth conditions. One example of a constitutive promoter is that of the Tn3 bla gene, which encodes beta-lactamase and is responsible for the ampicillin-resistance (Amp$^R$) phenotype conferred on the host cell by many plasmids, including pBR322 (ATCC 31344), pACYC177 (ATCC 37031), and pBAD24 (ATCC 87399). Another constitutive promoter that can be used in expression constructs is the promoter for the *E. coli* lipoprotein gene, lpp, which is located at positions 1755731-1755406 (plus strand) in *E. coli* K-12 substrain MG1655 (Inouye and Inouye, "Up-promoter mutations in the lpp gene of *Escherichia coli*", Nucleic Acids Res 1985 May 10; 13(9): 3101-3110). A further example of a constitutive promoter that has been used for heterologous gene expression in *E. coli* is the trpLEDCBA promoter, located at positions 1321169-1321133 (minus strand) in *E. coli* K-12 substrain MG1655 (Windass et al., "The construction of a synthetic *Escherichia coli* trp promoter and its use in the expression of a synthetic interferon gene", Nucleic Acids Res 1982 Nov. 11; 10(21): 6639-6657). Constitutive promoters can be used in expression constructs for the expression of selectable markers, as described herein, and also for the constitutive expression of other gene products useful for the coexpression of the desired product. For example, transcriptional regulators of the inducible promoters, such as AraC, PrpR, RhaR, and Xy1R, if not expressed from a bidirectional inducible promoter, can alternatively be expressed from a constitutive promoter, on either the same expression construct as the inducible promoter they regulate, or a different expression construct. Similarly, gene products useful for the production or transport of the inducer, such as PrpEC, AraE, or Rha, or proteins that modify the reduction-oxidation environment of the cell, as a few examples, can be expressed from a constitutive promoter within an expression construct. Gene products useful for the production of coexpressed gene products, and the resulting desired product, also include chaperone proteins, cofactor transporters, etc.

Host Cells.

The inducible coexpression systems of the invention are designed to express multiple gene products; in certain embodiments of the invention, the gene products are coexpressed in a host cell. Examples of host cells are provided that allow for the efficient and cost-effective inducible coexpression of components of multimeric products. Host cells can include, in addition to isolated cells in culture, cells that are part of a multicellular organism, or cells grown within a different organism or system of organisms. In addition, the expression constructs of the inducible coexpression systems of the invention can be used in cell-free systems, such as those based on wheat germ extracts or on bacterial cell extracts, such as a continuous-exchange cell-free (CECF) protein synthesis system using *E. coli* extracts and an incubation apparatus such as the RTS ProteoMaster (Roche Diagnostics GmbH; Mannheim, Germany) (Jun et al., "Continuous-exchange cell-free protein synthesis using PCR-generated DNA and an RNase E-deficient extract", Biotechniques 2008 March; 44(3): 387-391).

Prokaryotic Host Cells.

In some embodiments of the invention, expression constructs designed for coexpression of gene products are provided in host cells, preferably prokaryotic host cells. Prokaryotic host cells can include archaea (such as *Haloferax volcanii, Sulfolobus solfataricus*), Grain-positive bacteria (such as *Bacillus subtilis, Bacillus licheniformis, Brevibacillus choshinensis, Lactobacillus brevis, Lactobacillus buchneri, Lactococcus lactis*, and *Streptomyces lividans*), or Grain-negative bacteria, including Alphaproteobacteria (*Agrobacterium tumefaciens, Caulobacter crescentus, Rhodobacter sphaeroides*, and *Sinorhizobium meliloti*), Betaproteobacteria (*Alcaligenes eutrophus*), and Gammaproteobacteria (*Acinetobacter calcoaceticus, Azoto-* bacter vinelandii, Escherichia coli, Pseudomonas aeruginosa, and Pseudomonas putida). Preferred host cells include Gammaproteobacteria of the family Enterobacteriaceae, such as Enterobacter, Erwinia, Escherichia (including E. coli), Klebsiella, Proteus, Salmonella (including Salmonella typhimurium), Serratia (including Serratia marcescans), and Shigella.

Eukaryotic host cells. Many additional types of host cells can be used for the inducible coexpression systems of the invention, including eukaryotic cells such as yeast (Candida shehatae, Kluyveromyces lactis, Kluyveromyces fragilis, other Kluyveromyces species, Pichia pastoris, Saccharomyces cerevisiae, Saccharomyces pastorianus also known as Saccharomyces carlsbergensis, Schizosaccharomyces pombe, Dekkera/Brettanomyces species, and Yarrowia lipolytica); other fungi (Aspergillus nidulans, Aspergillus niger, Neurospora crassa, Penicillium, Tolypocladium, Trichoderma reesia); insect cell lines (Drosophila melanogaster Schneider 2 cells and Spodoptera frugiperda Sf9 cells); and mammalian cell lines including immortalized cell lines (Chinese hamster ovary (CHO) cells, HeLa cells, baby hamster kidney (BHK) cells, monkey kidney cells (COS), human embryonic kidney (HEK, 293, or HEK-293) cells, and human hepatocellular carcinoma cells (Hep G2)). The above host cells are available from the American Type Culture Collection.

Alterations to Host Cell Gene Functions.

Certain alterations can be made to the gene functions of host cells comprising inducible expression constructs, to promote efficient and homogeneous induction of the host cell population by an inducer. Preferably, the combination of expression constructs, host cell genotype, and induction conditions results in at least 75% (more preferably at least 85%, and most preferably, at least 95%) of the cells in the culture expressing gene product from each induced promoter, as measured by the method of Khlebnikov et al. described in Example 7. For host cells other than E. coli, these alterations can involve the function of genes that are structurally similar to an E. coli gene, or genes that carry out a function within the host cell similar to that of the E. coli gene. Alterations to host cell gene functions include eliminating or reducing gene function by deleting the gene protein-coding sequence in its entirety, or deleting a large enough portion of the gene, inserting sequence into the gene, or otherwise altering the gene sequence so that a reduced level of functional gene product is made from that gene. Alterations to host cell gene functions also include increasing gene function by, for example, altering the native promoter to create a stronger promoter that directs a higher level of transcription of the gene, or introducing a missense mutation into the protein-coding sequence that results in a more highly active gene product. Alterations to host cell gene functions include altering gene function in any way, including for example, altering a native inducible promoter to create a promoter that is constitutively activated. In addition to alterations in gene functions for the transport and metabolism of inducers, as described herein with relation to inducible promoters, and an altered expression of chaperone proteins, it is also possible to alter the carbon catabolite repression (CCR) regulatory system and/or the reduction-oxidation environment of the host cell.

Carbon Catabolite Repression (CCR).

The presence of an active CCR regulatory system within a host can affect the ability of an inducer to activate transcription from an inducible promoter. For example, when a host cell such as E. coli is grown in a medium containing glucose, genes needed for the utilization of other carbon sources, such as the araBAD and prpBCDE operons, are expressed at a low level if at all, even if the arabinose or propionate inducer is also present in the growth medium. There is also a hierarchy of utilization of carbon sources other than glucose: as in the case of the am and prp inducible promoter systems, where the presence of arabinose reduces the ability of propionate to induce expression from the prpBCDE promoter (Park et al., "The mechanism of sugar-mediated catabolite repression of the propionate catabolic genes in Escherichia coli", Gene 2012 Aug. 1; 504(1): 116-121; Epub 2012 May 3). The CCR mechanism of the cell would therefore appear to make it more difficult to use two or more carbon-source inducers in an inducible coexpression system, as the presence of the inducer that is the preferred carbon source would be expected to inhibit induction by less-preferred carbon sources (Lee et al., "Catabolite repression of the propionate catabolic genes in Escherichia coli and Salmonella enterica: evidence for involvement of the cyclic AMP receptor protein", J Bacteriol 2005 April; 187(8): 2793-2800; Park et al., "The mechanism of sugar-mediated catabolite repression of the propionate catabolic genes in Escherichia coli", Gene 2012 Aug. 1; 504(1): 116-121, Epub 2012 May 3). When using the methods of the invention, it was surprisingly the case that no CCR effect was actually observed when inducing expression with L-arabinose and propionate at most concentration levels, and only a slight repressive effect on expression from the prpBCDE promoter was seen at the very highest L-arabinose concentrations.

However, should it be desirable to alter the CCR regulatory system of the host cell, there are some approaches that can achieve that. The Park et al. authors (supra) attempted to relieve the repression of the prp promoter by arabinose, by using either a mutant crp gene that produces an altered cAMP receptor protein that can function independently of cAMP, or a deletion of PTS (phosphotransferase system) genes involved in the regulation of CCR; both approaches were largely unsuccessful. However, the PTS-knockout strain used by the Park et al. authors is based on strain TP2811, which is a deletion of the E. coli ptsHI-crr operon (Hernandez-Montalvo et al., "Characterization of sugar mixtures utilization by an Escherichia coli mutant devoid of the phosphotransferase system", Appl Microbiol Biotechnol 2001 October; 57(1-2): 186-191). Deletion of the entire ptsHI-crr operon has been found to affect total cAMP synthesis more significantly than a deletion of just the crr gene (Levy et al., "Cyclic AMP synthesis in Escherichia coli strains bearing known deletions in the pts phosphotransferase operon", Gene 1990 Jan. 31; 86(1): 27-33). A different approach is to eliminate or reduce the function of ptsG gene in the host cell, which encodes glucose-specific EII A (EII $A^{glc}$), a key element for CCR in E. coli (Kiln et al., "Simultaneous consumption of pentose and hexose sugars: an optimal microbial phenotype for efficient fermentation of lignocellulosic biomass", Appl Microbiol Biotechnol 2010 November; 88(5): 1077-1085, Epub 2010 Sep. 14). Another alteration in the genome of a host cell such as E. coli, which leads to increased transcription of the prp promoter, is to eliminate or reduce the gene function of the ascG gene, which encodes AscG. AscG is the repressor of the beta-D-glucoside-utilization operon ascFB under normal growth conditions, and also represses transcription of the prp promoter; disruption of the AscG coding sequence has been shown to increase transcription from the prp promoter (Ishida et al., "Participation of regulator AscG of the beta-glucoside utilization operon in regulation of the propionate catabolism operon", J Bacteriol 2009 October; 191(19):

6136-6144; Epub 2009 Jul. 24). A further alternative is to increase expression of the transcriptional regulator of promoters inducible by the less-preferred carbon-source inducer, by placing it either under the control of a strong constitutive promoter, or under the control of the more-preferred carbon-source inducer. For example, to increase the induction of genes needed for the utilization of the less-preferred carbon source xylose in the presence of the more-preferred arabinose, the coding sequence for XylR is placed into the E. coli araBAD operon (Groff et al., "Supplementation of intracellular XylR leads to coutilization of hemicellulose sugars", Appl Environ Microbiol 2012 April; 78(7): 2221-2229, Epub 2012 Jan. 27). Host cells comprising inducible coexpression constructs therefore preferably include an increased level of gene function for transcriptional regulators of promoters inducible by the less-preferred carbon-source inducer(s), and an eliminated or reduced gene function for genes involved in the CCR system, such as crr and/or ptsG and/or ascG.

Host Cell Reduction-Oxidation Environment.

Many multimeric gene products, such as antibodies, contain disulfide bonds. The cytoplasm of E. coli and many other cells is normally maintained in a reduced state by the thioredoxin and the glutaredoxin/glutathione enzyme systems. This precludes the formation of disulfide bonds in the cytoplasm, and proteins that need disulfide bonds are exported into the periplasm where disulfide bond formation and isomerization is catalyzed by the Dsb system, comprising DsbABCD and DsbG. Increased expression of the cysteine oxidase DsbA, the disulfide isomerase DsbC, or combinations of the Dsb proteins, which are all normally transported into the periplasm, has been utilized in the expression of heterologous proteins that require disulfide bonds (Makino et al., "Strain engineering for improved expression of recombinant proteins in bacteria", Microb Cell Fact 2011 May 14; 10: 32). It is also possible to express cytoplasmic forms of these Dsb proteins, such as a cytoplasmic version of DsbC ('cDsbC'), that lacks a signal peptide and therefore is not transported into the periplasm. Cytoplasmic Dsb proteins such as cDsbC are useful for making the cytoplasm of the host cell more oxidizing and thus more conducive to the formation of disulfide bonds in heterologous proteins produced in the cytoplasm. The host cell cytoplasm can also be made more oxidizing by altering the thioredoxin and the glutaredoxin/glutathione enzyme systems directly: mutant strains defective in glutathione reductase (gor) or glutathione synthetase (gshB), together with thioredoxin reductase (trxB), render the cytoplasm oxidizing. These strains are unable to reduce ribonucleotides and therefore cannot grow in the absence of exogenous reductant, such as dithiothreitol (DTT). Suppressor mutations (ahpC*) in the gene ahpC, which encodes the peroxiredoxin AhpC, convert it to a disulfide reductase that generates reduced glutathione, allowing the channeling of electrons onto the enzyme ribonucleotide reductase and enabling the cells defective in gor and trxB, or defective in gshB and trxB, to grow in the absence of DTT. A different class of mutated forms of AhpC can allow strains, defective in the activity of gamma-glutamylcysteine synthetase (gshA) and defective in trxB, to grow in the absence of DTT; these include AhpC V164G, AhpC S71F, AhpC E173/S71F, AhpC E171Ter, and AhpC dup162-169 (Faulkner et al., "Functional plasticity of a peroxidase allows evolution of diverse disulfide-reducing pathways", Proc Natl Acad Sci USA 2008 May 6; 105(18): 6735-6740, Epub 2008 May 2). In such strains with oxidizing cytoplasm, exposed protein cysteines become readily oxidized in a process that is catalyzed by thioredoxins, in a reversal of their physiological function, resulting in the formation of disulfide bonds.

Another alteration that can be made to host cells is to express the sulfhydryl oxidase Erv1p from the inner membrane space of yeast mitochondria in the host cell cytoplasm, which has been shown to increase the production of a variety of complex, disulfide-bonded proteins of eukaryotic origin in the cytoplasm of E. coli, even in the absence of mutations in gor or trxB (Nguyen et al., "Pre-expression of a sulfhydryl oxidase significantly increases the yields of eukaryotic disulfide bond containing proteins expressed in the cytoplasm of E. coli" Microb Cell Fact 2011 Jan. 7; 10: 1). Host cells comprising inducible coexpression constructs preferably also express cDsbC and/or Erv1p, are deficient in trxB gene function, are also deficient in the gene function of either gor, gshB, or gshA, and express an appropriate mutant form of AhpC so that the host cells can be grown in the absence of DTT.

Glycosylation.

Host cells can have alterations in their ability to glycosylate polypeptides. For example, eukaryotic host cells can have eliminated or reduced gene function in glycosyltransferase and/or oligo saccharyltransferase genes, impairing the normal eukaryotic glycosylation of polypeptides to form glyco-proteins. Prokaryotic host cells such as E. coli, which do not normally glycosylate polypeptides, can be altered to express a set of eukaryotic and prokaryotic genes that provide a glycosylation function (DeLisa et al., "Glycosylated protein expression in prokaryotes", WO2009089154A2, 2009 Jul. 16).

Available Host Cell Strains with Altered Gene Functions.

To create preferred strains of host cells to be used in the inducible coexpression systems and methods of the invention, it is useful to start with a strain that already comprises desired genetic alterations (Table 4).

TABLE 4

Host Cell Strains

| Strain: | Genotype: | Source: |
|---|---|---|
| E. coli TOP10 | F- mcrA Δ(mrr-hsdRMS-mcrBC) φ80lacZΔM15 ΔlacX74 recA1 araD139 Δ(ara-leu)7697 galU galK rpsL (Str$^R$) endA1 nupG λ- | Invitrogen Life Technologies Catalog nos. C4040-10, C4040-03, C4040-06, C4040-50, and C4040-52 |
| E. coli Origami™ 2 | Δ(ara-leu)7697 ΔlacX74 ΔphoA PvuII phoR araD139 ahpC galE galK rpsL F'[lac$^+$ lacI$^q$ pro] gor522::Tn10 trxB (Str$^R$, Tet$^R$) | Merck (EMD Millipore Chemicals) Catalog No. 71344 |
| E. coli SHuffle ® Express | fhuA2 [lon] ompT ahpC gal λatt::pNEB3-rl-cDsbC (Spec, lacI) ΔtrxB sulA11 R(mcr-73::miniTn10— Tet$^S$)2 [dcm] R(zgb-210::Tn10— Tet$^S$) endA1 Δgor Δ(mcrC-mrr)114::IS10 | New England Biolabs Catalog No. C3028H |

Methods of Altering Host Cell Gene Functions.

There are many methods known in the art for making alterations to host cell genes in order to eliminate, reduce, or change gene function. Methods of making targeted disruptions of genes in host cells such as E. coli and other prokaryotes have been described (Muyrers et al., "Rapid modification of bacterial artificial chromosomes by ET-recombination", Nucleic Acids Res 1999 Mar. 15; 27(6): 1555-1557; Datsenko and Wanner, "One-step inactivation of chromosomal genes in Escherichia coli K-12 using PCR products", Proc Natl Acad Sci USA 2000 Jun. 6; 97(12):

6640-6645), and kits for using similar Red/ET recombination methods are commercially available (for example, the Quick & Easy *E. coli* Gene Deletion Kit from Gene Bridges GmbH, Heidelberg, Germany). In one embodiment of the invention, the function of one or more genes of host cells is eliminated or reduced by identifying a nucleotide sequence within the coding sequence of the gene to be disrupted, such as one of the *E. coli* K-12 substrain MG1655 coding sequences incorporated herein by reference to the genomic location of the sequence, and more specifically by selecting two adjacent stretches of 50 nucleotides each within that coding sequence. The Quick & Easy *E. coli* Gene Deletion Kit is then used according to the manufacturer's instructions to insert a polynucleotide construct containing a selectable marker between the selected adjacent stretches of coding sequence, eliminating or reducing the normal function of the gene. Red/ET recombination methods can also be used to replace a promoter sequence with that of a different promoter, such as a constitutive promoter, or an artificial promoter that is predicted to promote a certain level of transcription (De Mey et al., "Promoter knock-in: a novel rational method for the fine tuning of genes", BMC Biotechnol 2010 Mar. 24; 10: 26). The function of host cell genes can also be eliminated or reduced by RNA silencing methods (Man et al., "Artificial trans-encoded small non-coding RNAs specifically silence the selected gene expression in bacteria", Nucleic Acids Res 2011 April; 39(8): e50, Epub 2011 Feb. 3). Further, known mutations that alter host cell gene function can be introduced into host cells through traditional genetic methods.

Inducible Coexpression Systems of the Invention.

Inducible coexpression systems of the invention involve host cells comprising two or more expression constructs, where the expression constructs comprise inducible promoters directing the expression of gene products, and the host cells have altered gene functions that allow for homogeneous inducible expression of the gene products. FIG. 1 shows a schematic representation of an inducible coexpression system of the invention, with the following components: (1) host cell, (2) host genome (including genetic alterations), (3) an expression vector 'X' comprising an inducible promoter directing expression of a gene product, (4) a different expression vector 'Y' comprising an inducible promoter directing expression of another gene product, (5) chemical inducers of expression, and (6) the multimeric coexpression product.

Figure 2:
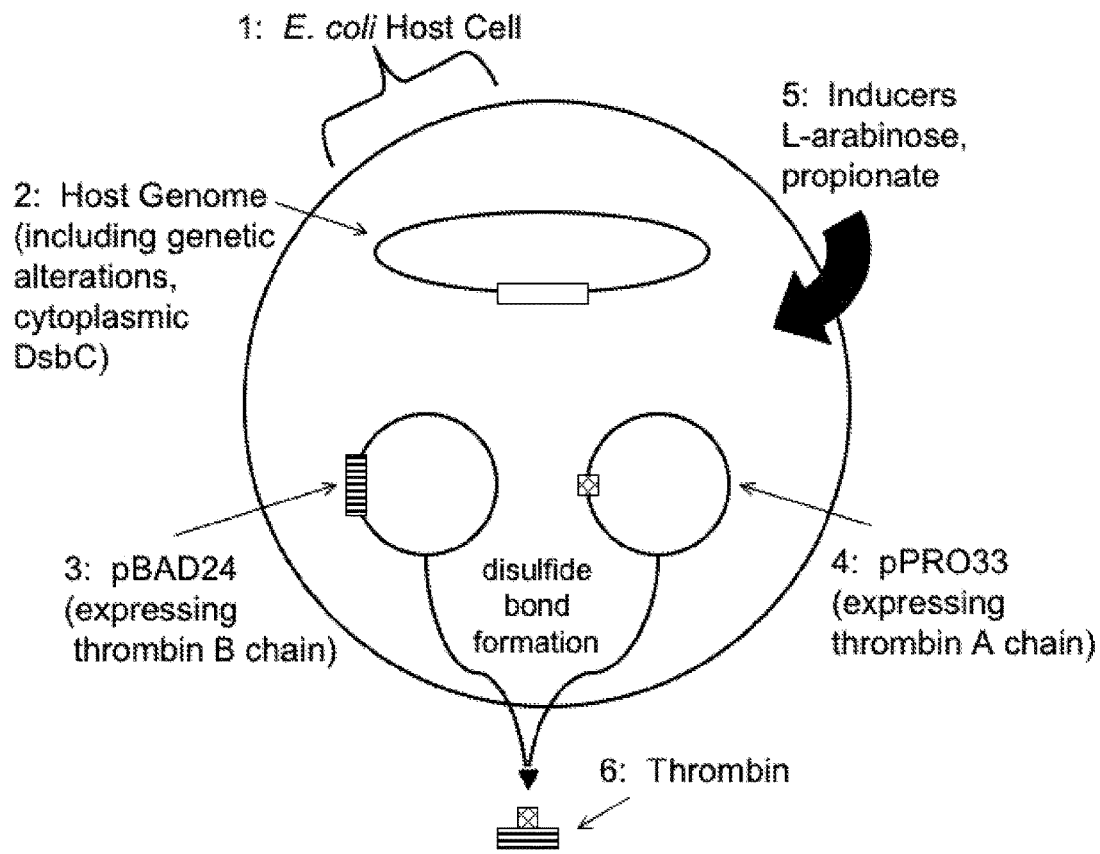
FIG. 2 is a schematic illustration of use of the inducible coexpression system to produce thrombin, in which the E. coli host cell genome (2), among other genetic alterations, encodes a cytoplasmic form of the disulfide isomerase DsbC which lacks a signal peptide; the expression vector pBAD24 (3) provides L-arabinose-inducible expression of the thrombin B chain, and the expression vector pPRO33 (4) provides propionate-inducible expression of the thrombin A chain; forming upon induction with L-arabinose and propionate (5) the thrombin product (6).

FIG. 2 shows a schematic representation of a particular example of an inducible coexpression system of the invention, utilizing the araBAD promoter on a pBAD24 expression vector in combination with a propionate-inducible promoter (prpBCDE promoter) on a pPRO33 expression vector (U.S. Pat. No. 8,178,338 B2; May 15 2012; Keasling, Jay), in an *E. coli* host cell housing the appropriate genomic alterations which allow for homogenously inducible expression. In this manner, tight control and optimization of expression of each component of a multimeric product can be achieved for use in a number of coexpression applications. In this embodiment, the host cell (1) is the Grain-negative bacterium *Escherichia coli*, commonly used in the art for protein expression. The host genome (2) is the genome of the host cell organism with mutations or other alterations that facilitate homogenously inducible protein coexpression, including expression of a cytoplasmic form of the disulfide isomerase DsbC which lacks a signal peptide. In one embodiment, the genomic alterations include both an araBAD operon knockout mutation, and either expression of araE and araFGH from constitutive promoters, or a point mutation in the lacY gene (A117C) in an araEFGH-deficient background, to facilitate homogenous induction of plasmid-based ara promoters with exogenously applied L-arabinose, and also an inactivated proprionate metabolism gene, prpD, to facilitate homogenous induction of plasmid-based propionate promoters with exogenously applied propionate, which is converted to 2-methylcitrate in vivo. Other genomic alterations that are useful for the inducible coexpression system, and may be introduced into the host cell, include without limitation: targeted inactivation of the scpA-argK-scpBC operon, to reduce background expression from the prpBCDE promoter; expression of the transcriptional regulator (prpR) for the less-preferred carbon-source (propionate) from an L-arabinose-inducible promoter such as the araBAD promoter, and/or an eliminated or reduced gene function for genes involved in the CCR system, such as crr and/or ptsG, to avoid suppression by the CCR system of induction by propionate in the presence of L-arabinose; reductions in the level of gene function for glutathione reductase (gor) or glutathione synthetase (gshB), together with thioredoxin reductase (trxB), and/or expression of yeast mitochondrial sulfhydryl oxidase Erv1p in the host cell cytoplasm, to provide a less strongly reducing environment in the host cell cytoplasm and promote disulfide bond formation; increased levels of expression, such as from a strong constitutive promoter, of chaperone proteins such as DnaK/DnaJ/GrpE, DsbC/DsbG, GroEL/GroES, IbpA/IbpB, Skp, Tig (trigger factor), and/or FkpA; and other mutations to reduce endogenous protease activity (such as that of the Lon and OmpT proteases) and recombinase activities.

As shown in FIG. 2, two compatible expression vectors (3, 4) are maintained in the host cell to allow for simultaneous expression (coexpression) of two different gene products. In this embodiment, one expression vector ('L-arabinose-induced expression vector') contains an L-arabinose-induced promoter, and is similar or identical to pBAD or related plasmids in which an araBAD promoter drives expression of an inserted expression sequence cloned into the multiple cloning site (MCS). The L-arabinose-induced expression vector also contains a coding sequence for an antibiotic-resistance gene (such as the Tn3 bla gene, which encodes beta-lactamase and confers resistance to ampicillin) to facilitate selection of host cells (bacterial colonies) which contain an intact expression vector. An origin of replication (ORI) is required for propagation of the plasmid within bacterial host cells. The L-arabinose induced expression plasmid also contains a polynucleotide sequence encoding araC, a transcriptional regulator that allows for L-arabinose induction of the araBAD promotor and through transcriptional repression reduces 'leaky' background expression in the non-induced state. The other expression vector ('propionate-induced expression vector') is similar or identical to pPRO or related plasmids, in which a propionate-induced promoter drives expression of an inserted expression sequence cloned into the multiple cloning site (MCS). The plasmid also contains a coding sequence for an antibiotic-resistance gene (such as the cat gene, encoding chloramphenicol acetyltransferase, which confers resistance to chloramphenicol) to facilitate selection of host cells which contain an intact expression vector. An origin of replication (ORI) is required for propagation of the plasmid within bacterial host cells. In addition, the propionate-induced expression vector contains a polynucleotide sequence encoding prpR, a transcriptional regulator that allows for propionate (2-methylcitrate) induction of the prpBCDE promotor and reduces 'leaky' background expression in the non-induced state. To facilitate separate titration of induction, plasmid compatibility, and copropagation of the expression vectors, it is useful for the expression vectors to contain promoters responsive to different inducers, compatible origins of replication, and different antibiotic-resistance markers. In one embodiment of the invention, a pBAD24 or related expression vector (pMB1 or 'pBR322' ORI, Amp$^R$) containing an L-arabinose-inducible araBAD promoter is combined in a host cell with a pPRO33 or related expression vector (p 15A ORI, Cm$^R$) containing a propionate-inducible prpBCDE promoter. The expression vectors are co-propagated and maintained using growth medium supplemented with ampicillin and chloramphenicol. In one embodiment, one expression vector comprises a polynucleotide sequence encoding the A chain of thrombin, and the other expression vector comprises a polynucleotide sequence encoding the B chain of thrombin, each coding sequence cloned in-frame into the MCS of the respective expression vector. For production of certain gene products, coding sequence optimization for the host organism (including adjustment for codon bias and GC-content, among other considerations) will determine the coding sequences to be inserted into the expression constructs of the coexpression system.

Referring again to FIG. 2, coexpression of the thrombin A and B chains is induced by inexpensive exogenously applied chemical metabolites, L-arabinose and propionate (5). The level of induction of expression of each thrombin polypeptide is independently titrated with its own chemical inducer, thereby facilitating optimization of protein coexpression. This is useful for expression of protein complexes and proteins that require a binding partner for stabilization, and may facilitate expression of otherwise difficult to express proteins, such as those with poor solubility or cellular toxicity. In this example, upon induction, thrombin A and B chains are each separately expressed, then the proteins join and form interchain disulfide bonds (within the cytoplasm of the bacterial host) which allows the formation and stabilization of thrombin. Proteins can be directed to various compartments of the host organism. For example, in *E. coli* the protein can be expressed in the cytoplasm, cell membrane, periplasm, or secreted into the medium. After an appropriate incubation time, cells and media are collected, and the total protein extracted, which includes the coexpressed product, thrombin (6). After extraction, the desired product can be purified using a number of methods well known in the art depending on the nature of the gene products produced in the coexpression system (for example liquid chromatography). In the example shown in FIG. 2, the desired product (thrombin) is purified.

Example 1

Figure 3:
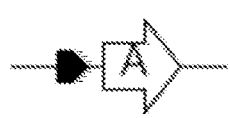
FIG. 3. is a schematic diagram of portions of various expression constructs useful for the coexpression of thrombin polypeptides. Each diagram indicates the location of an inducible promoter (rightward-pointing chevron, black: prpBCDE promoter, gray: araBAD promoter), and the polypeptide expressed from that inducible promoter. A: thrombin A chain; B: thrombin B chain; downward-pointing arrows: ecarin cleavage site; asterisks: location of the W215A and E217A mutations within the B chain.
Figure 3:
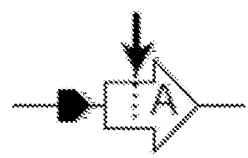
Figure 3:
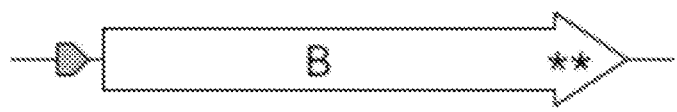
Figure 3:
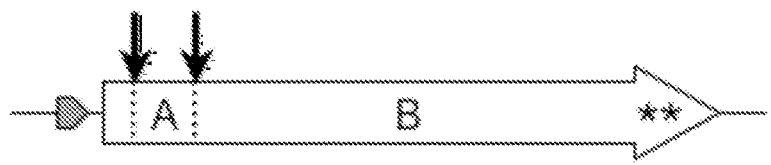
Figure 3:
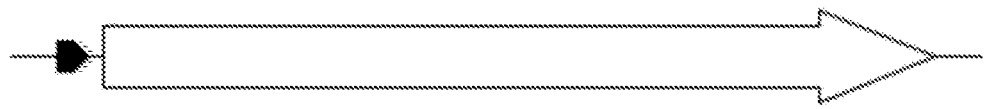

Inducible Coexpression of Thrombin A and B Chains to Produce Thrombin in Bacterial Cells
A. Construction of Thrombin Expression Vectors Three different coexpression arrangements were planned for the expression of human thrombin, in which the inducible coexpression system would be used to control the relative expression levels of two polypeptides in an *E. coli* host cell. Schematic representations of these expression constructs are shown in FIG. 3. The expression vectors used in these experiments are the pBAD24 vector, obtained from the American Type Culture Collection (ATCC) as ATCC 87399, which has the nucleotide sequence shown in GenBank Database Accession No. X81837.1 (25 Oct. 1995); and the pPRO33 vector, obtained from the University of California (Berkeley, Calif.), which has the nucleotide sequence (an updated version) shown in SEQ ID NO:13.

In the first approach, the human thrombin A chain, and the human thrombin B chain containing the W215A E217A mutations ('WE-B'), would be expressed from separate expression constructs, with expression of the A chain from the propionate-inducible prpBCDE promoter in the pPRO33 expression vector, and expression of the WE-B chain from the L-arabinose-inducible araBAD promoter in the pBAD24 expression vector. As described above, the amino acid sequences of the thrombin A chain, B chain, and the WE-B chain, with N-terminal methionine residues, are provided as SEQ ID NOs 3, 4, and 6, respectively. Amino acids 2 through 37 of SEQ ID NO:3; amino acids 2 through 260 of SEQ ID NO:4; and amino acids 2 through 260 of SEQ ID NO:6 are the amino acid sequences of the human thrombin A chain, B chain, and WE-B chain, respectively.

The second arrangement of coexpression constructs is similar to the first, with the thrombin A and WE-B chains separately coexpressed as described above, and in which the A chain further comprises an additional 14 amino acids (including an N-terminal methionine) at its N-terminal end. This extended A chain is referred to as the 'A+ polypeptide', with its amino acid sequence provided as SEQ ID NO:8. The additional residues on the N-terminus of the A chain (amino acids 2-14 of SEQ ID NO:8) generally correspond to a portion of the preprothrombin, prothrombin, and prethrombin-1 amino acid sequences (amino acids 315 to 327 of SEQ ID NO:1) that is N-terminal to the A chain, except that the Asn 325 and Pro 326 residues of SEQ ID NO:1 have been altered to Asp and Gly, respectively, to create a DGR cleavage site that can be recognized by ecarin. Inducible coexpression of the A+ and WE-B chains produces a thrombin protein in which the N-terminal end of the A+ polypeptide can be cleaved by ecarin, either in vitro or through coexpression of ecarin in vivo, to create human thrombin where the A chain has its native N-terminal Thr residue.

In the third set of coexpression constructs, the A+ and WE-B chains are expressed contiguously, from the araBAD promoter in the pBAD24 expression vector, as part of one expression construct; the amino acid sequence of the thrombin A+/WE-B polypeptide is provided as SEQ ID NO:10. The mature form of the ecarin polypeptide (SEQ ID NO:12) is coexpressed, from the prpBCDE promoter in the pPRO33 expression vector, along with the thrombin A+/WE-B polypeptide. This produces a human thrombin A+/WE-B polypeptide, which is similar to WE-prethrombin-2 but with the additional 14 amino acids at its N-terminal end, as described for the A+ polypeptide. The thrombin A+/WE-B polypeptide can be cleaved by ecarin at two locations—the engineered ecarin cleavage site within the A+ sequence that releases the native A chain N-terminus, and the ecarin cleavage site between the A and B chains—with ecarin cleavage at both locations producing a human thrombin protein with the native N-terminal residues on both the A and B chain.

The coding sequences used in these expression constructs were optimized for expression in *E. coli* by DNA2.0 (Menlo Park, Calif.), according to the methods of Welch et al. ("Design parameters to control synthetic gene expression in *Escherichia coli*", PLoS One 2009 Sep. 14; 4(9): e7002; doi: 10.1371/journal. pone.0007002), and were also synthesized by DNA2.0. The regions of the optimized coding sequences that encode the polypeptides to be coexpressed are as follows: nucleotides 21 through 131 of SEQ ID NO:2 encode human thrombin A chain, SEQ ID NO:3; nucleotides 21 through 800 of SEQ ID NO:5 encode human thrombin WE-B chain, SEQ ID NO:6; nucleotides 21 through 170 of SEQ ID NO:7 encode human thrombin A+ polypeptide, SEQ ID NO:8; nucleotides 21 through 947 of SEQ ID NO:9 encode human thrombin A+/WE-B polypeptide, SEQ ID NO:10; and nucleotides 21 through 1301 of SEQ ID NO:11 encode mature *Echis carinatus* ecarin, SEQ ID NO:12. In addition to the optimized coding sequences, these nucleotide sequences all contain a ribosome binding site at nucleotides 7 through 13 of SEQ ID NOs 2, 5, 7, 8, and 11, utilize a TAA termination codon, and have a variety of restriction sites flanking the optimized coding sequences on both sides, including an NheI site 5' to both the ribosome binding site and the coding sequence, and a SalI site 3' of the TAA termination codon.

To create the expression constructs shown in FIG. 3, the optimized coding sequences and the pPRO33 and pBAD24 vectors were digested with NheI and SalI. The desired insert fragments and cut vectors were gel purified, then ligated using 100 ng vector DNA and a 1:3 molar ratio of vector: insert. The resulting pPRO33_A, pPRO33_A+, pBAD_WE-B, pBAD_A+/WE-B, and pPRO33_ecarin expression constructs were transformed into BL21 cells using the heat-shock method: 2.5 microliters of ligated DNA were added to 25 microliters of thawed BL21 cells and incubated on ice for 30 minutes, then at 42 degrees C. for 10 seconds, reincubated on ice for five minutes, then 0.475 mL SOC medium was added and the cells were grown for one hour at 37 degrees C. with shaking at 250 RPM, then pelleted at 3800×g, resuspended in 0.1 mL supernatant, and plated. The BL21 cells transformed with the various expression constructs were used to prepare DNA of the expression constructs, using either miniprep or midiprep methods. To confirm inclusion of the inserts, the expression constructs were generally digested with NheI and SalI, except for pPRO33_A and pPRO33_A+; the inserts are small, so these constructs were digested with XhoI (which cuts 325 nucleotides upstream of the NheI site) and SalI. The nucleotide sequences of the expression constructs are provided as SEQ ID NO:14 (pPRO33_A), SEQ ID NO:15 (pPRO33_A+), SEQ ID NO:16 (pBAD_WE-B), SEQ ID NO:17 (pBAD_A+/WE-B), and SEQ ID NO:18 (pPRO33_ecarin).

It is also possible to use expression vectors other than those listed above when preparing expression constructs for the production of thrombin polypeptides by inducible coexpression methods. For example, the A chain of thrombin could be expressed using the pBAD24 vector, and the B chain using the pPRO33 vector. As another alternative, a modified pPRO vector can be utilized: pPRO43 (SEQ ID NO:19) is also used for expressing polypeptides of interest from the propionate-inducible prpBCDE promoter. In pPRO43 the nucleotide sequence encoding the transcriptional activator prpR has been optimized for expression in *E. coli* by DNA2.0 (Menlo Park, Calif.) as described above, including the RBS and other sequences upstream of the prpR coding sequence. The pPRO43 vector also has only one HindIII restriction site, which is in the multiple cloning site (MCS), in contrast with pPRO33 which has two HindIII sites, one in the MCS and a second in the prpR coding sequence.

B. Transformation of the *E. coli* ASE(DGH) Cell Line with Thrombin Expression Constructs The thrombin expression constructs were co-transformed into *E. coli* ASE(DGH) cells in the following three sets of pairs, to create host cells to be used in the coexpression of thrombin: (1) pPRO33_A (SEQ ID NO:14) and pBAD_WE-B (SEQ ID NO:16); (2) pPRO33_A+(SEQ ID NO:15) and pBAD_WE-B (SEQ ID NO:16); and (3) pBAD_A+/WE-B (SEQ ID NO:17) and pPRO33_ecarin (SEQ ID NO:18). The expression constructs were transformed into *E. coli* ASE(DGH) cells using the heat-shock method described above, except that the heat-shock step was performed for 20 seconds in all cases, and the pPRO33_A & pBAD_WE-B and pPRO33_A+/WE-B & pBAD_ecarin co-transformations were reincubated on ice for only two minutes.

The *E. coli* ASE(DGH) cells were derived from *E. coli* SHuffle® Express cells, and their genotype can be expressed as: *E. coli* SHuffle® Express ΔaraBAD Δsbm-ygfDGH ΔaraEp::J23104. The *E. coli* ASE(DGH) cells were produced as follows: deletions and alterations were made in the *E. coli* SHuffle® Express host cell genome by Gene Bridges GmbH (Heidelberg, Germany) using a recombineering method, described as deletion by counterselection, that seamlessly removes genomic sequences. A deletion of the host cell araBAD operon was made to reduce arabinose catabolism by the host cell, so that more of the arabinose inducer will be available for induction of a coexpressed gene product from an expression construct comprising the araBAD promoter. This deletion removes 4269 basepairs of the araBAD operon, corresponding to position 70,135 through 65,867 (minus strand) of the *E. coli* genome (positions within genomic nucleotide sequences are all given as in Table 3), so that most of the native araBAD promoter through all but a few codons of the AraD coding region are removed. The nucleotide sequence (minus strand) around the deletion junction (position 70,136|position 65,866) is: TTAT|TACG. Another deletion was made within the sbm-ygfDGH (also called scpA-argK-scpBC) operon, eliminating the function of genes involved in the biosynthesis of 2-methylcitrate, to increase sensitivity of the host cell's propionate-inducible promoter to exogenously supplied propionate. The sbm-ygfDGH deletion removes 5542 basepairs (position 3,058,754 through 3,064,295 of the *E. coli* genome), taking out the sbm-ygfDGH promoter and all of the operon except for the last codon of the ygfH coding sequence, while leaving the adjacent ygfI coding sequence and stop codon intact. The nucleotide sequence (plus strand) around the deletion junction (position 3,058,753|position 3,064,296) is: ACAA|GGGT. In addition to these deletions made in the *E. coli* SHuffle® Express host cell genome, Gene Bridges GmbH introduced a point mutation in the genomic rpsL gene coding sequence, which extends on the minus strand from position 3,472,574 through 3,472,200, changing the A at position 3,472,447 to a G, altering the codon for Lys43 to a codon for Arg, which results in a streptomycin-resistant phenotype when the mutant rpsL-Arg43 gene is expressed. Another alteration to the host cell genome, allowing for more tightly controlled inducible expression as described above, is to make the araE promoter constitutive rather than responsive to arabinose. Most of the native araE promoter, including CRP-cAMP and AraC binding sites, was removed by deleting 97 basepairs (position 2,980,335 through 2,980,239 (minus strand)) and replacing that sequence with the 35-basepair sequence of the constitutive J23104 promoter (SEQ ID NO:20; the nucleotide sequence of J23104 was obtained from the partsregistry.org website, parts.igem.org/Main_Page). The resulting junction site sequences within the altered araE promoter are: TGAA|TTGA . . . TAGC|TTCA.

C. Inducible Coexpression of Thrombin A and B Chains in Bacterial Cells

The inducible coexpression system was used to produce thrombin, and specifically WE-thrombin, in bacterial cells. *E. coli* ASE(DGH) cells comprising the WE-thrombin pPRO33_A and pBAD24_WE-B expression constructs were stabbed and cultured overnight in 6 mL LB+cam+amp+ 0.2% glucose at 37 degrees C. with shaking at 250RPM. The culture was expanded and diluted to OD600=0.025 in 60 mL LB+cam+amp+0.2% glucose and grown at 37 degrees C. with shaking at 250RPM for about 5 hours. When the cells reached OD600=0.66, cells were pelleted and resuspended in 80 mL M9 medium without a carbon source to a density equal to OD600=0.5. Cells in M9 were distributed into 10×6-mL aliquots, to which were added varying amounts of propionate and L-arabinose inducer, as follows: Sample 1: uninduced, 0% arabinose, 0 mM propionate; Sample 2: 0.00001% arabinose, 5 mM propionate; Sample 3: 0.0001% arabinose, 5 mM propionate; Sample 4: 0.0001% arabinose, 20 mM propionate; Sample 5: 0.001% arabinose, 0.5 mM propionate; Sample 6: 0.001% arabinose, 5 mM propionate; Sample 7: 0.001% arabinose, 20 mM propionate; Sample 8: 0.01% arabinose, 5 mM propionate; Sample 9: 0.01% arabinose, 20 mM propionate; Sample 10: 0.1% arabinose, 20 mM propionate. Samples were induced for 5 hours at 30 degrees C. with shaking at 250RPM.

Figure 4:
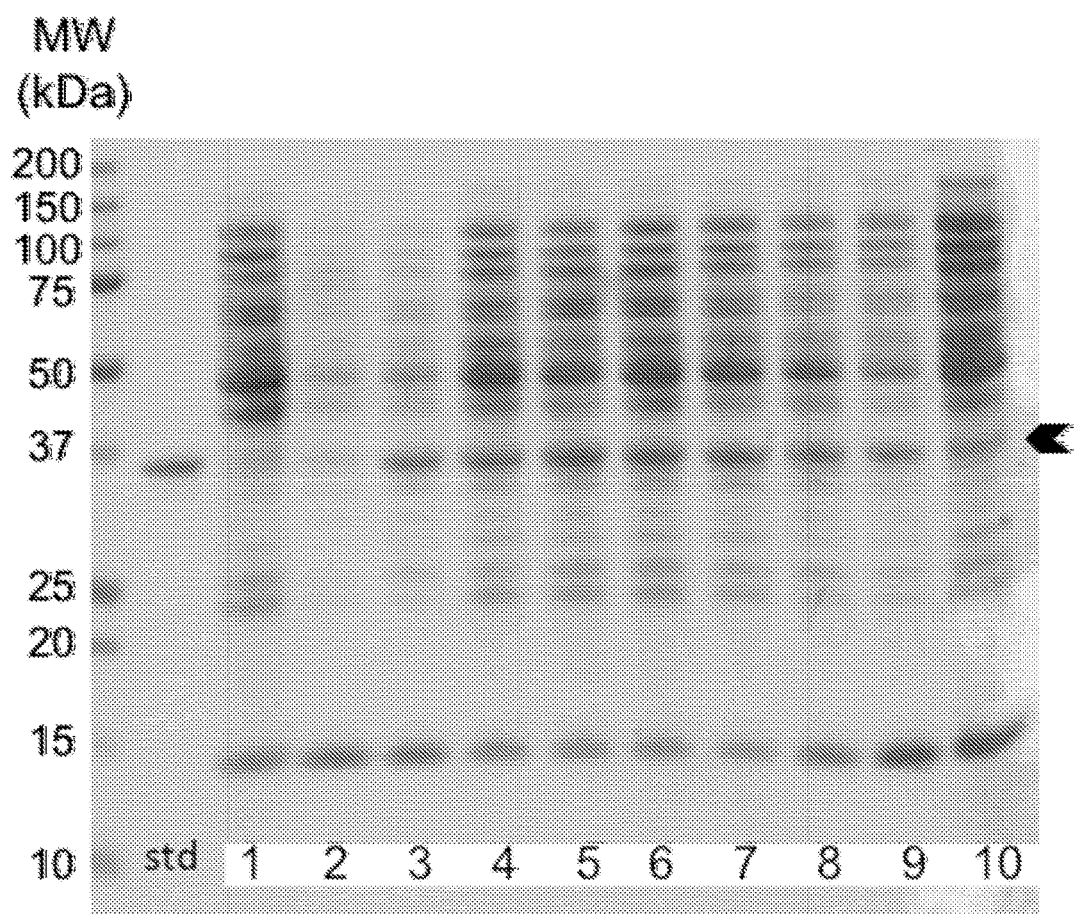
FIG. 4 shows the result of coexpression of thrombin A and WE-B chains in bacterial cells. The soluble protein extracts from cells containing both the pPRO33_A and pBAD24_WE-B inducible expression constructs, either uninduced or with expression induced by different combinations of inducer concentrations, were separated by gel electrophoresis under native (non-reducing) conditions on a NuPAGE® Novex® 10% Bis-Tris gel. MW: Molecular weight markers; std: human thrombin; Lane 1: uninduced, 0% arabinose, 0 mM propionate; Lane 2: 0.00001% arabinose, 5 mM propionate; Lane 3: 0.0001% arabinose, 5 mM propionate; Lanes 4: 0.0001% arabinose, 20 mM propionate; Lane 5: 0.001% arabinose, 0.5 mM propionate; Lane 6: 0.001% arabinose, 5 mM propionate; Lane 7: 0.001% arabinose, 20 mM propionate; Lane 8: 0.01% arabinose, 5 mM propionate; Lane 9: 0.01% arabinose, 20 mM propionate; Lane 10: 0.1% arabinose, 20 mM propionate. Arrow indicates a protein band (thrombin comprising A and WE-B chains) at 33.8 kDa; this band is present in the induced cells, but is absent in the uninduced cells.

After 5 hours of induction, cell suspensions from each sample were divided into 4×1.2 mL aliquots, and the cells were pelleted by centrifugation at 4300 RPM for 5 minutes at 25 degrees C., and stored dry in the freezer after removal of the supernatants. One pellet (corresponding to 1.2 mL culture) of each induction condition was thawed and resuspended in 40.5 microliters PBS, then cOmplete Protease Inhibitor Cocktail (Roche Diagnostics Corp., Indianapolis Ind.) solution and lysozyme solution were added to a final concentration of ~1.25× protease cocktail and 1.0 mg/mL lysozyme in 45 microliters PBS, and lysis was allowed to proceed for 30 minutes on ice. (Samples to be assayed for thrombin activity are lysed without protease inhibitors as described in the section below.) Lysates were clarified by centrifugation at 20,000×g for 30 minutes at 4 degrees C.; the supernatant was retained for analysis by gel electrophoresis. A NuPAGE® Novex® 10% Bis-Tris gel (Life Technologies, Grand Island, N.Y.) was loaded with the samples as described above, and was run in SDS-MES at 220V, 45 minutes, under non-reducing conditions. The gel was stained using RAPIDstain™ (G-Biosciences). As shown in FIG. 4, a protein band (thrombin comprising A and WE-B chains) migrates at 33.8 kDa on the gel; this band is absent in the uninduced cells, and present in the induced cells, with the greatest band intensity shown in samples induced with intermediate concentrations of arabinose.

D. Western Blot

E. coli ASE(DGH) cells comprising sets of WE-thrombin expression constructs—either pPRO33_A and pBAD24_WE-B, or pPRO33_A+ and pBAD24_WE-B—were cultured in LB+cam+amp media, then pelleted and resuspended in M9+cam+amp to a final concentration of OD600=0.55. Both groups of cells were induced in 20 mM propionate, 0.001% L-arabinose, and separate batches of both groups of cells were incubated during induction under two different conditions: 16 degrees C. for 24 hours with shaking at 300 RPM, and 30 degrees C. for 5 hours with shaking at 250 RPM.

Each induction was aliquoted into 2× or 4×1.2-mL aliquots and 4×50-mL aliquots, all of which were pelleted at 3800×g for five minutes. Supernatants (culture medium from the induction) and dry pellets were stored at −80 degrees C. for subsequent analysis. Pellets corresponding to a 1.2-mL aliquot per condition were thawed and brought to a final volume of 50 microliters in PBS with 1.0 mg/mL lysozyme, 3.6 units benzonase (product number 70746, Novagen/EMD Millapore, Billerica, Mass.), and lysis was allowed to proceed on ice for 30 minutes. Lysates were spun at 20,000×g for 30 minutes at 4 degrees C. The samples shown in the following table were prepared using NuPAGE® 10× Reducing Agent (Life Technologies) and 4×XT Sample Buffer (Bio-Rad, Hercules Calif.), then incubated at 95 degrees C. for five minutes prior to loading.

| Lane | Protein | Induction Conditions/Fraction (or Source) | Volume (microliters) |
| --- | --- | --- | --- |
| MW | Protein Standards | (MagicMark™ XP, Life Technologies) | 4 |
| std | E-WE-thrombin | (Thrombin standard, 0.1 mg/mL) | 2 |
| 1 | A/B thrombin | 30 degrees, 5 hours/cell lysate | 10 |
| 2 | A/B thrombin | 30 degrees, 5 hours/culture medium | 13 |
| 3 | A+/B thrombin | 30 degrees, 5 hours/cell lysate | 10 |
| 4 | A+/B thrombin | 30 degrees, 5 hours/culture medium | 13 |
| 5 | A/B thrombin | 16 degrees, 24 hours/cell lysate | 10 |
| 6 | A/B thrombin | 16 degrees, 24 hours/culture medium | 13 |
| 7 | A+/B thrombin | 16 degrees, 24 hours/cell lysate | 10 |
| 8 | A+/B thrombin | 16 degrees, 24 hours/culture medium | 13 |

Figure 5:
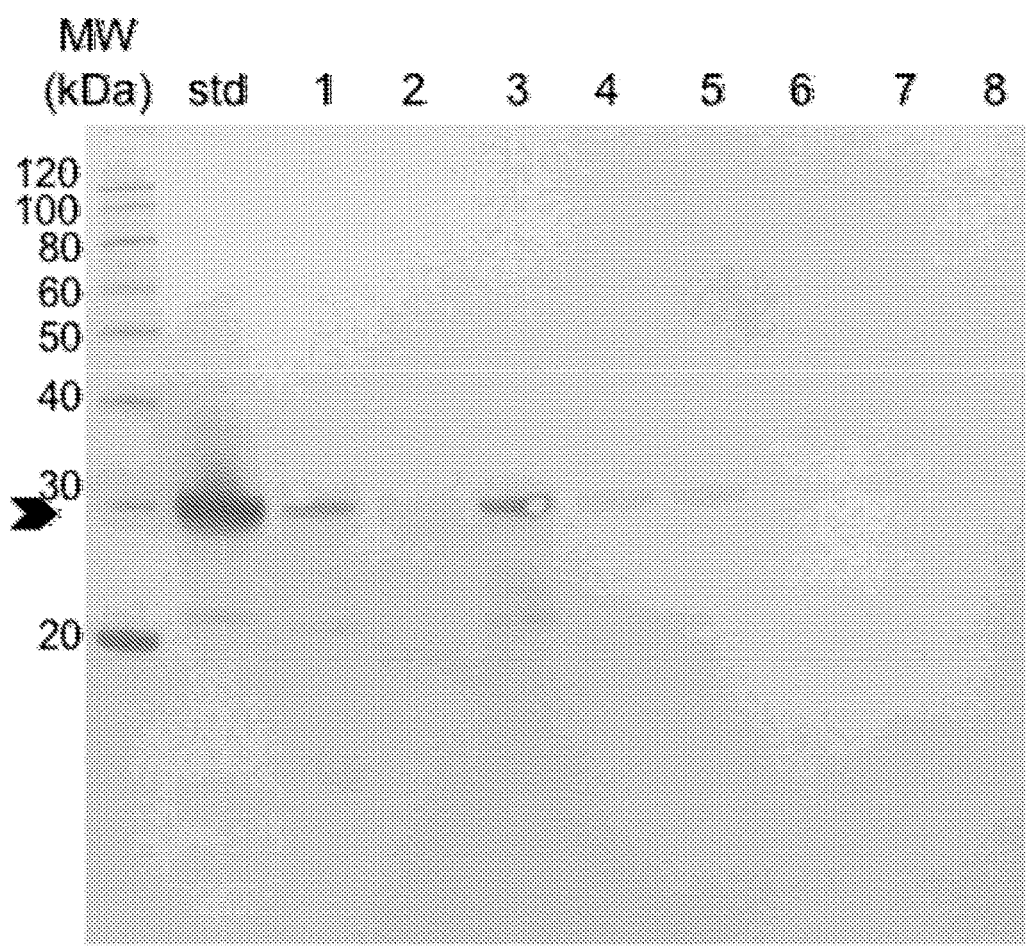
FIG. 5 is a western blot showing the result of coexpression of thrombin A and WE-B chains, and of thrombin A chains with an added N-terminal ecarin cleavage site (thrombin A+) with thrombin WE-B chains in bacterial cells. Cells containing the pPRO33_A and pBAD24_WE-B inducible expression constructs, or the pPRO33_A+ and pBAD24_WE-B inducible expression constructs, were induced to coexpress thrombin with 0.001% L-arabinose and 20 mM propionate, and were induced either for 5 hours at 30 degrees C., or for 24 hours at 16 degrees C. The induced cells were pelleted and lysed, and the culture medium from the induction was also saved for analysis. Soluble proteins from the cell lysate and from the culture medium of the various samples were separated by gel electrophoresis under reducing conditions on a NuPAGE® Novex® 10% Bis-Tris gel, then transferred to a nitrocellulose membrane and visualized using a mouse monoclonal anti-thrombin antibody, and an alkaline phosphate conjugated anti-mouse secondary antibody. The results show the presence of the thrombin WE-B chain (29.7 kDa) in both the cell lysates and the culture medium from the co-induced host cells. MW: MagicMark™ XP protein standards; std: WE-thrombin standard; Lane 1: A/WE-B thrombin, cell lysate, 5 hours, 30 degrees C.; Lane 2: A/WE-B thrombin, culture medium, 5 hours, 30 degrees C.; Lane 3: A+/WE-B thrombin, cell lysate, 5 hours, 30 degrees C.; Lane 4: A+/WE-B thrombin, culture medium, 5 hours, 30 degrees C.; Lane 5: A/WE-B thrombin, cell lysate, 24 hours, 16 degrees C.; Lane 6: A/WE-B thrombin, culture medium, 24 hours, 16 degrees C.; Lane 7: A+/WE-B thrombin, cell lysate, 24 hours, 16 degrees C.; Lane 8: A+/WE-B thrombin, culture medium, 24 hours, 16 degrees C.

A NuPAGE® Novex® 10% Bis-Tris gel (Life Technologies) was loaded with the above samples and run under reducing conditions in SDS-MES running buffer, at 4 degrees C. and 220V, then transferred onto nitrocellulose membrane at 30V, 1 hour in 1× NuPAGE®Transfer Buffer with 10% MeOH. The nitrocellulose membrane was blocked and immunodetection was done using Novex® reagents according to the manufacturer's protocol; the primary antibody was 1:750 monoclonal mouse anti-thrombin (product number HYB 109-03-02, Pierce Antibodies/Thermo Fisher Scientific, Waltham, Mass.), and the secondary antibody was Novex® Alk-Phos. Conjugated Anti-Mouse Antibody solution (Life Technologies). The results are shown in FIG. 5; bands corresponding in size to the B chain of thrombin (29.7 kDa), which is expected to run separately from the A chain under reducing conditions, are seen in the lane with the thrombin standard, and in the lanes loaded with soluble proteins from the cell lysate (lanes 1, 3, 5, and 7). There is also some thrombin B chain detected in the culture medium (lanes 2, 4, 6, and 8), without any purification or concentration steps having been performed. These results indicate that it should be possible to use the inducible coexpression methods of the invention to purify thrombin either from lysed host cells or directly from the culture medium of induced host cells.

Example 2

Assay of the Activity of Coexpressed Thrombin—Recovery of Active Thrombin from the Culture Medium A. Preparation of Thrombin-Containing Samples E. coli ASE(DGH) cells comprising sets of WE-thrombin expression constructs—either pPRO33_A and pBAD24_WE-B, or pPRO33_A+ and pBAD24_WE-B— were induced as described in the section above under 'Western blot'. In that experiment, 50-mL aliquots were made of those cells, and the cell pellets and supernatants from those aliquots were stored at −80 degrees C. In addition, a non-induced control sample was prepared by growing E. coli ASE(DGH) cells comprising the pPRO33_A and pBAD24_WE-B expression constructs in LB+0.2% glucose+cam+amp, then pelleting them, removing the supernatant, and resuspending them in M9+0.2% glucose. After incubating the cells for 5 hours at 30 degrees C. with shaking at 250 RPM, the cells were divided into 4×50-mL aliquots, and pelleted at 3800×g for 5 minutes at 25 degrees C.

The cell samples that were lysed included one cell pellet (corresponding to 50 mL culture) for each combination of expression vectors (A/WE-B, A+/WE-B) with each induction condition (30 degrees C. for 5 hours, 16 degrees C. for 24 hours), plus a cell pellet from the no-induction control sample. The cell pellets were each thawed in a 50-mL tube, to which was added 2.5 mL Formulation Buffer (20 mM NaCitrate, 150 mM NaCl, 0.1% Polysorbate 80, pH 6.0, filter sterilized), including 1.0 mg/mL lysozyme and 150 units benzonase (product number 70746, Novagen/EMD Millapore, Billerica, Mass.). The pellets were resuspended and lysis proceeded on ice for 30 minutes, then the lysates were clarified by centrifugation at 20,000×g for 30 minutes at 4 degrees C. The lysates were flash-frozen in an ethanol/dry ice bath and stored at −80 degrees C.

B. Enzyme Capture Assay: Capture of Thrombin Using the Extracellular Domains of Thrombomodulin and Chromogenic Assay for Thrombin Activity Thrombin binds readily to the N-terminal region of thrombomodulin, which is found in recombinant human soluble thrombomodulin (rhs-TM), also called ART-123, which comprises the extracellular domain of thrombomodulin and is glycosylated (Kishida et al., "Study on complex formation between recombinant human thrombomodulin fragment and thrombin using surface plasmon resonance", Am J Hematol 2000 March; 63(3): 136-140). ART-123 has been found to readily adhere to plastic. A method of purifying thrombin takes advantage of this property: in general, a soluble polypeptide comprising the thrombomodulin extracellular domain, such as rhs-TM/ART-123, is immobilized on a solid substrate such as plastic or glass beads in a column, and a solution containing thrombin is passed through the beads under conditions suitable for binding. After an optional wash step, the thrombin is eluted from the column.

The binding of thrombin by the extracellular domain of thrombomodulin also provides the basis for a sensitive assay of thrombin activity. The wells of a 96-well, flat bottom, clear microplate (catalog number 12565501, Thermo Fisher Scientific, Waltham, Mass.) were coated with 100 microliters of 50 micrograms/mL soluble thrombomodulin (rhs-TM/ART-123) in carbonate/bicarbonate buffer pH 7.6 (catalog number 21851, Sigma-Aldrich, St. Louis, Mo.). The plate was stored covered at 4 degrees C. overnight for two nights. The thrombomodulin solution was removed and the plates were blocked with 3% BSA-TBST20(TBS plus Tween 20) for 45 minutes at room temperature. The block was then removed and the wells were washed three times with 150 microliters TBS, flicking and blotting between each wash (this step may not be important).

A standard curve to calibrate the assay was prepared using serial dilutions of purified thrombin (e.g., wild-type human thrombin) in sample dilution buffer (e.g., TBS, 0.01% Tween 20). Incubation was at RT or 37° C. (minutes to hours range; for very dilute standards incubation may proceed for up to a week). The absorbed samples/enzymes were removed by flick and blot. The plate was then washed five times with 150 microliters of TBS, flicking and blotting between each wash to reduce enzymes and contaminants that were not specifically bound to wells. In these experiments, there were no preservatives in the samples, but it may beneficial to add reversible enzyme inhibitors (e.g., benzamidine, 1-20 mM) to all samples (e.g., added to samples in sample dilution buffer) to prevent inactivation of thrombin proteins by inhibitors or by autocatalysis of thrombin in the sample.

The samples that were tested correspond to the samples run on the western blot described in Example 1 above and shown in FIG. 5; abbreviated designators for these samples are L_AB16C, L_AB30C, L_A+B16C, L_A+B30C, M_AB16C, M_AB30C, M_A+B16C, and M_A+B30C, where 'L' indicates a cell lysate and 'M' indicates the culture medium. In addition, the tested samples included the following positive controls: human alpha-thrombin (catalog number RP-43100, Thermo Fisher Scientific) and E-WE thrombin lot #21112-5 (Aronora, Inc.), and the negative controls 'END' (the E. coli-produced, non-induced, control cell-lysate sample described above). The culture medium samples M_AB16C, M_AB30C, M_A+B16C, and M_A+B30C were concentrated with a spin filter protein concentrator for a 20-ml swing bucket (MAP003C36 3K, Pall Corp., Port Washington, N.Y.), according to the manufacturer's instructions. The prepared samples were added to the wells of the thrombomodulin-coated plate, 100 microliters of sample/well. Although not done in this experiment, it may be useful to dilute the samples into a sample buffer (e.g., TBS, 0.01% Tween 20) for consistency in binding rates.

The chromogenic substrate S-2366 (D-Phe-Pip-Arg-p-nitroanilide, Chromogenix, Milan, Italy) was diluted to 0.8 mM with 50 mM Tris-HCl pH 8.3, and 100 microliters of the substrate solution was added to each well carefully to avoid bubbles. The concentration of S-2366 can vary in a broad range (e.g., 0.4 mM to 4 mM), and the S-2366 substrate solution may contain some azide (e.g., 0.05%) and EDTA (20 mM) to prevent bacteria and fungi from growing in the wells.

The method for the determination of thrombin enzyme activity is based on the difference in absorbance (optical density) between the pNA formed between two readings. The formation of pNA increases the color development (absorbance) over time at 405 nm, and is proportional to the captured enzyme activity. Development of color (yellow) can take minutes (as for wild-type thrombin at picomolar or higher concentration) to weeks (as for mutant thrombins, or thrombins at femtomolar or lower concentration). The microplate is stored in a wet chamber, sealed to prevent evaporation and changes in substrate volume in the wells when long reading times are required. The limit of detection for wild-type thrombin appears to be single digit low femtomolar (fM) or even lower (attomolar). There is no theoretical limit, as the assay, when well done, can detect a single enzyme molecule, provided the substrate has a lower autocatalytic rate.

The plate reader (Versa Max with SoftMax Pro 5.0, Molecular Devices, Sunnyvale, Calif.) was set to measure absorbance at 405 nm at 37 degrees C. Absorbance was measured at two time points, at 1 day and at 4 days of incubation. Even though the unpurified experimental samples were below the lowest absorbance point used to generate the standard curve for assay calibration, the non-induced negative control sample ("END") was even lower (OD 405=0.000 at day 1 and 0.000 at day 4), while the positive controls showed significant levels of activity: E-WE thrombin 0.01 mg/ml (OD 405=0.179 at day 1 and 1.853 at day 4); human thrombin 0.001 mg/ml (OD 405=0.569 at day 1 and 1.673 at day 4).

Example 3

Purification of Coexpressed Thrombin

A. Purification of Thrombin Fusion Polypeptides Using Protein Tags

The addition of a 6×His-SUMO protein tag to the N-terminal end of the thrombin B-chain coding sequence can assist in purification of the coexpressed thrombin protein. In one example, expression constructs are prepared, one which encodes a SUMO-thrombin A chain fusion polypeptide, and the other a 6×His-SUMO-thrombin B chain fusion polypeptide. These expression constructs are coexpressed, the resulting thrombin protein is purified using the 6×His tag on the B chain, and then the SUMO tags are cleaved from both the A and B chains by SUMO protease. This procedure results in a thrombin protein with the native N-terminal residues on both the A and B chains. In a preferred embodiment of this method, the SUMO protease polypeptides are also fusion proteins comprising 6×His tags, allowing for a two-step purification: in the first step, the coexpressed 6×His-tagged thrombin is purified by binding to a nickel column, followed by elution from the column. In the second step, the SUMO tags on the purified thrombin are cleaved by the 6×His-tagged SUMO protease, and the SUMO protease-thrombin reaction mixture is run through a second nickel column, which retains the SUMO protease but allows the untagged thrombin to flow through.

B. Chromatographic Methods

Thrombin can be purified using standard size-exclusion chromatography methods. It is also possible to purify thrombin by ion-exchange chromatography, for example on a MonoS-FPLC column by using a linear gradient of 0.05-0.5 M NaCl in 5 mM MES, pH 6 at room temperature. Alternatively, FPLC can be performed using Resource Q and S columns with a linear gradient from 0.05 to 0.5 M choline chloride, 5 mM MES, pH 6, at room temperature.

C. Purification of Thrombin Using Heparin

A 1-mL heparin column (GE HealthCare Life Sciences, Piscataway, N.J.) is prepared by washing with 5 mL 20% EtOH, followed by 10 mL binding buffer (10 mM NaPO4, pH 7.1). A positive control sample, WE-thrombin, is diluted in binding buffer to a concentration of 0.01 mg/mL Samples are loaded onto the column at a flow rate of about 0.5 mL/min and flow-through is kept for analysis. Samples are taken and tested for protein using the Bradford colorimetric assay. The column is washed in 10 mL binding buffer and samples are taken periodically to determine whether the wash contains protein. The column is eluted using 2M NaCl in binding buffer. Fractions are taken in 0.25 mL volumes and the Bradford assay shows that most thrombin protein comes off between 0.75 and 1.0 mL of elution, with some following in the 1-1.25-mL fraction.

In an alternative method, protein samples are diluted in binding buffer and loaded onto a 5-mL heparin column (GE Healthcare Life Sciences) at 3 mL/minute. Bound protein is extensively washed with 100 mM NaCl, 10 mM Tris pH 8 at 25 degrees C. before elution with a linear gradient of 100 mM to 1 M NaCl in 10 mM Tris, pH 8 at 25 degrees C. Fractions with $OD_{280}$ greater than 0.1 are combined, concentrated and applied to a detoxi-gel column to remove endotoxins. Concentration of the protein are determined by taking the $OD_{280}$. The extinction coefficient of recombinant E-WE thrombin at 280 nm is 1.83 $M^{-1}$ $cm^{-1}$.

Alternatively, a solution containing thrombin (routinely 105 mL) is applied to a column (2.6×15 cm) of heparin-Sepharose 6 Fast Flow (GE HealthCare Life Sciences) previously equilibrated using 0.025 M citrate buffer plus 0.15 M NaCl, pH 7.3, at 4 degrees C. The column is first washed exhaustively with the equilibration buffer and then with 0.025 M citrate buffer plus 0.45 M NaCl, pH 7.3. Elution is performed with a 0.025 M citrate buffer plus 2.5 M NaCl, pH 7.3.

D. Purification of Thrombin Using Immobilized Polyphosphate

The use of polyphosphate to purify thrombin arises from its ability to bind with high affinity to thrombin, without binding to prothrombin (Mutch et al., "Polyphosphate binds with high affinity to exosite II of thrombin", J Thromb Haemost 2010 March; 8(3): 548-555; doi: 10.1111/j.1538-7836.2009.03723.x; Epub 2009 Dec. 11). Polyphosphate (polyP, sold under the name "sodium phosphate glass" and available from Sigma (St. Louis, Mo., USA)) of mean polymer lengths 75+($polyP_{75}$) is immobilized onto porous zirconia beads: 250 mg zirconia beads are incubated with 10 mg/ml $polyP_{75}$ in water for 20 hours at 37 degrees C., washed with distilled water, blocked with 10% BSA for 15 hours at ambient temperature, then dried in vacuum at 80 degrees C. for 2 hours. Control beads are treated with water and BSA only. To purify a small amount of thrombin for assays, polyP-zirconia beads (10 mg dry weight) are washed twice with Binding Buffer (50 mM Tris-HCl pH 7.5, 50 mM NaCl, 0.1% BSA), resuspended in 200 microliters Binding Buffer with 27 pmol thrombin (=135 nM thrombin) and incubated at ambient temperature for 30 minutes, after which the mixture is centrifuged in mini-spin columns at 1677×g for 30 s to collect the flow-through. Beads are washed with 200 microliters Binding Buffer followed by 200 microliters Elution Buffer (50 mM Tris-HCl pH 7.5, 1 M NaCl, 0.1% BSA), and thrombin recovery is quantified by measuring rates of chromogenic Spectrozyme TH (H-d-hexahydrotyrosol-Ala-Arg-p-nitroanilide) hydrolysis compared to a standard curve. Salt sensitivities of thrombin-polyP interactions were investigated by modifying either the Binding or Elution Buffer to contain 50-1000 mM NaCl. Purification of a larger amount of thrombin using immobilized polyP is accomplished in a similar manner by standard methods, using larger columns and volumes.

E. Purification of Thrombin Using Fibrinogen

This purification method takes advantage of the fact that some, but not all, forms of thrombin bind to fibrinogen. Thrombin variants with a reduced affinity for fibrinogen, such as the thrombin W215A E217A variant, are not good candidates for purification by this method. Fibrinogen is conjugated to Sepharose 4B, using the method of Cuatrecasas ("Protein purification by affinity chromatography. Derivatizations of agarose and polyacrylamide beads", J Biol Chem 1970 June; 245(12): 3059-3065) with a final concentration of 2 mg of fibrinogen per 1 ml of Sepharose 4B. The resin is packed in a plastic column (1.5×3 cm, bed volume 6 ml) and equilibrated with 0.02 M NaCl/0.01 M Tris-HCl (pH 7.4). Thrombin, and to a lesser extent prethrombin-2, binds to the fibrinogen-Sepharose column, while prothrombin and prethrombin-1 do not; the affinity of thrombin and prethrombin-2 for fibrinogen-Sepharose depends on ionic strength and reaches a maximum at 50 mM concentration at 22 degrees C. (Kaczmarek et al., "Fibrinogen-sepharose interaction with prothrombin, prethrombin 1, prethrombin 2 and thrombin", Biochim Biophys Acta 1987 Aug. 21; 914(3): 275-282.). Thrombin is bound to the fibrinogen-Sepharose column in 50 mM NaCl/5 mM Tris-HCl (pH 7.4) at 22 degrees C. and after an optional wash step is eluted with 250 mM NaCl/5 mM Tris-HCl (pH 7.4).

Example 4

Additional Assays of Thrombin Activity
A. Chromogenic PAGE Blot Assay ("Eastern Blot")

This assay detects the presence of enzymatically active thrombin in the sample. A biological fluid sample, such as cell lysates or a concentrated sample of proteins released into the culture medium, is electrophoresed under gentle non-reducing, non-denaturing conditions to maintain the secondary structure of the protein. Following PAGE the proteins in the gel are transferred to nitrocellulose, and the nitrocellulose paper is developed with a suitable chromogenic substrate such as S-2238. Sample buffer (2x): 62.5 mM Tris-HCL pH 6.8; 25% glycerol (may contain 20 mM benzamidine). Running Buffer: 25 mM Tris; 192 mM glycine; pH 8.3. Transfer Buffer: 48 mM Tris, 39 mM glycine, 20% methanol. Standard enzyme ladder: purified thrombin, activated protein C, factor XIa, and possibly other purified and distinct (in terms of size and/or charge) serine proteases that cleave the substrate of choice (at approximately 0.1 micrograms/mL each, but could be more or less concentrated, depending on the expected concentration of the enzyme in the sample). The assay is specifically performed as follows:
1. Mix or dialyze sample with sample buffer. DO NOT heat the sample.
2. Load the sample and ladder at ~10 microliters per well of a 5 to 10% polyacrylamide gel (no SDS).
3. Load the sample mixture and set an appropriate voltage to run the electrophoresis (slowly, in a cold room).
4. Transfer the gel (proteins) to nitrocellulose paper.
5. Place gel in a petri dish that has 1 mM chromogenic or fluorescent substrate on the bottom.
6. Allow soak-through of the substrate into the paper for a few minutes, gently shaking the dish.
7. Remove excess substrate.
8. Cover dish air tight to prevent dry out of the nitrocellulose paper.
9. Wait for bands to appear.
10. Active thrombin in the sample appears as a band at the thrombin standard position. A single band suggests that it is probably active thrombin.
11. Additional bands indicate contamination with other proteases.

B. Fibrin Clotting Assay

Thrombin and most enzymatically active thrombin variants cleave soluble fibrinogen to insoluble fibrin. Fibrinogen (1 g lyophilized, Kabi Vitrum, Stockholm, Sweden), dissolved in water to a concentration of 4 mg/mL, is filtered through a 0.8 um syringe filter (Acrodisc 4188, Gelman-Sciences). Significantly lower concentrations of fibrinogen (e.g., 0.1 mg/mL) will also form a clot and may be more suitable for this simple assay.

Samples (100 microliters) containing WT thrombin or thrombin analogs (E-WE thrombin) are added to 96 well, flat bottom, clear microplate wells (Fisher brand 12565501). Once in the wells, 100 microliters fibrinogen solution is added, and the appearance of clots in the wells are observed visually (increase in turbidity). In this simple and thrombin-specific assay, fibrin forms a gel (clot) over time, and the clot that is readily detectable by the naked eye.

Change in absorbance of 405 nm light is measured using a microplate reader (Versa Max). Depending on the amount of thrombin pro-coagulant activity, clots appear in the wells over time. Both WT and E-WE thrombin (0.1 microgram/mL) clot fibrinogen, but the latter is about 1000-fold slower.

This assay may require higher thrombin concentrations to be useful, as fibrin inhibits thrombin (1:1), thus their ratio will have an effect on the outcome. The 1:1 stoichiometric ratio of fibrinogen to thrombin is about 10:1 by weight. Buffering of the sample can be important, as pH, salt, and other factors all affect thrombin activity and fibrin polymerization. The assay could be potentially improved by adding calcium (2-5 mM), and some purified factor XIII (maybe 1 nM), as FXIII, once activated by thrombin, cross-links the fibrin fibers, making it a more turbid or denser gel. Moreover, a chromogenic substrate for thrombin (e.g., S-2238 or S-2366) could also be added to the fibrinogen, which would be cleaved and increase the light absorbance of the clot, and would be cleaved by thrombin that is already bound to fibrin. However, the specificity of these small molecule substrates is limited. A specific small molecule thrombin inhibitor could be used for a negative control. A small molecule fibrinolysis inhibitor could also be added to reduce lysis of the clot (fibrinogen preps may be contaminated with plasminogen and plasminogen activators). Moreover, if you have an assay set up for fibrinopeptide A, this peptide can be measured in the supernatant (clots may have to be spun to get the soup) and will correlate with the thrombin concentration.

C. Chromogenic Assays for Thrombin Prothrombin-Cleaving Activity and Protein C Activation Prothrombin is cleaved by thrombin; chromogenic substrate peptides that are analogs of the cleavage site, such as S-2238 (D-Phe-Pip-Arg-p-nitroanilide), can be used to test for this activity. The substrate H-D-Phe-Pro-Arg-p-nitroanilide can also be used to assay prothrombin-cleaving activity, and the substrate H-D-Asp-Arg-Arg-p-nitroanilide is specific for activated protein C (Cantwell and Di Cera, "Rational design of a potent anticoagulant thrombin", J Biol Chem 2000 Dec. 22; 275(51): 39827-39830; Epub 2000 Nov. 1). To assess the catalytic efficiency of thrombin variants, kinetic constants are determined for the cleavage of S-2238. The release of p-nitroaniline resulting from the hydrolysis of S-2238 is followed by measuring the rate of increase in absorbance at 405 nm. All absorbance measurements are made on a modified Cary Model 14 spectrophotometer. The assays are carried out in polymethacrylate cuvettes at 37 degrees C. in assay buffer (50 mM Tris.HCl, 0.15 M NaCl, 0.1% PEG, pH 7.4). Both the 10 nM thrombin stock solution and the 2-30 micromolar S-2238 stock solutions are prepared in assay buffer. In addition, the thrombin solution contains 1 mg/ml bovine serum albumin. The absorbance at 342 nm of 990 microliters of S-2238 stock is recorded, then 10 microliters of thrombin stock (10 nM) is added, and the absorbance at 405 nm is monitored for 5-10 minutes at 37 degrees C. The amount of product formed is calculated by using an extinction coefficient of 9920 $M^{-1}$ $cm^{-1}$ for p-nitroaniline at 405 nm, and the concentration of S-2238 is determined by using an extinction coefficient of 8270 $M^{-1}$ $cm^{-1}$ at 342 nm. Values and standard deviations for $K_m$ and $k_{cat}$ are calculated from triplicate assays by least-squares fit to a straight line of a plot of the inverse of the rate of p-nitroaniline release against the inverse of the concentration of S-2238, using the program LINFIT (Bevington, "Data Reduction and Error Analysis for the Physical Sciences", McGraw-Hill New York 1969; 92-118). The kinetic constants for the hydrolysis of S-2238 by thrombin variants are compared with $k_{cat}$ (97±8 s$^{-1}$) and $K_m$ (2.71±0.25 micromolar) determined for wild-type thrombin (DiBella et al., "Expression and folding of recombinant bovine prethrombin-2 and its activation to thrombin", J Biol Chem 1995 Jan. 6; 270(1): 163-169).

D. Assay for Fibrinogen-Cleaving Activity

To assess the catalytic efficiency of thrombin variants, kinetic constants are determined for the release of fibrinogen peptide A (FpA) from fibrinogen. Approximately 0.01 NIH unit/ml (3 ng/ml) of wild-type thrombin or variant thrombin are incubated with 3.5 micromolar fibrinogen at 37 degrees C. in 50 mM $H_3PO_4$, 100 mM NaCl, 0.1% PEG 8000, pH 7.5. At designated times between 1 and 14 minutes, an aliquot of the reaction is quenched by adding 0.3 M perchloric acid. After an additional 10 minutes at 37 degrees C., the pH is raised to ~2 by adding 0.14 M NaOH. An infinity time point (30 minutes) for the FpA release assay is determined using wild-type thrombin or variant thrombin at a concentration of 0.05 NIH unit/ml. An LKB HPLC system consisting of a 2152 LC controller, a 2151 pump, a 2141 variable wavelength detector, a 2221 integrator, and a 2157 autosampler is used for the detection of FpA. For each time point, 900 microliters are loaded onto a Brownlee Aquapore RP-300 column (100×2.1 mm) equilibrated in 10% acetonitrile/0.1% trifluoroacetic acid, and FpA is eluted with a linear gradient from 10% acetonitrile/0.1% trifluoroacetic acid to 35% acetonitrile/0.1% trifluoroacetic acid in 35 minutes at a flow rate of 0.5 ml/min. Kinetic constants and standard deviations are determined by least-squares fit to a straight line of a plot of $-\ln\{([FpA]_\infty-[FpA]_t)/([FpA]_\infty-[FpA]_0)\}$ against time using the program LINFIT, where $[FpA]_0$ is a baseline correction. From the thrombin-mediated release of FpA from fibrinogen, a value for $k_{cat}/K_m$ is determined for the fibrinogen-cleaving activity of the thrombin variant and compared to that determined for wild-type thrombin (16.7±2.0 micromolar$^{-1}$ s$^{-1}$, DiBella 1995 supra).

Example 5

Inducible Coexpression of Thrombin in Yeast Cells

The coordinated coexpression in yeast host cells of thrombin expression constructs is achieved by the following method.

The pJ1231-03C and pJ1234-03C vectors (DNA2.0, Menlo Park, Calif.) were used as the backbone part of the yeast expression constructs, as they contain elements necessary for plasmid maintenance in either *E. coli* (pUC origin of replication) or *Saccharomyces cerevisiae* (2-micron circle origin of replication, along with selectable markers useful in either host: KanR (*E. coli*) and Leu2 (yeast) in pJ1231-03C; AmpR (*E. coli*) and Ura3 (yeast) in pJ1234-03C. The nucleotide sequences of the pJ1231-03C and pJ1234-03C vectors are shown as SEQ ID NOs 21 and 22, respectively. The pJ1231-03C and pJ1234-03C vectors are treated with BfuA1 restriction endonuclease (NEB, Catalog No. R0701S); fragments of the vectors that were not retained after BfuA1 digestion comprise an expression promoter, the DasherGFP coding sequence, and the CYC1 terminator sequence. PCR is performed on nucleotide sequences containing the coding sequences for the polypeptides to be expressed (such as expression constructs comprising the coding sequences for thrombin polypeptides), to create sequences that are then ligated into the BfuA1-cut pJ1231-03C and pJ1234-03C vectors. In addition to the coding sequences for thrombin polypeptides and the inducible promoters that will be driving the expression of those polypeptides, the PCR-amplified fragments should contain the coding sequences for the transcriptional activators of the inducible promoters, for example, PrpR or AraC. All PCR reactions are performed using Platinum® Pfx DNA Polymerase (Life Technologies, Grand Island, N.Y., Catalog No. 11708021), and the QIAEX II DNA purification kit (QIAGEN, Catalog No. 20051) is used for purification of PCR-product and vector fragments, according to the manufacturers' instructions. When the PCR-amplified fragments have been prepared and cut with the appropriate restriction enzymes, they are ligated into the BfuA1-cut pJ1231-03C vector or the BfuA1-cut pJ1234-03C vector using T4 DNA ligase, to create the expression constructs that will be used in the yeast cells. The ligase mixtures are transformed into *E. coli* DH5alpha cells and plated on LB agar plates with sufficient amounts of kanamycin or ampicillin to maintain the plasmids in the DH5alpha cells. Preparation of plasmid DNA is performed according to standard methods. (Optionally but preferably, the prepared plasmid DNA is used in sequencing reactions to confirm the sequences of the plasmid inserts.)

Competent INVSc-1 *S. cerevisiae* cells are prepared using the S.c. EasyComp™ Transformation Kit (Life Technologies, Catalog No. K5050-01) according to the manufacturer's instructions. The INVSc-1 *S. cerevisiae* strain has the following genotype (MATa his3Δ1 leu2 trp1-289 ura3-52/ MATα his3Δ1 leu2 trp1-289 ura3-52) and phenotype: His$^-$, Leu$^-$, Trp$^-$, Ura$^-$. Briefly, a single colony from the INVSc-1 strain is inoculated in 10 milliliters of YPD medium (contains, per liter: 10 g yeast extract, 20 g peptone, 20 g glucose) and grown overnight at 30 degrees C. in a shaking incubator at 250 rpm. Next day, the overnight culture is diluted in 10 milliliters fresh YPD medium to an OD600 of 0.3 and grown until OD600 reached 0.8. The cells are collected by centrifugation at 1500 rpm for 5 minutes at room temperature. After that, the cells are resuspended in 10 milliliters of Solution 1 (wash solution) and collected by centrifugation at 1500 rpm for 5 minutes at room temperature. Supernatant is discarded and cells are resuspended in 1 milliliter of Solution 2 (resuspension solution), divided in 50-microliter aliquots and stored at −80 degrees C. To transform the competent yeast cells with the expression constructs, 50 microliters of INVSc-1 competent cells are mixed with 1.2 micrograms of each expression vector or control vector and 500 microliters of Solution 3 (transformation solution). Then cells are mixed vigorously and incubated in a 30 degrees C. water bath for 1 hour and vortexed for 10 seconds every 15 minutes. 100- and 400-microliter aliquots of transformation mixtures are seeded on SC minimal agar plates in the absence of appropriate selective reagent. SC minimal medium contains, per liter: 6.7 g yeast nitrogen base, 20 g glucose, 0.05 g aspartic acid, 0.05 g histidine, 0.05 g isoleucine, 0.05 g methionine, 0.05 g phenylalanine, 0.05 g proline, 0.05 g serine, 0.05 g tyrosine, 0.05 g valine, 0.1 g adenine, 0.1 g arginine, 0.1 g cysteine, 0.1 g leucine (omitted in −Leu selective media), 0.1 g lysine, 0.1 g threonine, 0.1 g tryptophan, and 0.1 g uracil (omitted in −Ura selective media). INVSc-1 cells transformed with pJ1231-based expression constructs are selected on plates without leucine at 30 degrees C. for 48-72 hours. INVSc-1 cells transformed with pJ1234-based expression constructs are grown under the same conditions on SC minimal agar plates without uracil. INVSc-1 cells co-transformed simultaneously with pJ1231- and pJ1234-based expression constructs are selected under the same conditions on SC minimal agar plates without leucine or uracil.

Cells from all colonies from each transformation are scraped and resuspended in 4 milliliters of liquid minimal SC medium in absence of the appropriate selective reagent and carbon source. $OD_{600}$ in each culture was measured and normalized to 0.4 optical units. Protein expression is induced by addition of an appropriate amount, such as 1-2%, sterile filtered inducer(s) (Sigma-Aldrich, St. Louis, Mo., Catalog No. A3256-25G). The time course for protein expression is 24 hours, at 30 degrees C. in a shaking incubator at 250 rpm. Cells from 0.5 milliliters of each pre-induced culture are collected by centrifugation, washed with 1 milliliter of de-ionized water and stored at −80 degrees C. Samples from post-induced cultures are prepared in the same way. Total protein extracts are prepared from pre- and post-induced cultures, resolved in 4-20% SDS-PAGE, and transferred to a PDVF membrane. Expression level of target proteins was analyzed by Western blotting using antibodies such as anti-6×His tag (for His-tagged thrombin polypeptides) and anti-Human IgG secondary antibodies.

Example 6

Titration of Coexpression by Varying Inducer Concentration

To optimize production of a multimeric product using the inducible coexpression systems of the invention, it is possible to independently adjust or titrate the concentrations of the inducers. Host cells containing L-arabinose-inducible and propionate-inducible expression constructs are grown to the desired density (such as an $OD_{600}$ of approximately 0.5) in M9 minimal medium containing the appropriate antibiotics, then cells are aliquoted into small volumes of M9 minimal medium, optionally prepared with no carbon source such as glycerol, and with the appropriate antibiotics and varying concentrations of each inducer. The concentration of L-arabinose necessary to induce expression is typically less than 2%. In a titration experiment, the tested concentrations of L-arabinose can range from 2% to 1.5%, 1%, 0.5%, 0.2%, 0.1%, 0.05%, 0.04%, 0.03%, 0.02%, 0.01%, 0.005%, 0.002%, and 0.001%. The concentrations of L-rhamnose or D-xylose necessary to induce expression of L-rhamnose-inducible or D-xylose-inducible promoters are tested similarly, with the tested concentrations ranging from 5% to 0.01%. For each concentration 'x' of L-arabinose (or L-rhamnose or D-xylose) that is tested, the concentration of a different inducer such as propionate, added to each of the tubes containing concentration 'x' of the first inducer, is varied in each series of samples, which in the case of propionate range from 1 M to 750 mM, 500 mM, 250 mM, 100 mM, 75 mM, 50 mM, 25 mM, 10 mM, 5 mM, and 1 mM.

Alternatively, titration experiments can start at a 'standard' combination of inducer concentrations, which is 0.002% of any of L-arabinose, L-rhamnose, or D-xylose, and/or 50 mM propionate, and test new combinations of inducer concentrations that vary from that of the 'standard' combination. Similar titration experiments can be performed with any combination of inducers used in an inducible coexpression system of the invention, including but not limited to L-arabinose, propionate, L-rhamnose, and D-xylose. After growth in the presence of inducers for 6 hours, the cells are pelleted, the desired product is extracted from the cells, and the yield of product per mass value of cells is determined by a quantitative immunological assay such as ELISA, or by purification of the product and quantification by UV absorbance at 280 nm.

It is also possible to titrate inducer concentrations using a high-throughput assay, in which the proteins to be expressed are engineered to include a fluorescent protein moiety, such as that provided by the mKate2 red fluorescent protein (Evrogen, Moscow, Russia), or the enhanced green fluorescent proteins from *Aequorea victoria* and *Bacillus cereus*. Another approach to determining the amount and activity of gene products produced by different concentrations of inducers in a high-throughput titration experiment, is to use a sensor capable of measuring biomolecular binding interactions, such as a sensor that detects surface plasmon resonance, or a sensor that employs bio-layer interferometry (BLI) (for example, an Octet® QK system from forteBIO, Menlo Park, Calif.).

Example 7

Measurement of the Strength of Promoters and the Homogeneity of Inducible Expression The strength of a promoter is measured as the amount of transcription of a gene product initiated at that promoter, relative to a suitable control. For constitutive promoters directing expression of a gene product in an expression construct, a suitable control could use the same expression construct, except that the 'wild-type' version of the promoter, or a promoter from a 'housekeeping' gene, is used in place of the promoter to be tested. For inducible promoters, expression of the gene product from the promoter can be compared under inducing and non-inducing conditions.

A. Measuring Promoter Strength Using Quantitative PCR to Determine Levels of RNA Transcribed from the Promoter The method of De Mey et al. ("Promoter knock-in: a novel rational method for the fine tuning of genes", BMC Biotechnol 2010 Mar. 24; 10: 26) is used to determine the relative strength of promoters in host cells that can be grown in culture. Host cells containing an expression construct with the promoter to be tested, and control host cells containing a control expression construct, are grown in culture in triplicate. One-ml samples are collected at $OD_{600}$=1.0 for mRNA and protein collection. Total RNA extraction is done using an RNeasy mini kit (QIAGEN, The Netherlands). The purity of RNA is verified on a FA-agarose gel as recommended by QIAGEN and the RNA concentration is determined by measuring the absorbance at 260 nm. Two micrograms of RNA is used to synthesize cDNA using a random primer and RevertAid H Minus M-MulV reverse transcriptase (Fermentas, Glen Burnie, Md.). The strength of the promoter is determined by RT-qPCR carried out in an iCycler IQ° (Bio-Rad, Eke, Belgium) using forward and reverse primers designed to amplify the cDNA corresponding to the transcript produced from the promoter. (For this purpose, the De Mey et al. authors used the Fw-ppc-qPCR and Rv-ppc-qPCR primers, and the primers Fw-rpoB-qPCR and Rv-rpoB-qPCR from the control housekeeping gene rpoB.) SYBR GreenER qPCR supermix (Life Technologies, Grand Island, N.Y.) is used to perform a brief UDG (uracil DNA glycosylase) incubation (50° C. for 2 min) immediately followed by PCR amplification (95° C. for 8.5 min; 40 cycles of 95° C. for 15 s and 60° C. for 1 min) and melting curve analysis (95° C. for 1 min, 55° C. for 1 min and 80 cycles of 55° C.+0.5° C./cycles for 10 s) to identify the presence of primer dimers and analyze the specificity of the reaction. This UDG incubation step before PCR cycling destroys any contaminating dU-containing products from previous reactions. UDG is then inactivated by the high temperatures during normal PCR cycling, thereby allowing the amplification of genuine target sequences. Each sample is performed in triplicate. The relative expression ratios are calculated using the "Delta-delta ct method" of PE Applied Biosystems (PerkinElmer, Forster City, Calif.).

B. Measuring Inducible Promoter Strength and Homogeneity of Induction Using a Fluorescent Reporter Gene These experiments are performed using the methods of Khlebnikov et al. ("Regulatable arabinose-inducible gene expression system with consistent control in all cells of a culture", J Bacteriol 2000 December; 182(24): 7029-7034). Experiments measuring the induction of an inducible promoter are performed in C medium supplemented with 3.4% glycerol as a carbon source (Helmstetter, "DNA synthesis during the division cycle of rapidly growing *Escherichia coli* B/r", J Mol Biol 1968 Feb. 14; 31(3): 507-518). *E. coli* strains containing expression constructs comprising at least one inducible promoter controlling expression of a fluorescent reporter gene are grown at 37° C. under antibiotic selection to an optical density at 600 nm (OD600) of 0.6 to 0.8. Cells are collected by centrifugation (15,000×g), washed in C medium without a carbon source, resuspended in fresh C medium containing antibiotics, glycerol, and/or inducer (for the induction of gene expression) to an OD600 of 0.1 to 0.2, and incubated for 6 h. Samples are taken routinely during the growth period for analysis. Culture fluorescence is measured on a Versafluor Fluorometer (Bio-Rad Inc., Hercules, Calif.) with 360/40-nm-wavelength excitation and 520/10-nm-wavelength emission filters. The strength of expression from an inducible promoter upon induction can be expressed as the ratio of the maximum population-averaged fluorescence (fluorescence/OD ratio) of the induced cells relative to that of control (such as uninduced) cells. To determine the homogeneity of induction within the cell population, flow cytometry is performed on a Beckman-Coulter EPICS XL flow cytometer (Beckman Instruments Inc., Palo Alto, Calif.) equipped with an argon laser (emission at a wavelength of 488 nm and 15 mW) and a 525-nm-wavelength band pass filter. Prior to the analysis, sampled cells are washed with phosphate-buffered saline that had been filtered (filter pore size, 0.22 micrometers), diluted to an OD600 of 0.05, and placed on ice. For each sample, 30,000 events are collected at a rate between 500 and 1,000 events/s. The percentage of induced (fluorescent) cells in each sample can be calculated from the flow cytometry data.

Example 8

Characterizing the Disulfide Bonds Present in Coexpression Products

The number and location of disulfide bonds in coexpressed protein products can be determined by digestion of the protein with a protease, such as trypsin, under non-reducing conditions, and subjecting the resulting peptide fragments to mass spectrometry (MS) combining sequential electron transfer dissociation (ETD) and collision-induced dissociation (CID) MS steps (MS2, MS3) (Nili et al., "Defining the disulfide bonds of insulin-like growth factor-binding protein-5 by tandem mass spectrometry with electron transfer dissociation and collision-induced dissociation", J Biol Chem 2012 Jan. 6; 287(2): 1510-1519; Epub 2011 Nov. 22).

Digestion of Coexpressed Protein.

To prevent disulfide bond rearrangements, any free cysteine residues are first blocked by alkylation: the coexpressed protein is incubated protected from light with the alkylating agent iodoacetamide (5 mM) with shaking for 30 minutes at 20° C. in buffer with 4 M urea, and then is separated by non-reducing SDS-PAGE using precast gels. Alternatively, the coexpressed protein is incubated in the gel after electrophoresis with iodoacetamide, or without as a control. Protein bands are stained, de-stained with double-deionized water, excised, and incubated twice in 500 microliters of 50 mM ammonium bicarbonate, 50% (v/v) acetonitrile while shaking for 30 minutes at 20° C. Protein samples are dehydrated in 100% acetonitrile for 2 minutes, dried by vacuum centrifugation, and rehydrated with 10 mg/ml of trypsin or chymotrypsin in buffer containing 50 mM ammonium bicarbonate and 5 mM calcium chloride for 15 minutes on ice. Excess buffer is removed and replaced with 50 microliters of the same buffer without enzyme, followed by incubation for 16 hours at 37° C. or 20° C., for trypsin and chymotrypsin, respectively, with shaking. Digestions are stopped by addition of 3 microliters of 88% formic acid, and after brief vortexing, the supernatant is removed and stored at −20° C. until analysis.

Localization of Disulfide Bonds by Mass Spectrometry.

Peptides are injected onto a 1 mm×8 mm trap column (Michrom BioResources, Inc., Auburn, Calif.) at 20 microliters/minute in a mobile phase containing 0.1% formic acid. The trap cartridge is then placed in-line with a 0.5 mm×250 mm column containing 5 mm Zorbax SB-C18 stationary phase (Agilent Technologies, Santa Clara, Calif.), and peptides separated by a 2-30% acetonitrile gradient over 90 minutes at 10 microliters/minute with a 1100 series capillary HPLC (Agilent Technologies). Peptides are analyzed using a LTQ Velos linear ion trap with an ETD source (Thermo Scientific, San Jose, Calif.). Electrospray ionization is performed using a Captive Spray source (Michrom Bioresources, Inc.). Survey MS scans are followed by seven data-dependant scans consisting of CID and ETD MS2 scans on the most intense ion in the survey scan, followed by five MS3 CID scans on the first- to fifth-most intense ions in the ETD MS2 scan. CID scans use normalized collision en-ergy of 35, and ETD scans use a 100 ins activation time with supplemental activation enabled. Minimum signals to initiate MS2 CID and ETD scans are 10,000, minimum signals for initiation of MS3 CID scans are 1000, and isolation widths for all MS2 and MS3 scans are 3.0 m/z. The dynamic exclusion feature of the software is enabled with a repeat count of 1, exclusion list size of 100, and exclusion duration of 30 s. Inclusion lists to target specific cross-linked species for collection of ETD MS2 scans are used. Separate data files for MS2 and MS3 scans are created by Bioworks 3.3 (Thermo Scientific) using ZSA charge state analysis. Matching of MS2 and MS3 scans to peptide sequences is performed by Sequest (V27, Rev 12, Thermo Scientific). The analysis is performed without enzyme specificity, a parent ion mass tolerance of 2.5, fragment mass tolerance of 1.0, and a variable mass of +16 for oxidized methionine residues. Results are then analyzed using the program Scaffold (V3_00_08, Proteome Software, Portland, Oreg.) with minimum peptide and protein probabilities of 95 and 99% being used. Peptides from MS3 results are sorted by scan number, and cysteine containing peptides are identified from groups of MS3 scans produced from the five most intense ions observed in ETD MS2 scans. The identities of cysteine peptides participating in disulfide-linked species are further confirmed by manual examination of the parent ion masses observed in the survey scan and the ETD MS2 scan.

Example 9

Isolation of Coexpression Products from Bacterial Cell Periplasm, from Spheroplasts, and from Whole Cells The inducible coexpression system of the invention can be used to express gene products that accumulate in different compartments of the cell, such as the cytoplasm or periplasm. Host cells such as *E. coli* or *S. cerevisiae* have an outer cell membrane or cell wall, and can form spheroplasts when the outer membrane or wall is removed. Coexpressed proteins made in such hosts can be purified specifically from the periplasm, or from spheroplasts, or from whole cells, using the following method (Schoenfeld, "Convenient, rapid enrichment of periplasmic and spheroplasmic protein fractions using the new PeriPreps™ Periplasting Kit", Epicentre Forum 1998 5(1): 5; see epibio.com/newsletter/f5_1/f5_lpp.asp). This method, using the PeriPreps™ Periplasting Kit (Epicentre® Biotechnologies, Madison Wis.; protocol available at epibio.com/pdftechlit/107p10612.pdf), is designed for *E. coli* and other grain negative bacteria, but the general approach can be modified for other host cells such as *S. cerevisiae*.

1. The bacterial host cell culture is grown to late log phase only, as older cell cultures in stationary phase commonly demonstrate some resistance to lysozyme treatment. If the expression of recombinant protein is excessive, cells may pre-maturely lyse; therefore, cell cultures are not grown in rich medium or at higher growth temperatures that might induce excessive protein synthesis. Protein expression is then induced; the cells should be in log phase or early stationary phase.

2. The cell culture is pelleted by centrifugation at a minimum of 1,000×g for 10 minutes at room temperature. Note: the cells must be fresh, not frozen. The wet weight of the cell pellet is determined in order to calculate the amount of reagents required for this protocol.

3. The cells are thoroughly resuspended in a minimum of 2 ml of PeriPreps Periplasting Buffer (200 mM Tris-HCl pH 7.5, 20% sucrose, 1 mM EDTA, and 30 U/microliter Ready-Lyse Lysozyme) for each gram of cells, either by vortex mixing or by pipeting until the cell suspension is homogeneous. Note: excessive agitation may cause premature lysing of the spheroplasts resulting in contamination of the periplasmic fraction with cytoplasmic proteins.

4. Incubate for five minutes at room temperature. Ready-Lyse Lysozyme is optimally active at room temperature. Lysis at lower temperatures (0° C.–4° C.) requires additional incubation time; at such temperatures incubation times are extended 2- to 4-fold.

5. Add 3 ml of purified water at 4° C. for each grain of original cell pellet weight (Step 2) and mix by inversion.

6. Incubate for 10 minutes on ice.

7. The lysed cells are pelleted by centrifugation at a minimum of 4,000×g for 15 minutes at room temperature.

8. The supernatant containing the periplasmic fraction is transferred to a clean tube.

9. To degrade contaminating nucleic acids, OmniCleave Endonuclease is optionally added to PeriPreps Lysis Buffer. Inclusion of a nuclease will generally improve the yield of protein and the ease of handling of the lysates, but addition of a nuclease is undesirable in some cases: for example, the use of a nuclease should be avoided if residual nuclease activity or transient exposure to the magnesium cofactor will interfere with subsequent assays or uses of the purified protein. The addition of EDTA to the lysate to inactivate OmniCleave Endonuclease, likewise, may interfere with subsequent assay or use of the purified protein. If nuclease is to be added, 2 microliters of OmniCleave Endonuclease and 10 microliters of 1.0 M $MgCl_2$ are diluted up to 1 ml with PeriPreps Lysis Buffer (10 mM Tris-HCl pH 7.5, 50 mM KCl, 1 mM EDTA, and 0.1% deoxycholate) for each milliliter of Lysis Buffer needed in Step 10.

10. The pellet is resuspended in 5 ml of PeriPreps Lysis Buffer for each gram of original cell pellet weight.

11. The pellet is incubated at room temperature for 10 minutes (if included, OmniCleave Endonuclease activity will cause a significant decrease in viscosity; the incubation is continued until the cellular suspension has the consistency of water).

12. The cellular debris is pelleted by centrifugation at a minimum of 4,000×g for 15 minutes at 4° C.

13. The supernatant containing the spheroplast fraction is transferred to a clean tube.

14. If OmniCleave Endonuclease was added to the PeriPreps Lysis Buffer, 20 microliters of 500 mM EDTA is added for each milliliter of the resultant spheroplastic fraction, to chelate the magnesium (the final concentration of EDTA in the lysate is 10 mM). Following hydrolysis of nucleic acids with OmniCleave Endonuclease, lysates may contain substantial amounts of mono- or oligonucleotides. The presence of these degradation products may affect further processing of the lysate: for example, nucleotides may decrease the binding capacity of anion exchange resins by interacting with the resin.

The above protocol can be used to prepare total cellular protein with the following modifications. The cells pelleted in Step 2 can be fresh or frozen; at Step 4, the cells are incubated for 15 minutes; Steps 5 through 8 are omitted; at Step 10, 3 ml of PeriPreps Lysis Buffer is added for each grain of original cell pellet weight.

After preparation of periplasmic, or spheroplastic, or whole-cell protein samples, the samples can be analyzed by any of a number of protein characterization and/or quantification methods. In one example, the successful fractionation of periplasmic and spheroplastic proteins is confirmed by analyzing an aliquot of both the periplasmic and spheroplastic fractions by SDS-PAGE (two microliters of each fraction is generally sufficient for visualization by staining with Coomassie Brilliant Blue). The presence of unique proteins or the enrichment of specific proteins in a given fraction indicates successful fractionation. For example, if the host cell contains a high-copy number plasmid with the ampicillin resistance marker, then the presence of β-lactamase (31.5 kDa) mainly in the periplasmic fraction indicates successful fractionation. Other *E. coli* proteins found in the periplasmic space include alkaline phosphatase (50 kDa) and elongation factor Tu (43 kDa). The amount of protein found in a given fraction can be quantified using any of a number of methods (such as SDS-PAGE and densitometry analysis of stained or labeled protein bands, scintillation counting of radiolabeled proteins, enzyme-linked immunosorbent assay (ELISA), or scintillation proximity assay, among other methods.) Comparing the amounts of a protein found in the periplasmic fraction as compared to the spheroplastic fraction indicates the degree to which the protein has been exported from the cytoplasm into the periplasm.

Example 10

Determination of Polynucleotide or Amino Acid Sequence Identity Percent polynucleotide sequence or amino acid sequence identity is defined as the number of aligned symbols, i.e. nucleotides or amino acids, that are identical in both aligned sequences, divided by the total number of symbols in the alignment of the two sequences, including gaps. The degree of similarity (percent identity) between two sequences may be determined by aligning the sequences using the global alignment method of Needleman and Wunsch (*J. Mol. Biol.* 48:443, 1970), as implemented by the National Center for Biotechnology Information (NCBI) in the Needleman-Wunsch Global Sequence Alignment Tool, available through the website blast.ncbi.nlm.nih.gov/Blast.cgi. In one embodiment, the Needleman and Wunsch alignment parameters are set to the default values (Match/Mismatch Scores of 2 and −3, respectively, and Gap Costs for Existence and Extension of 5 and 2, respectively). Other programs used by those skilled in the art of sequence comparison may also be used to align sequences, such as, for example, the basic local alignment search tool or BLAST® program (Altschul et al., "Basic local alignment search tool", J Mol Biol 1990 Oct. 5; 215(3): 403-410), as implemented by NCBI, using the default parameter settings described at the blast.ncbi.nlm.nih.gov/Blast.cgi website. The BLAST algorithm has multiple optional parameters including two that may be used as follows: (A) inclusion of a filter to mask segments of the query sequence that have low compositional complexity or segments consisting of short-periodicity internal repeats, which is preferably not utilized or set to 'off', and (B) a statistical significance threshold for reporting matches against database sequences, called the 'Expect' or E-score (the expected probability of matches being found merely by chance; if the statistical significance ascribed to a match is greater than this E-score threshold, the match will not be reported). If this 'Expect' or E-score value is adjusted from the default value (10), preferred threshold values are 0.5, or in order of increasing preference, 0.25, 0.1, 0.05, 0.01, 0.001, 0.0001, 0.00001, and 0.000001.

In practicing the present invention, many conventional techniques in molecular biology, microbiology, and recombinant DNA technology are optionally used. Such conventional techniques relate to vectors, host cells, and recombinant methods. These techniques are well known and are explained in, for example, Berger and Kimmel, Guide to Molecular Cloning Techniques, Methods in Enzymology volume 152 Academic Press, Mc, San Diego, Calif.; Sambrook et al., Molecular Cloning—A Laboratory Manual (3rd Ed.), Vol. 1-3, Cold Spring Harbor Laboratory, Cold Spring Harbor, N.Y., 2000; and Current Protocols in Molecular Biology, F. M. Ausubel et al., eds., Current Protocols, a joint venture between Greene Publishing Associates, Inc. and John Wiley & Sons, Inc., (supplemented through 2006). Other useful references, for example for cell isolation and culture and for subsequent nucleic acid or protein isolation, include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg N.Y.); and Atlas and Parks (Eds.) The Handbook of Microbiological Media (1993) CRC Press, Boca Raton, Fla. Methods of making nucleic acids (for example, by in vitro amplification, purification from cells, or chemical synthesis), methods for manipulating nucleic acids (for example, by site-directed mutagenesis, restriction enzyme digestion, ligation, etc.), and various vectors, cell lines, and the like useful in manipulating and making nucleic acids are described in the above references. In addition, essentially any polynucleotide (including labeled or biotinylated polynucleotides) can be custom or standard ordered from any of a variety of commercial sources.

The present invention has been described in terms of particular embodiments found or proposed to comprise certain modes for the practice of the invention. It will be appreciated by those of ordinary skill in the art that, in light of the present disclosure, numerous modifications and changes can be made in the particular embodiments exemplified without departing from the intended scope of the invention.

All cited references, including patent publications, are incorporated herein by reference in their entirety. Nucleotide and other genetic sequences, referred to by published genomic location or other description, are also expressly incorporated herein by reference.

| SEQUENCES PRESENTED IN THE SEQUENCE LISTING | | | | |
|---|---|---|---|---|
| SEQ ID NO: | Length: | Type: | Organism: | Description; 'Other Information' |
| 1 | 622 | PRT | Homo sapiens | Preprothrombin |
| 2 | 140 | DNA | Artificial Sequence | Optimized coding sequence for human thrombin A chain (with methionine residue added to the N-terminal end) |
| 3 | 37 | PRT | Artificial Sequence | Human thrombin A chain (with methionine residue added to the N-terminal end) |
| 4 | 260 | PRT | Artificial Sequence | Human thrombin B chain (with methionine residue added to the N-terminal end) |
| 5 | 809 | DNA | Artificial Sequence | Optimized coding sequence for human W215A E217A thrombin B chain (with methionine residue added to the N-terminal end) |
| 6 | 260 | PRT | Artificial Sequence | Human W215A E217A thrombin B chain (with methionine residue added to the N-terminal end) |
| 7 | 179 | DNA | Artificial Sequence | Optimized coding sequence for human thrombin A chain, with 14 amino acids added to the N-terminal end |
| 8 | 50 | PRT | Artificial Sequence | Human thrombin A chain, with 14 amino acids added to the N-terminal end |
| 9 | 956 | DNA | Artificial Sequence | Optimized coding sequence for human thrombin A/W215A E217A B chains (W215A E217A prethrombin-2), with 14 amino acids added to the N-terminal end |
| 10 | 309 | PRT | Artificial Sequence | Human thrombin A/W215A E217A B chains (W215A E217A prethrombin-2), with 14 amino acids added to the N-terminal end |
| 11 | 1310 | DNA | Artificial Sequence | Optimized coding sequence for mature ecarin from Echis carinatus (with methionine residue added to the N-terminal end) |
| 12 | 427 | PRT | Artificial Sequence | Mature ecarin from Echis carinatus (with methionine residue added to the N-terminal end) |
| 13 | 5882 | DNA | Artificial Sequence | pPRO33 vector |
| 14 | 5977 | DNA | Artificial Sequence | pPRO33_A expression construct |
| 15 | 6016 | DNA | Artificial Sequence | pPRO33_A+ expression construct |
| 16 | 5302 | DNA | Artificial Sequence | pBAD_WE-B expression construct |
| 17 | 5449 | DNA | Artificial Sequence | pBAD_A+/WE-B expression construct |
| 18 | 7147 | DNA | Artificial Sequence | pPRO33_ecarin expression construct |
| 19 | 5883 | DNA | Artificial Sequence | pPRO43 vector |
| 20 | 35 | DNA | Artificial Sequence | J23104 promoter |
| 21 | 6545 | DNA | Artificial Sequence | pJ1231-03C plasmid |
| 22 | 6009 | DNA | Artificial Sequence | pJ1234-03C plasmid |

What is claimed is:

1. An isolated host cell in culture comprising two or more types of expression constructs,
wherein each type of expression construct comprises at least one promoter selected from the group consisting of *Escherichia coli* sugar-inducible promoters and propionate-inducible promoters, and the expression construct of each type comprises an inducible promoter that is different from at least one said inducible promoter of the expression construct of each other type, and wherein each inducible promoter is not a lactose-inducible promoter, and
wherein the host cell has a reduced level of gene function of at least one gene encoding a protein that metabolizes an inducer of at least one said inducible promoter, and
wherein at least one said expression construct comprises a polynucleotide sequence encoding a polypeptide selected from the group consisting of:
(a) a polypeptide comprising the amino acid sequence of the thrombin A chain;
(b) a polypeptide comprising the amino acid sequence of the thrombin B chain; and
(c) a polypeptide that comprises the amino acid sequences of the thrombin A chain and the thrombin B chain, and is longer than prethombin-2 and shorter than prethrombin-1; and
wherein a host cell comprising at least one said expression construct that encodes a polypeptide comprising the amino acid sequence of the thrombin A chain further comprises a polynucleotide sequence encoding the amino acid sequence of the thrombin B chain, and said polynucleotide sequence encoding the amino acid sequence of the thrombin A chain is not contiguous with said polynucleotide sequence encoding the amino acid sequence of the thrombin B chain, and
wherein a host cell comprising at least one said expression construct that encodes a polypeptide comprising the amino acid sequence of the thrombin B chain further comprises a polynucleotide sequence encoding the amino acid sequence of the thrombin A chain, and said polynucleotide sequence encoding the amino acid sequence of the thrombin A chain is not contiguous with said polynucleotide sequence encoding the amino acid sequence of the thrombin B chain.

2. The host cell of claim 1 wherein at least one said expression construct comprises an inducible promoter selected from the group consisting of an L-arabinose-inducible promoter and a propionate-inducible promoter.

3. The host cell of claim 1 wherein the polypeptide comprising the amino acid sequence of the thrombin A chain comprises an amino acid sequence selected from the group consisting of: SEQ ID NO:3 and SEQ ID NO:8.

4. The host cell of claim 1 wherein the polypeptide comprising the amino acid sequence of the thrombin B chain comprises an amino acid sequence selected from the group consisting of SEQ ID NO:4 and SEQ ID NO:6.

5. The host cell of claim 1 wherein the polypeptide comprises a human thrombin amino acid sequence variation selected from the group consisting of: E14eA/D141A/E18A; G14mP; R93A/W215A/E217A; T172Y/W215A/E217A; S195A; W215A; W215A/E217A; W215E; W215G; a deletion of residues E146-K149e; W215G/a deletion of residues E146-K149e; W215L; W215V; E217A; and E229K.

6. The host cell of claim 5 wherein the polypeptide comprises the thrombin amino acid sequence variation W215A/E217A.

7. The host cell of claim 6 wherein the polypeptide comprises an amino acid sequence selected from the group consisting of: SEQ ID NO:6 and SEQ ID NO:10.

8. The host cell of claim 1 wherein at least one expression construct comprises an inducible promoter selected from the group consisting of: the araBAD promoter, the prpBCDE promoter, the rhaSR promoter, and the xylA promoter.

9. The host cell of claim 1 wherein the host cell comprises at least one expression construct encoding at least one disulfide bond isomerase protein.

10. The host cell of claim 1 wherein the host cell is a prokaryotic cell.

11. The host cell of claim 10 wherein the host cell is *E. coli*.

12. The host cell of claim 11 further comprising two or more of the following: (a) a deletion of the araBAD genes; (b) an altered gene function of the araE gene; (c) an altered gene function of the araFGH genes; (d) a lacY(A177C)

gene; (e) a reduced gene function of the prpB and prpD genes; (f) a reduced gene function of the sbm/scpA-ygfD/argK-ygfGH/scpBC genes without affecting expression of the ygfI gene; (g) a reduced gene function of the gor and trxB genes; (h) a reduced gene function of the AscG gene; (i) a polynucleotide encoding a form of DsbC lacking a signal peptide; (j) a polynucleotide encoding Erv1p; (k) a polynucleotide encoding protein disulfide isomerase; and (1) a polynucleotide encoding a chaperone.

13. A method of producing at least one thrombin polypeptide, the method comprising growing a culture of the host cell of claim 1.

14. A method of producing at least one thrombin polypeptide, the method comprising growing a culture of the host cell of claim 1 and adding an inducer of at least one inducible promoter to the culture.

* * * * *